(12) United States Patent
Pennell et al.

(10) Patent No.: US 11,649,261 B2
(45) Date of Patent: May 16, 2023

(54) CRYSTALLINE FORMS OF A CD73 INHIBITOR AND USES THEREOF

(71) Applicant: ARCUS BIOSCIENCES, INC., Hayward, CA (US)

(72) Inventors: Andrew M. K. Pennell, San Francisco, CA (US); Eric F. Connor, Los Gatos, CA (US); Stephen Edmund Gottschling, Bolton (CA); Jim Dimetrios Colomvakos, Scarborough (CA); Mohammed Asadullah Khan, Scarborough (CA)

(73) Assignee: ARCUS BIOSCIENCES, INC., Hayward, CA (US)

( * ) Notice: Subject to any disclaimer, the term of this patent is extended or adjusted under 35 U.S.C. 154(b) by 17 days.

(21) Appl. No.: 17/348,833

(22) Filed: Jun. 16, 2021

(65) Prior Publication Data
US 2021/0395291 A1 Dec. 23, 2021

Related U.S. Application Data

(60) Provisional application No. 63/040,277, filed on Jun. 17, 2020.

(51) Int. Cl.
| | | |
|---|---|---|
| C07H 19/23 | (2006.01) | |
| A61K 45/06 | (2006.01) | |
| C07K 16/28 | (2006.01) | |

(52) U.S. Cl.
CPC ............ *C07H 19/23* (2013.01); *A61K 45/06* (2013.01); *C07K 16/2818* (2013.01); *C07K 16/2827* (2013.01); *C07B 2200/13* (2013.01)

(58) Field of Classification Search
None
See application file for complete search history.

(56) References Cited

U.S. PATENT DOCUMENTS

| | | |
|---|---|---|
| 9,090,697 B2 | 7/2015 | Sim |
| 10,239,912 B2 | 3/2019 | Debien et al. |
| 10,981,944 B2 | 4/2021 | Debien et al. |
| (Continued) | | |

FOREIGN PATENT DOCUMENTS

| | | |
|---|---|---|
| WO | 2015/164573 A1 | 10/2015 |
| WO | WO-2017120508 | 7/2017 |
| (Continued) | | |

OTHER PUBLICATIONS

International Search Report dated Feb. 28, 2020 corresponding to PCT/US2019/065916 filed Dec. 12, 2019; 3 pages.

(Continued)

*Primary Examiner* — Traviss C McIntosh, III
(74) *Attorney, Agent, or Firm* — Sheppard Mullin Richter & Hampton LLP

(57) ABSTRACT

Crystalline forms of the compound of Formula (I), which modulates the conversion of AMP to adenosine by 5'-nucleotidase, ecto, and compositions containing the compound and methods for preparing the crystalline forms, are described herein. The use of such crystalline form of Formula (I) and compositions for the treatment and/or prevention of a diverse array of diseases, disorders and conditions, including cancer and immune-related disorders, that are mediated by 5'-nucleotidase, ecto is also provided.

23 Claims, 20 Drawing Sheets

(56) References Cited

U.S. PATENT DOCUMENTS

| | | | |
|---|---|---|---|
| 11,001,603 B2 | 5/2021 | Debien et al. | |
| 2017/0267710 A1* | 9/2017 | Debien | A61K 31/7076 |
| 2020/0405629 A1 | 12/2020 | Jaen et al. | |
| 2021/0371449 A1 | 12/2021 | Debien et al. | |
| 2022/0062313 A1 | 3/2022 | Jeffrey et al. | |

FOREIGN PATENT DOCUMENTS

| | | |
|---|---|---|
| WO | WO-2019173682 | 9/2019 |
| WO | WO-2020123772 | 6/2020 |

OTHER PUBLICATIONS

Written Opinion of the International Search Authority dated Feb. 28, 2020 corresponding to PCT/US2019/065916 filed Dec. 12, 2019; 4 pages.

U.S. Appl. No. 17/193,473, filed May 13, 2021, Lawson et al.

U.S. Appl. No. 17/206,896 filed Mar. 19, 2021, Debien et al.

Caira, M., Crystalline Polymorphism of Organic Compounds, Topics in Current Chemistry 1998, vol. 198. Springer, Berlin, Heidelberg, pp. 163-208.

International Search Report and Written Opinion for International Application No. PCT/US2021/037535 dated Oct. 7, 2021. 12 pages.

\* cited by examiner

CRYSTALLINE FORMS OF A CD73 INHIBITOR AND USES THEREOF

CROSS-REFERENCES TO RELATED APPLICATIONS

This application claims the benefit under 35 U.S.C. 119(e) of U.S. Provisional Application No. 63/040,277, filed Jun. 17, 2020, which is incorporated by reference herein in its entirety for all purposes.

FIELD

Provided herein are, for example, crystalline forms of a compound and compositions for inhibition of adenosine by 5'-nucleotidase, ecto, also known as CD73, and pharmaceutical compositions comprising same. Also provided herein are, for example, methods of treating or preventing a disease, disorder or condition, or a symptom thereof, mediated by inhibition of adenosine by 5'-nucleotidase, ecto.

BACKGROUND OF THE DISCLOSURE

Ectonucleotides catalyze the conversion of ATP to adenosine, an endogenous modulator that impacts multiple systems, including the immune system, the cardiovascular system, the central nervous system, and the respiratory system. Adenosine also promotes fibrosis in a variety of tissues. In the first step of the production of adenosine, ectonucleoside triphosphate diphosphohydrolase 1 (ENTPD1), also known as CD39 (Cluster of Differentiation 39), hydrolyzes ATP to ADP, and then ADP to AMP. In the next step, AMP is converted to adenosine by 5'-nucleotidase, ecto (NT5E or 5NT), also known as CD73 (Cluster of Differentiation 73).

The enzymatic activities of CD39 and CD73 play strategic roles in calibrating the duration, magnitude, and chemical nature of purinergic signals delivered to various cells (e.g., immune cells). Alteration of these enzymatic activities can change the course or dictate the outcome of several pathophysiological events, including cancer, autoimmune diseases, infections, atherosclerosis, and ischemia-reperfusion injury, suggesting that these ecto-enzymes represent novel therapeutic targets for managing a variety of disorders.

CD73 inhibition with monoclonal antibodies, siRNA, or small molecules delays tumor growth and metastasis (Stagg, J. (2010) PNAS U.S.A. 107:1547-52). For example, anti-CD73 antibody therapy was shown to inhibit breast tumor growth and metastasis in animal models (Stagg, J. (26 Jan. 2010) PNAS U.S.A, 107(4):1547-52). In addition, the use of antibodies that specifically bind CD73 has been evaluated for the treatment of bleeding disorders (e.g., hemophilia) (U.S. Pat. No. 9,090,697). There have been several efforts to develop therapeutically useful CD73 small molecule inhibitors. However, the development of small molecules has been hampered due to, for example, less than ideal physical and metabolic stability.

The compound (((((2R,3S,4R,5R)-5-(6-chloro-4-(((S)-1-(2-fluorophenyl)ethyl)amino)-1H-pyrazolo[3,4-b]pyridin-1-yl)-3,4-dihydroxytetrahydrofuran-2-yl)methoxy)(hydroxy)-phosphoryl)methyl)phosphonic acid, designated herein as Compound I, is a potent and selective small-molecule inhibitor of CD73. In view of the role played by CD73 in cancer, as well as a diverse array of other diseases, disorders and conditions, and the current lack of CD73 inhibitors available to medical practitioners, there is a need for stable crystalline forms of Compound I, as well as compositions and methods associated therewith.

BRIEF SUMMARY OF THE DISCLOSURE

The present disclosure relates to crystalline forms of a compound that modulates the conversion of AMP to adenosine by 5'-nucleotidase, ecto (NT5E or 5NT; also known as CD73), and compositions (e.g., pharmaceutical compositions) comprising the compound. Such a compound (in a crystalline form), including methods of preparation, methods of use, and compositions are described in detail below.

In one aspect, the present disclosure provides a crystalline form of a compound having Formula (I):

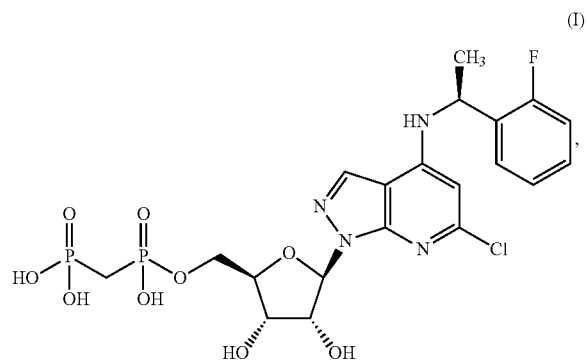 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

(I)

wherein the crystalline form is any one of crystalline Forms I to VI, each of which is characterized by an X-ray powder diffraction (XRPD) pattern as described herein.

In another aspect, the present disclosure provides a process for preparing a crystalline form of a compound of Formula (I), the process including:
a) forming a first mixture comprising a compound of Formula (I) and a solvent at a temperature of at least 20° C.; and
b) adding an anti-solvent to the first mixture to form a second mixture,
or
a) forming a first mixture comprising a compound of Formula (I) and a solvent at a temperature of at least 20° C.;
c) cooling the first or second mixture and stirring to form a precipitate;
d) isolating the precipitate; and
e) drying the precipitate to provide the crystalline form of Formula (I),
wherein the solvent is a $C_{1-4}$ alkyl alcohol, a di-($C_{1-4}$ alkyl) ether, a 5-6 membered cyclic ether, acetic acid, or water; and the anti-solvent is a $C_{5-7}$alkane, $C_{1-4}$alkyl alcohol, a di-($C_{1-4}$alkyl) ether,
a 5-6 membered cyclic ether, a di-($C_{1-4}$alkyl) ketone, $C_{1-4}$ alkyl-C(O)O—$C_{1-4}$alkyl, or an aromatic hydrocarbon solvent,
provided that the solvent and anti-solvent are not each a $C_{1-4}$alkyl alcohol, a di-($C_{1-4}$alkyl) ether, or a 5-6 membered cyclic ether.

The present disclosure also relates to the use of the crystalline forms of such a compound and compositions for the treatment and/or prevention of a diverse array of diseases, disorders and conditions mediated, in whole or in part, by CD73. CD73 inhibitors have been linked to the treatment of a diverse array of disorders, including cancer, fibrosis, neurological and neurodegenerative disorders (e.g., depression and Parkinson's disease), cerebral and cardiac ischemic diseases, immune-related disorders, and disorders with an inflammatory component. [See, e.g., Sorrentino et al (2013) OncoImmunol, 2:e22448, doi: 10.4161/onci.22448; and Regateiro et al. (2012) Clin. Exp. Immunol, 171:1-7]. In particular embodiments, the crystalline forms of the compound described herein can be formulated in a manner to inhibit the immunosuppressive activity and/or the anti-inflammatory activity of CD73, and are useful as therapeutic or prophylactic therapy when such inhibition is desired. Unless otherwise indicated, when uses refer to the compound (or to the crystalline form of the compound) described herein, it is to be understood that such compound may be in a form appropriate for delivery (e.g., a pharmaceutical composition).

In some embodiments, the present disclosure contemplates methods for treating or preventing cancer in a subject (e.g., a human) comprising administering to the subject a therapeutically effective amount of a crystalline form of a compound of Formula (I). The present disclosure includes methods of treating or preventing a cancer in a subject by administering to the subject a crystalline form of a compound of Formula (I) in an amount effective to reverse, stop or slow the progression of CD73-mediated immunosuppression.

Examples of the cancers that can be treated using the crystalline form of a compound of Formula (I) and compositions described herein include, but are not limited to: cancers of the prostate, such as metastatic castration resistant prostate cancer, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present disclosure, the cancer is melanoma, colon cancer, pancreatic cancer, breast cancer, prostate cancer, lung cancer, leukemia, a brain tumor, lymphoma, sarcoma, ovarian cancer, or Kaposi's sarcoma. Cancers that are candidates for treatment with a crystalline form of a compound of Formula (I) and compositions of the present disclosure are discussed further hereafter.

The present disclosure contemplates methods of treating a subject receiving a bone marrow transplant or peripheral blood stem cell transplant by administering a therapeutically effective amount of a crystalline form of a compound of Formula (I) sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, the present disclosure contemplates methods for treating or preventing an infective disorder (e.g., a viral infection) in a subject (e.g., a human) comprising administering to the subject a therapeutically effective amount of a crystalline form of a compound of Formula (I). In some embodiments, the infective disorder is a viral infection (e.g., a chronic viral infection), a bacterial infection, a fungal infection, or a parasitic infection. In certain embodiments, the viral infection is human immunodeficiency virus or cytomegalovirus.

In still other embodiments, the present disclosure contemplates methods for treating and/or preventing immune-related diseases, disorders and conditions; diseases having an inflammatory component; as well as disorders associated with the foregoing; with a crystalline form of a compound of Formula (I). Examples of immune-related diseases, disorders and conditions are described hereafter.

Other diseases, disorders and conditions that can be treated or prevented, in whole or in part, by modulation of CD73 activity are candidate indications for a crystalline form of a compound of Formula (I) as described herein.

The present disclosure further contemplates the use of the crystalline form of a compound of Formula (I) described herein in combination with one or more additional agents. The one or more additional agents may have some CD73-modulating activity and/or they may function through distinct mechanisms of action. In some embodiments, such agents comprise radiation (e.g., localized radiation therapy or total body radiation therapy) and/or other treatment modalities of a non-pharmacological nature. When combination therapy is utilized, the crystalline form of a compound of Formula (I) and the one additional agent(s) may be in the form of a single composition or multiple compositions, and the treatment modalities can be administered concurrently, sequentially, or through some other regimen. By way of example, the present disclosure contemplates a treatment regimen wherein a radiation phase is followed by a chemotherapeutic phase. The combination therapy can have an additive or synergistic effect. Other benefits of combination therapy are described hereafter.

BRIEF DESCRIPTION OF THE DRAWINGS

FIG. 12A shows the XRPD pattern of Form I reference, Form V starting material, Form II reference, and the material recovered from slurrying a mixture of Forms I, II and V in 100% EtOH at time 0, and after 1 day; and the material recovered from slurrying a mixture of Forms I, II and V in 80% Ethanol: 20% EtOAc at time 0, and after 1 day, and 2 days. FIG. 12B shows the XRPD pattern of Form I reference, Form V starting material, Form II reference, and the material recovered from slurrying a mixture of Forms I, II and V in 67% EtOH: 33% EtOAc at time 0, and after 1 day and 2 days; and the material recovered from slurrying a mixture of Forms I, II and V in 50% Ethanol: 50% EtOAc at time 0, and after 1 day. FIG. 12C shows the XRPD pattern of Form I reference, Form V starting material, Form II reference, and the material recovered from slurrying a mixture of Forms I, II and V in 33% EtOH: 67% EtOAc at time 0, and after 1 day and 2 days. FIG. 12D shows the XRPD pattern of Form I reference, Form V starting material, Form II reference, and the material recovered from slurrying a mixture of Forms I, II and V in 20% EtOH: 80% EtOAc at time 0, and after 2 days; and the material recovered from slurrying a mixture of Forms I, II and V in 100% EtOAc at time 0, and after 2 days.

DETAILED DESCRIPTION OF THE DISCLOSURE

Figure 1:
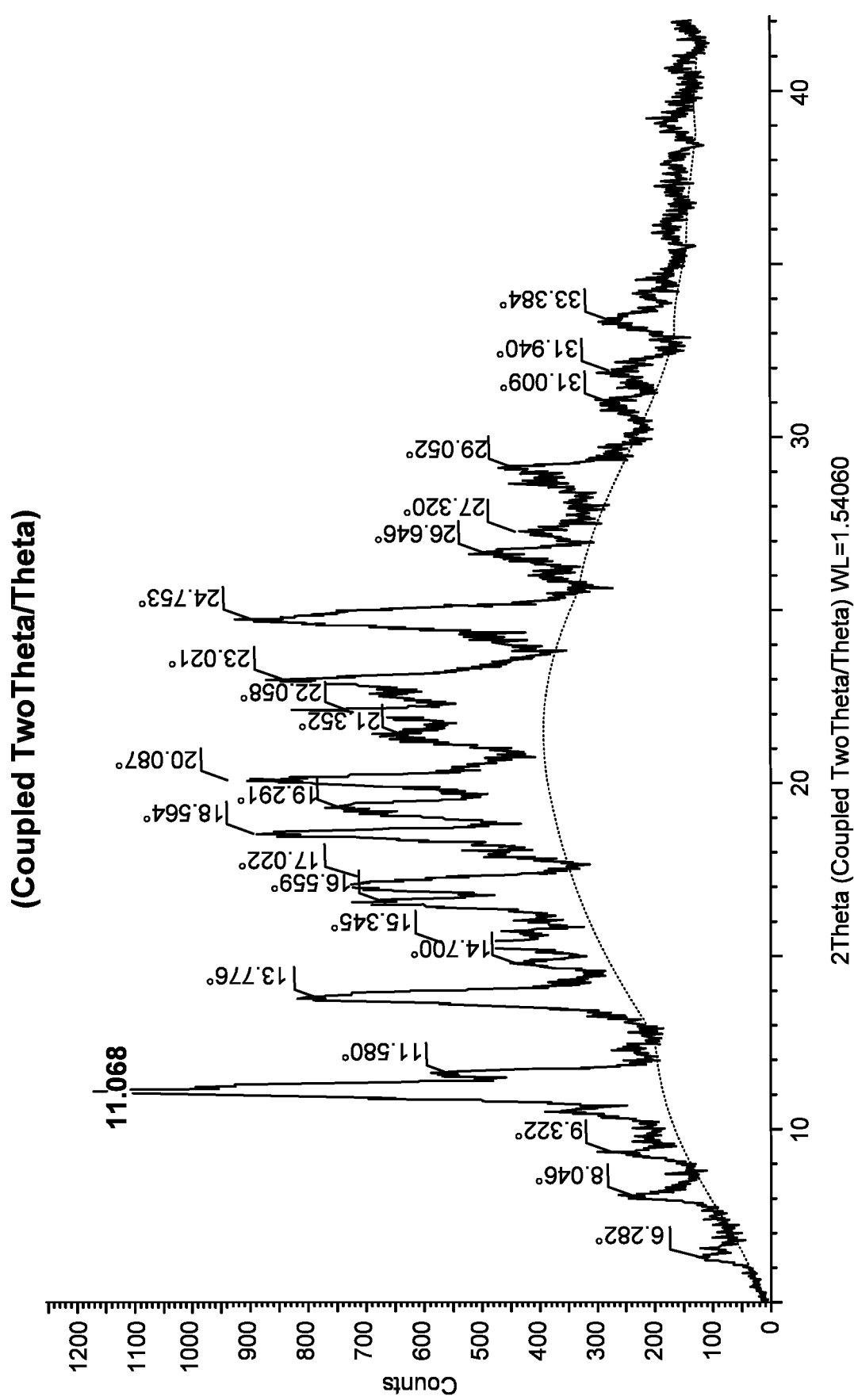
FIG. 1 shows an X-ray powder diffraction (XRPD) pattern of cystalline Form I of the compound of Formula (I).

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure. Unless defined otherwise, all technical and scientific terms used herein have the same meaning as commonly understood by one of ordinary skill in the art to which this disclosure belongs.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

As used herein, the term "a crystalline form of a compound of Formula (I)" refers to any of the crystalline forms of the noted compound as described herein. The crystalline form can be, however, formulated to a liquid, gel, or ointment, for example, for ease of administration to a subject. In particular, with reference to a method involving the administration of a crystalline form of a compound of Formula (I), the method is meant to include administration of a liquid formulation that is prepared using the crystalline form of a compound of Formula (I).

The publications discussed herein are provided solely for their disclosure prior to the filing date of the present application. Further, the dates of publication provided may be different from the actual publication dates, which may need to be independently confirmed.

I. General

The compound (((((2R,3S,4R,5R)-5-(6-chloro-4-(((S)-1-(2-fluorophenyl)ethyl)amino)-1H-pyrazolo[3,4-b]pyridin-1-yl)-3,4-dihydroxytetrahydrofuran-2-yl)methoxy)(hydroxy)phosphoryl)methyl)phosphonic acid, represented by Formula (I) is a potent inhibitor of CD73:

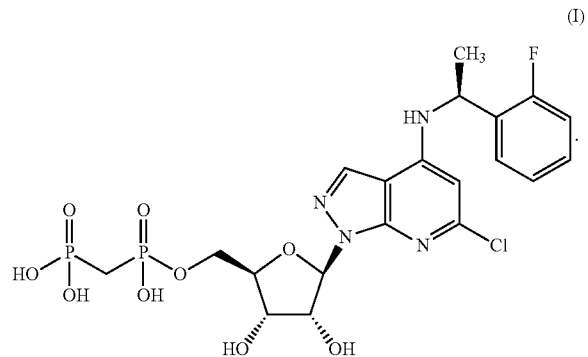 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

The present disclosure results from the surprising discoveries of the crystalline forms of the compound of Formula (I), advantages attributed to the forms as described herein, and processes for making the crystalline forms. Crystalline materials are generally more stable physically and chemically. The superior stability of crystalline material may make them more suitable to be used in the final dosage form as shelf life of the product is directly correlated with stability.

The manufacturing process of a compound may also play a role in selecting a desired polymorphic form. As one example, compounds that exhibit transient solubility due to the tendency of certain polymorphic forms to precipitate from solution can make maximizing the efficiency of a manufacturing protocol a challenge. In such cases, an understanding of the solubility profiles of the polymorphic forms of a compound can be important for process development. For example, the solubility profiles can inform decisions regarding solvent systems that can be utilized to solubilize all polymorphic forms of the desired compound such that purifying techniques, such as, for example, polishing filtration, can be conducted with minimal loss of the desired compound due to precipitation on the filter. Subsequent to such purifying techniques, the solubility profiles of the various polymorphic forms may inform decisions regarding techniques that are useful to precipitate the desired compound from solution such that the overall yield is maximized (i.e., controlling the solvent conditions to induce precipitation of the most stable polymorphic form under those conditions). Certain polymorphic forms may also have physical properties that allow for them to be handled more easily during the manufacturing process. For example, crystalline morphology (e.g., needles, plates or prisms) can influence the ease of filtration and drying protocols. Additional physical properties such as, for example, hygroscopicity, bulk density and flowability may provide certain benefits to the manufacturing process. Additionally, a crystallization step in active pharmaceutical ingredient (API) processing also provides an opportunity to enhance the drug substance purity by removing impurities (e.g., such as those in the processing solvent). Finally, certain polymorphic forms may be selected due to suitability for pharmaceutical applications, e.g., having a residual solvent content that is safe for patient administration (e.g., orally or parenterally).

II. Definitions

Unless otherwise indicated, the following terms are intended to have the meaning set forth below. Other terms are defined elsewhere throughout the specification.

"Alkyl" refers to a straight or branched, saturated, aliphatic radical having the number of carbon atoms indicated (i.e., $C_{1-4}$ means one to four carbons). Alkyl can include any number of carbons, such as $C_{1-2}$, $C_{1-3}$, $C_{1-4}$, $C_{2-3}$, and $C_{3-4}$. For example, $C_{1-4}$ alkyl includes, but is not limited to, methyl, ethyl, propyl, isopropyl, butyl, isobutyl, sec-butyl, tert-butyl.

"Hydrate" refers to a complex formed by the combining of the compound of Formula (I) and water. The term includes stoichiometric as well as non-stoichiometric hydrates.

"Solvate" refers to a complex formed by the combining of the compound of Formula (I) and a solvent. The term includes stoichiometric as well as non-stoichiometric solvates. Exemplary solvents that form solvates include, but are not limited to methanol, ethanol, isopropanol, DMSO, ethyl acetate, acetic acid, acetonitrile, and methyl tert-butyl ether. In some embodiments, the crystalline form of the compound of Formula (I) is an acetonitrile, ethanol, ethylacetate or methyl tert-butyl ether solvate.

"Desolvated" refers to a form of the compound of Formula (I) that is a solvate as described herein, and from which solvent molecules have been partially or completely removed. Desolvation techniques to produce desolvated forms include, without limitation, exposure of a Form (solvate) of the compound of Formula (I) to a vacuum, subjecting the solvate to elevated temperature, exposing the solvate to a stream of gas, such as air or nitrogen, washing or slurrying the solvate in a different solvent that has less propensity to bind, or any combination thereof. Thus, a desolvated form of the compound of Formula (I) can be completely without solvent molecules, or partially solvated wherein solvent molecules are present in stoichiometric or non-stoichiometric amounts.

"Alcohol" refers to a solvent having a hydroxy group. Representative alcohols can have any suitable number of carbon atoms, such as $C_1$-$C_6$, and any suitable number of hydroxy groups, such as 1-3. Exemplary alcohols include, but are not limited to, methanol, ethanol, n-propanol, i-propanol, etc.

"Crude" refers to a mixture including a desired compound (e.g., the compound of formula (I)) and at least one other species (e.g., a solvent, a reagent such as an acid or base, a starting material, or a byproduct of a reaction giving rise to the desired compound).

Suitable solvents described herein, refer to solvents characterized with high solubility of the compound of Formula (I) at a concentration of at least about 50 mg/mL at 55-60° C. Anti-solvents, are generally considered 'poor solvents', refer to solvents characterized with low solubility of the compound of Formula (I) at a concentration of less than about 50 mg/mL at 55-60° C. While anti-solvents may be poor for dissolving the compound, they can be well suited for crystallization purposes.

"Precipitating" refers to the process of causing a compound in a solution to coalesce into a solid form of the substance (i.e., a precipitate). The entirety of a compound in a solution, or any fraction thereof, can be caused to precipitate. The solid form of the substance can be amorphous or crystalline.

"Crystalline form" refers to a solid form of a compound wherein the constituent molecules are packed in a regularly ordered, repeating pattern. A crystalline form can include triclinic, monoclinic, orthorhombic, tetragonal, trigonal, hexagonal, and cubic crystal geometries. A crystalline form can include one or more regions, i.e., grains, with distinct crystal boundaries. A crystalline solid can include two or more crystal geometries.

"Amorphous form" refers to a solid form of a compound having no definite crystal structure, i.e., lacking a regularly ordered, repeating pattern of constituent molecules.

"Isolating" refers to the process of isolating at least a portion of a first substance (e.g., a precipitate) from a mixture including the substance and at least one additional substance. In some instances, the isolated substance is substantially free of at least one of the additional substances present in the original mixture.

"Substantially free" refers to an amount of 10% or less of another form or impurity, preferably 8%, 5%, 4%, 3%, 2%, 1%, 0.5%, or less of another form or impurity. Preferably, substantially free refers to a crystalline form of a compound of Formula (I) that contains less than 5% of other crystalline or amorphous forms of a compound of Formula (I). Preferably, substantially free refers to a crystalline form of a compound of Formula (I) that contains less than 1% of other crystalline or amorphous forms of a compound of Formula (I).

"About" means a range of values including the specified value, which a person of ordinary skill in the art would consider reasonably similar to the specified value. In some embodiments, the term "about" means within a standard deviation using measurements generally acceptable in the art. In some embodiments, "about" means a range extending to +1-10% of the specified value. In some embodiments, "about" means a range extending to +1-5% of the specified value. In some embodiments, "about" means a range extending to +1-2% of the specified value. In some embodiments, "about" means the specified value.

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), or carbon-14 ($^{14}$C), or non-radioactive isotopes, such as deuterium ($^2$H) or carbon-13 ($^{13}$C). Such isotopic of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present inventiondisclosure, whether radioactive or not, are intended to be encompassed within the scope of the present disclosure.

The terms "patient" or "subject" are used interchangeably to refer to a human or a non-human animal (e.g., a mammal).

The terms "treat", "treating", treatment" and the like refer to a course of action (such as administering an inhibitor of CD73 or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an CD73 inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an CD73 inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

"Substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

As used herein, the terms "CD73 inhibitor", "CD73 blocker", "adenosine by 5'-nucleotidase, ecto inhibitor", "NT5E inhibitor", "5NT inhibitor" and all other related art-accepted terms refer to a compound capable of modulating, either directly or indirectly, the CD73 receptor in an in vitro assay, an in vivo model, and/or other means indicative of therapeutic efficacy. The terms also refer to compounds that exhibit at least some therapeutic benefit in a human subject. An CD73 inhibitor may be a competitive, noncompetitive, or irreversible CD73 inhibitor. "A competitive CD73 inhibitor" is a compound that reversibly inhibits CD73 enzyme activity at the catalytic site; "a noncompetitive CD73 inhibitor" is a compound that reversibly inhibits CD73 enzyme activity at a non-catalytic site; and "an irreversible CD73 inhibitor" is a compound that irreversibly eliminates CD73 enzyme activity by forming a covalent bond (or other stable means of inhibiting enzyme function) with the enzyme.

III. Crystalline Forms

The present disclosure provides crystalline forms of (((((2R,3S,4R,5R)-5-(6-chloro-4-(((S)-1-(2-fluorophenyl)ethyl)amino)-1H-pyrazolo[3,4-b]pyridin-1-yl)-3,4-dihydroxytetrahydrofuran-2-yl)methoxy)(hydroxy)phosphoryl)methyl)phosphonic acid: represented by Formula (I), including solvate and hydrate forms.

In one aspect, the present disclosure provides a crystalline form of a compound having Formula (I):

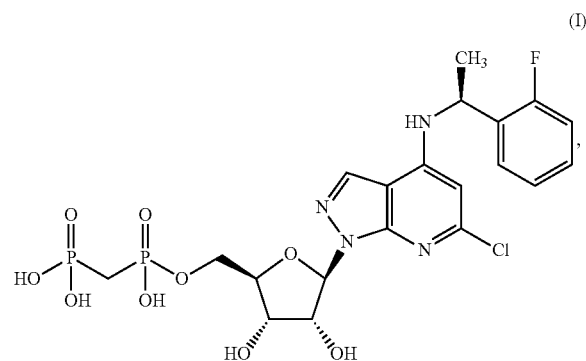 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

(I)

wherein the crystalline form is any one of crystalline Forms I to VI, each of which is characterized by an X-ray powder diffraction (XRPD) pattern as described herein.

Methods for collection of XRPD data are known in the art, and any such methods can be used for characterizing the crystalline forms of the compound of formula (I). For example, the X-ray powder diffraction patterns described herein can be generated using Cu Kα1 radiation.

In some embodiments, the crystalline form described herein is further characterized by a differential scanning calorimetry (DSC) thermogram.

In some embodiments, the crystalline form described herein is further characterized by a Nuclear Magnetic Resonance spectrum, such as a $^1$H NMR spectrum.

In some embodiments, the crystallize form described herein is further characterized by a dynamic vapor sorption (DVS) isotherm.

III-1. Crystalline Form I

In one embodiment, the present disclosure provides crystalline Form I of a compound of Formula (I), characterized by an X-ray powder diffraction (XRPD) pattern including three or more peaks at 11.1, 11.6, 13.8, 14.7, 15.4, 16.6, 17.0, 18.6, 19.3, 20.1, 21.3, 22.1, 23.0, 24.8, 26.6, 27.3, and 29.1 degrees 2θ (±0.2 degrees 2θ).

Crystalline Form I of the compound of Formula (I) can be characterized by an X-ray powder diffraction (XRPD) pattern having one or more, e.g., two, three, four, five, seven, or more, peaks at 11.1, 11.6, 13.8, 14.7, 15.4, 16.6, 17.0, 18.6, 19.3, 20.1, 21.3, 22.1, 23.0, 24.8, 26.6, 27.3, and 29.1 degrees 2θ (±0.2 degrees 2θ), wherein the XRPD is made using CuK$_{α1}$ radiation. In some embodiments, the crystalline Form I is characterized by an XRPD pattern including four or more peaks at 11.1, 11.6, 13.8, 14.7, 15.4, 16.6, 17.0, 18.6, 19.3, 20.1, 21.3, 22.1, 23.0, 24.8, 26.6, 27.3, and 29.1 degrees 2θ (±0.2 degrees 2θ). In some embodiments, the crystalline Form I is characterized by an XRPD pattern including five or more peaks at 11.1, 11.6, 13.8, 14.78, 15.4, 16.6, 17.0, 18.6, 19.3, 20.1, 21.3, 22.1, 23.0, 24.8, 26.6, 27.3, and 29.1 degrees 2θ (±0.2 degrees 2θ). In some embodiments, the crystalline Form I is characterized by an XRPD pattern including six or more peaks at 11.1, 11.6, 13.8, 14.78, 15.4, 16.6, 17.0, 18.6, 19.3, 20.1, 21.3, 22.1, 23.0, 24.8, 26.6, 27.3, and 29.1 degrees 2θ (±0.2 degrees 2θ). In some embodiments, the crystalline Form I is characterized by an XRPD pattern including seven or more peaks at 11.1, 11.6, 13.8, 14.78, 15.4, 16.6, 17.0, 18.6, 19.3, 20.1, 21.3, 22.1, 23.0, 24.8, 26.6, 27.3, and 29.1 degrees 2θ (±0.2 degrees 2θ).

In some embodiments, the crystalline Form I is characterized by an XRPD pattern including peaks at 11.1, 13.8, 18.6, 20.1, 23.0, and 24.8 degrees 2θ (±0.2 degrees 2θ). In some embodiments, the XRPD pattern further includes one or more peaks at 11.6, 14.7, 15.4, 16.6, 17.0, 19.3, 21.3, 22.1, 24.8, 26.6, 27.3, and 29.1 degrees 2θ (±0.2 degrees 2θ). In some embodiments, the XRPD pattern further includes two or more peaks at 11.6, 14.7, 15.4, 16.6, 17.0, 19.3, 21.3, 22.1, 24.8, 26.6, 27.3, and 29.1 degrees 2θ (±0.2 degrees 2θ). In some embodiments, the XRPD pattern further includes three or more peaks at 11.6, 14.7, 15.4, 16.6, 17.0, 19.3, 21.3, 22.1, 24.8, 26.6, 27.3, and 29.1 degrees 2θ (±0.2 degrees 2θ). In some embodiments, the XRPD pattern further includes four or more peaks at 11.6, 14.7, 15.4, 16.6, 17.0, 19.3, 21.3, 22.1, 24.8, 26.6, 27.3, and 29.1 degrees 2θ (±0.2 degrees 2θ). In some embodiments, the XRPD pattern further includes five or more peaks at 11.6, 14.7, 15.4, 16.6, 17.0, 19.3, 21.3, 22.1, 24.8, 26.6, 27.3, and 29.1 degrees 2θ (±0.2 degrees 2θ).

In some embodiments, the crystalline Form I is characterized by an XRPD pattern including peaks at 11.1, 11.6, 13.8, 14.7, 15.4, 16.6, 17.0, 18.6, 19.3, 20.1, 21.3, 22.1, 23.0, 24.8, 26.6, 27.3, and 29.1 degrees 2θ (±0.2 degrees 2θ). In some embodiments, the crystalline Form I is characterized by an XRPD pattern including peaks at 6.3, 8.0, 9.3, 11.1, 11.6, 13.8, 14.7, 15.4, 16.6, 17.0, 18.6, 19.3, 20.1, 21.3, 22.1, 23.0, 24.8, 26.6, 27.3, 29.1, 31.0, 31.9, and 33.4 degrees 2θ (±0.2 degrees 2θ).

In some embodiments, the crystalline Form I is characterized by an XRPD pattern substantially in accordance with FIG. 1.

In some embodiments, crystalline Form I is substantially free of other crystalline or amorphous forms of the compound of Formula (I).

In some embodiments, the crystalline Form I is characterized by a differential scanning calorimetry (DSC) thermogram including an endotherm at from about 155° C. to about 167° C. In some embodiments, the crystalline Form I is further characterized by a differential scanning calorimetry (DSC) thermogram including an endothermic peak at about 163.9° C. In some embodiments, the differential scanning calorimetry (DSC) thermogram further includes an exotherm at from about 167 to about 210° C. In some embodiments, the differential scanning calorimetry (DSC) thermogram is characterized by an exothermic peak at about 176.1° C. In some embodiments, the crystalline Form I is further characterized by a melting point of about 163.9° C. as determined by a differential scanning calorimetry thermogram (DSC). In some embodiments, the crystalline Form I is further characterized by a melting point onset of about 155.1° C. as determined by a differential scanning calorimetry thermogram (DSC).

Figure 2:
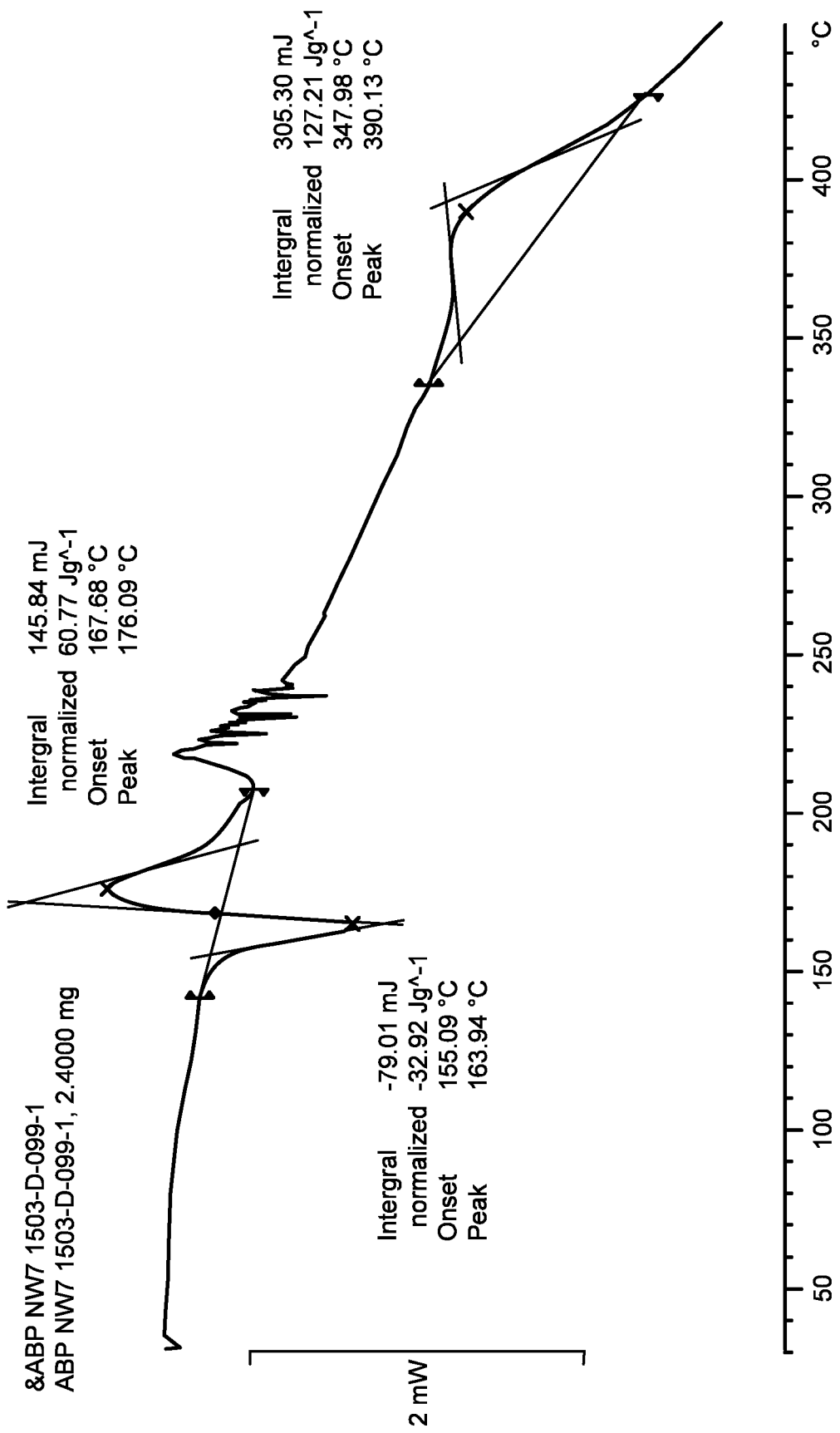
FIG. 2 shows a differential scanning calorimetry (DSC) plot of cystalline Form I of the compound of Formula (I).

In some embodiments, the crystalline Form I is further characterized by a differential scanning calorimetry (DSC) thermogram substantially in accordance with FIG. 2.

In some embodiments, the crystalline Form I is characterized by an XRPD pattern substantially in accordance with FIG. 1; and is further characterized by a differential scanning calorimetry (DSC) thermogram substantially in accordance with FIG. 2.

A $^1$H NMR spectrum of the crystalline Form I can be used to determine the content of one or more residual solvents (e.g., ethanol and/or toluene). In some embodiments, the crystalline Form I has ethanol in an amount of 0.04% by weight, as determined by a $^1$H NMR spectrum. In some embodiments, the crystalline Form I is substantially free of toluene, as determined by a $^1$H NMR spectrum.

In some embodiments, the crystalline Form I is characterized by a DVS isotherm characterized by a change in mass of between 0.5% and 6.5% at between 40% RH and 70% RH. In some embodiments, the crystalline Form I is characterized by a DVS isotherm characterized by a change in mass of between 2% and 5% between 50% RH and 60% RH. In some embodiments, the crystalline Form I is characterized by a DVS isotherm substantially in accordance with FIG. 16.

III-2. Crystalline Form II

In one embodiment, the present disclosure provides crystalline Form II of a compound of Formula (I), characterized by an X-ray powder diffraction (XRPD) pattern including three or more peaks at 10.1, 10.8, 12.8, 13.7, 16.5, 17.7, 19.0, 22.8, and 24.6 degrees 2θ (±0.2 degrees 2θ).

Crystalline Form II of the compound of Formula (I) can be characterized by an X-ray powder diffraction (XRPD) pattern having one or more, e.g., two, three, four, five, seven, or more, peaks at 10.1, 10.8, 12.8, 13.7, 16.5, 17.7, 19.0, 22.8, and 24.6 degrees 2θ (±0.2 degrees 2θ), wherein the XRPD is made using CuK$_{\alpha 1}$ radiation. In some embodiments, the crystalline Form II of the compound of Formula (I) is characterized by an XRPD pattern including four or more peaks at 10.1, 10.8, 12.8, 13.7, 16.5, 17.7, 19.0, 22.8, and 24.6 degrees 2θ (±0.2 degrees 2θ). In some embodiments, the crystalline Form II of the compound of Formula (I) is characterized by an XRPD pattern including five or more peaks at 10.1, 10.8, 12.8, 13.7, 16.5, 17.7, 19.0, 22.8, and 24.6 degrees 2θ (±0.2 degrees 2θ). In some embodiments, the crystalline Form II of the compound of Formula (I) is characterized by an XRPD pattern including six or more peaks at 10.1, 10.8, 12.8, 13.7, 16.5, 17.7, 19.0, 22.8, and 24.6 degrees 2θ (±0.2 degrees 2θ). In some embodiments, the crystalline Form II of the compound of Formula (I) is characterized by an XRPD pattern including seven or more peaks at 10.1, 10.8, 12.8, 13.7, 16.5, 17.7, 19.0, 22.8, and 24.6 degrees 2θ (±0.2 degrees 2θ).

In some embodiments, the crystalline Form II of the compound of Formula (I) is characterized by an XRPD pattern including a peak at 16.5 degrees 2θ (±0.2 degrees 2θ). In some embodiments, the crystalline Form II of the compound of Formula (I) is characterized by an XRPD pattern including peaks at 16.5, 22.8, and 24.6 degrees 2θ (±0.2 degrees 2θ). In some embodiments, the XRPD pattern further includes one or more peaks at 10.1, 10.8, 12.8, 13.7, 17.7, and 19.0 degrees 2θ (±0.2 degrees 2θ). In some embodiments, the XRPD pattern further includes two or more peaks at 10.1, 10.8, 12.8, 13.7, 17.7, and 19.0 degrees 2θ (±0.2 degrees 2θ). In some embodiments, the XRPD pattern further includes three or more peaks at 10.1, 10.8, 12.8, 13.7, 17.7, and 19.0 degrees 2θ (±0.2 degrees 2θ). In some embodiments, the XRPD pattern further includes four or more peaks at 10.1, 10.8, 12.8, 13.7, 17.7, and 19.0 degrees 2θ (±0.2 degrees 2θ). In some embodiments, the XRPD pattern further includes five or more peaks at 10.1, 10.8, 12.8, 13.7, 17.7, and 19.0 degrees 2θ (±0.2 degrees 2θ).

In some embodiments, the crystalline Form II is characterized by an XRPD pattern including peaks at 10.1, 10.8, 12.8, 13.7, 16.5, 17.7, 19.0, 22.8, and 24.6 degrees 2θ (±0.2 degrees 2θ).

Figure 3:
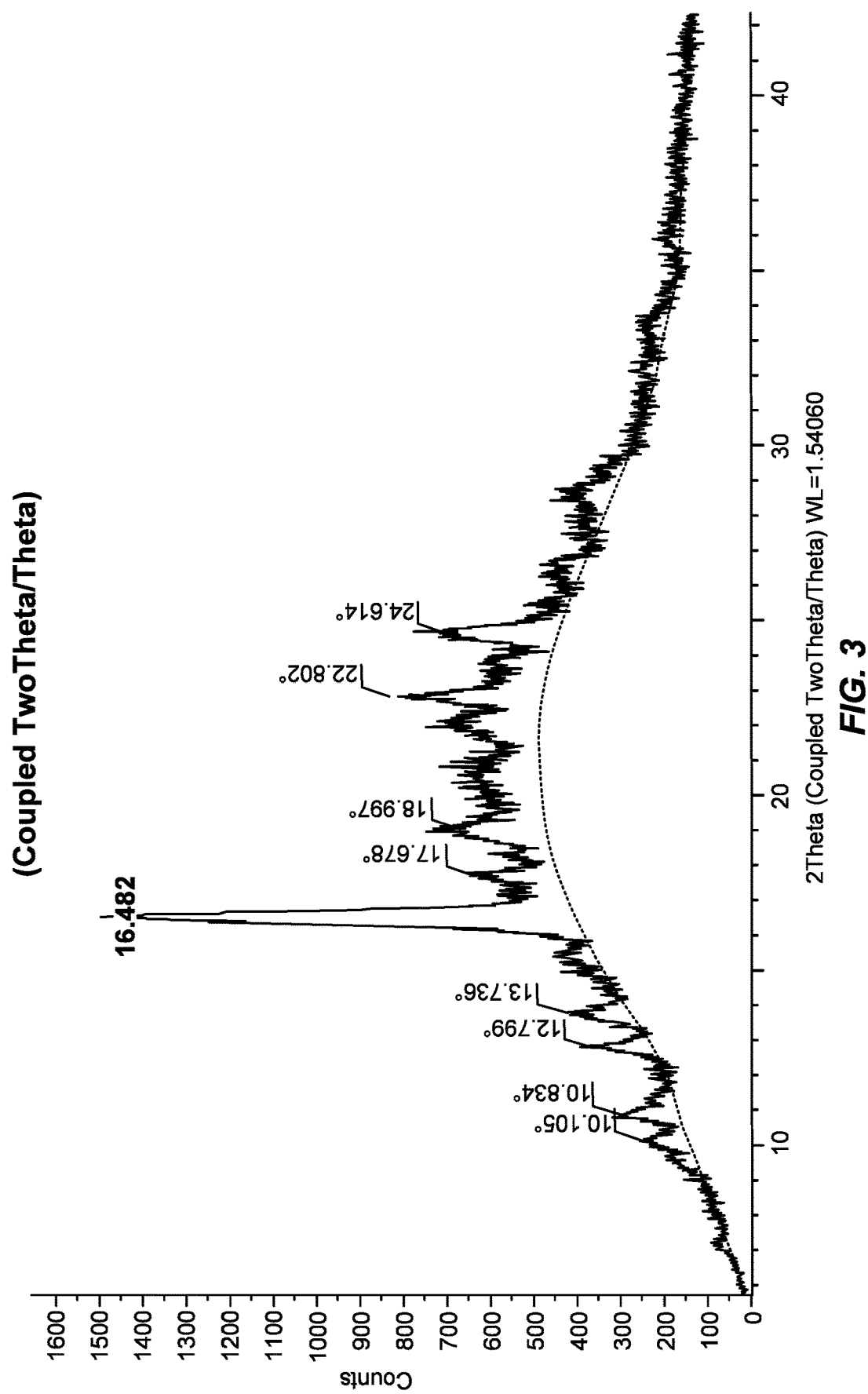
FIG. 3 shows an X-ray powder diffraction (XRPD) pattern of cystalline Form II of the compound of Formula (I).

In some embodiments, the crystalline Form II is characterized by an XRPD pattern substantially in accordance with FIG. 3.

In some embodiments, the crystalline Form II is substantially free of other crystalline or amorphous forms of a compound of Formula (I).

In some embodiments, the crystalline Form II is characterized by a differential scanning calorimetry (DSC) thermogram including an endotherm at from about 156° C. to about 171° C. In some embodiments, the crystalline Form II is further characterized by a differential scanning calorimetry (DSC) thermogram including an endothermic peak at about 166.5° C. In some embodiments, the differential scanning calorimetry (DSC) thermogram further includes an exotherm at from about 170° C. to about 210° C. In some embodiments, the differential scanning calorimetry (DSC) thermogram is characterized by an exothermic peak at about 179.3° C. In some embodiments, the crystalline Form II is further characterized by a melting point of about 166.5° C. as determined by a differential scanning calorimetry thermogram (DSC). In some embodiments, the crystalline Form II is further characterized by a melting point onset of about 157.4° C. as determined by a differential scanning calorimetry thermogram (DSC).

Figure 4:
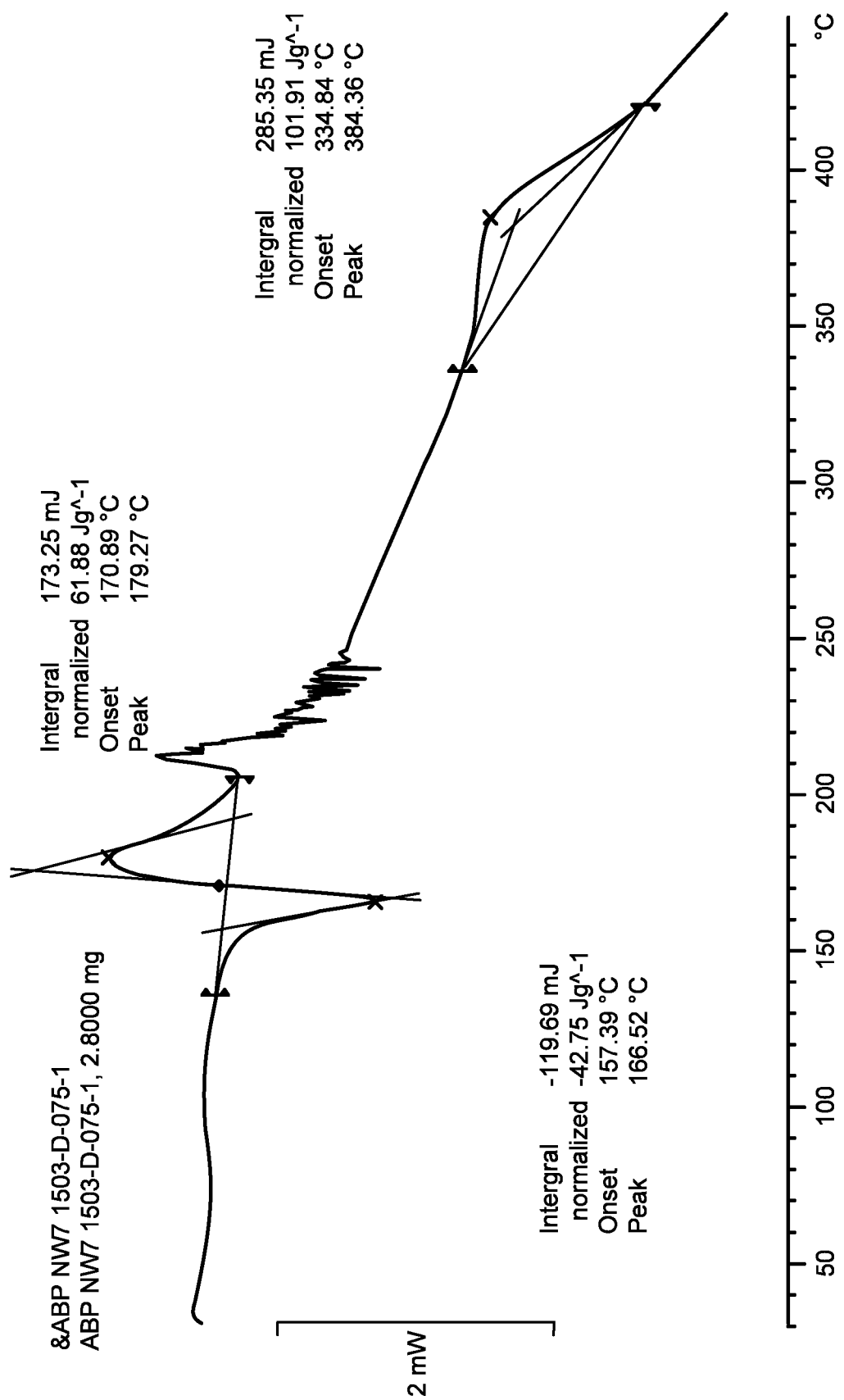
FIG. 4 shows a differential scanning calorimetry (DSC) plot of cystalline Form II of the compound of Formula (I).

In some embodiments, the crystalline Form II is further characterized by a differential scanning calorimetry (DSC) thermogram substantially in accordance with FIG. 4.

In some embodiments, the crystalline Form II is characterized by an XRPD pattern substantially in accordance with FIG. 3; and is further characterized by a differential scanning calorimetry (DSC) thermogram substantially in accordance with FIG. 4.

A $^1$H NMR spectrum of the crystalline Form II can be used to determine the content of one or more residual solvents (e.g., ethanol). In some embodiments, the crystalline Form II has ethanol in an amount of 0.68% by weight, as determined by a $^1$H NMR spectrum.

In some embodiments, the crystalline Form II is characterized by a DVS isotherm characterized by a change in mass of between 1% and 4% at between 40% RH and 70% RH. In some embodiments, the crystalline Form II is characterized by a DVS isotherm characterized by a change in mass of between 1.5% and 3.5% between 40% RH and 70% RH. In some embodiments, the crystalline Form II is characterized by a DVS isotherm substantially in accordance with FIG. 17.

III-3. Crystalline Form III

In one embodiment, the present disclosure provides crystalline Form III of a compound of Formula (I), characterized by an X-ray powder diffraction (XRPD) pattern including three or more peaks at 6.6, 10.9, 14.2, 16.1, 18.4, 19.3, 20.2, 22.0, 24.7, and 28.1 degrees 2θ (±0.2 degrees 2θ).

Crystalline Form III of the compound of Formula (I) can be characterized by an X-ray powder diffraction (XRPD) pattern having one or more, e.g., two, three, four, five, or more, peaks at 6.6, 10.9, 14.2, 16.1, 18.4, 19.3, 20.2, 22.0, 24.7, and 28.1 degrees 2θ (±0.2 degrees 2θ), wherein the XRPD is made using $CuK_{\alpha 1}$ radiation. In some embodiments, the crystalline Form III of the compound of Formula (I) is characterized by an XRPD pattern including four or more peaks at 6.6, 10.9, 14.2, 16.1, 18.4, 19.3, 20.2, 22.0, 24.7, and 28.1 degrees 2θ (±0.2 degrees 2θ). In some embodiments, the crystalline Form III of the compound of Formula (I) is characterized by an XRPD pattern including five or more peaks at 6.6, 10.9, 14.2, 16.1, 18.4, 19.3, 20.2, 22.0, 24.7, and 28.1 degrees 2θ (±0.2 degrees 2θ). In some embodiments, the crystalline Form III of the compound of Formula (I) is characterized by an XRPD pattern including six or more peaks at 6.6, 10.9, 14.2, 16.1, 18.4, 19.3, 20.2, 22.0, 24.7, and 28.1 degrees 2θ (±0.2 degrees 2θ). In some embodiments, the crystalline Form III of the compound of Formula (I) is characterized by an XRPD pattern including seven or more peaks at 6.6, 10.9, 14.2, 16.1, 18.4, 19.3, 20.2, 22.0, 24.7, and 28.1 degrees 2θ (±0.2 degrees 2θ).

In some embodiments, the crystalline Form III of the compound of Formula (I) is characterized by an XRPD pattern including peaks at 6.6, 10.9, 14.2, 16.1, 18.4, and 19.3 degrees 2θ (±0.2 degrees 2θ). In some embodiments, the XRPD pattern further includes one or more peaks at 20.2, 22.0, 24.7, and 28.1 degrees 2θ (±0.2 degrees 2θ). In some embodiments, the XRPD pattern further includes two or more peaks at 20.2, 22.0, 24.7, and 28.1 degrees 2θ (±0.2 degrees 2θ). In some embodiments, the XRPD pattern further includes three or more peaks at 20.2, 22.0, 24.7, and 28.1 degrees 2θ (±0.2 degrees 2θ). In some embodiments, the XRPD pattern further includes four peaks at 20.2, 22.0, 24.7, and 28.1 degrees 2θ (±0.2 degrees 2θ). In some embodiments, the XRPD pattern further includes peaks at 29.7, 32.0, and 33.5 degrees 2θ (±0.2 degrees 2θ).

In some embodiments, the crystalline Form III is characterized by an XRPD pattern including peaks at 6.6, 10.9, 14.2, 16.1, 18.4, 19.3, 20.2, 22.0, 24.7, and 28.1 degrees 2θ (±0.2 degrees 2θ). In some embodiments, the crystalline Form III is characterized by an XRPD pattern including peaks at 6.6, 10.9, 14.2, 16.1, 18.4, 19.3, 20.2, 22.0, 24.7, 28.1, 29.7, 32.0, and 33.5 degrees 2θ (±0.2 degrees 2θ).

Figure 5:
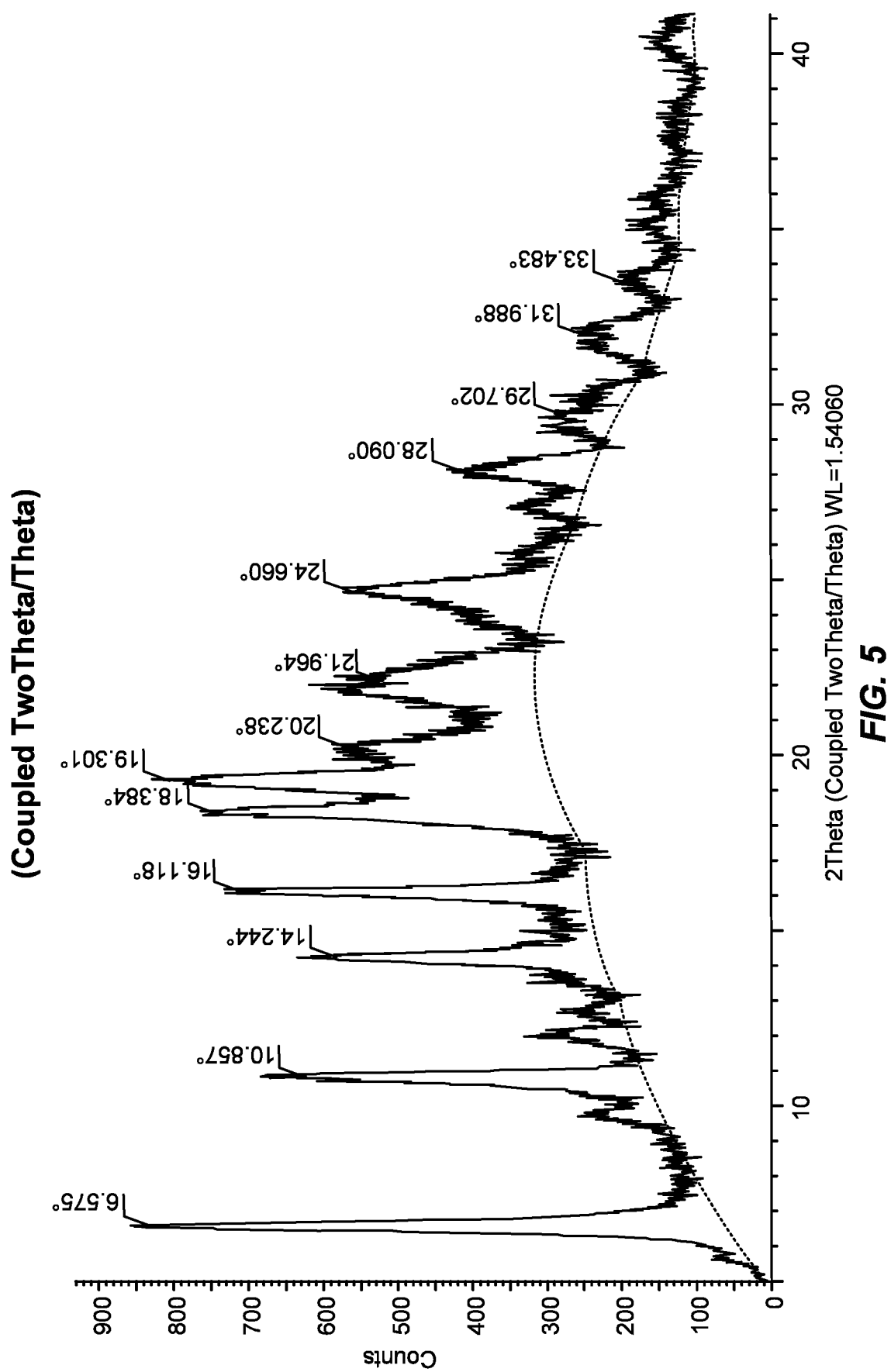
FIG. 5 shows an X-ray powder diffraction (XRPD) pattern of cystalline Form III of the compound of Formula (I).

In some embodiments, the crystalline Form III is characterized by an XRPD pattern substantially in accordance with FIG. 5.

In some embodiments, the crystalline Form III is substantially free of other crystalline or amorphous forms of a compound of Formula (I).

In some embodiments, the crystalline Form III is characterized by a differential scanning calorimetry (DSC) thermogram including an endotherm at from about 149° C. to about 183° C. In some embodiments, the crystalline Form III is further characterized by a differential scanning calorimetry (DSC) thermogram including an endothermic peak at about 161.8° C. In some embodiments, the differential scanning calorimetry (DSC) thermogram further includes an exotherm at from about 183 to about 210° C. In some embodiments, the differential scanning calorimetry (DSC) thermogram is characterized by an exothermic peak at about 188.2° C. In some embodiments, the crystalline Form III is further characterized by a melting point of about 161.8° C. as determined by a differential scanning calorimetry thermogram (DSC). In some embodiments, the crystalline Form III is further characterized by a melting point onset of about 149.6° C. as determined by a differential scanning calorimetry thermogram (DSC).

Figure 6:
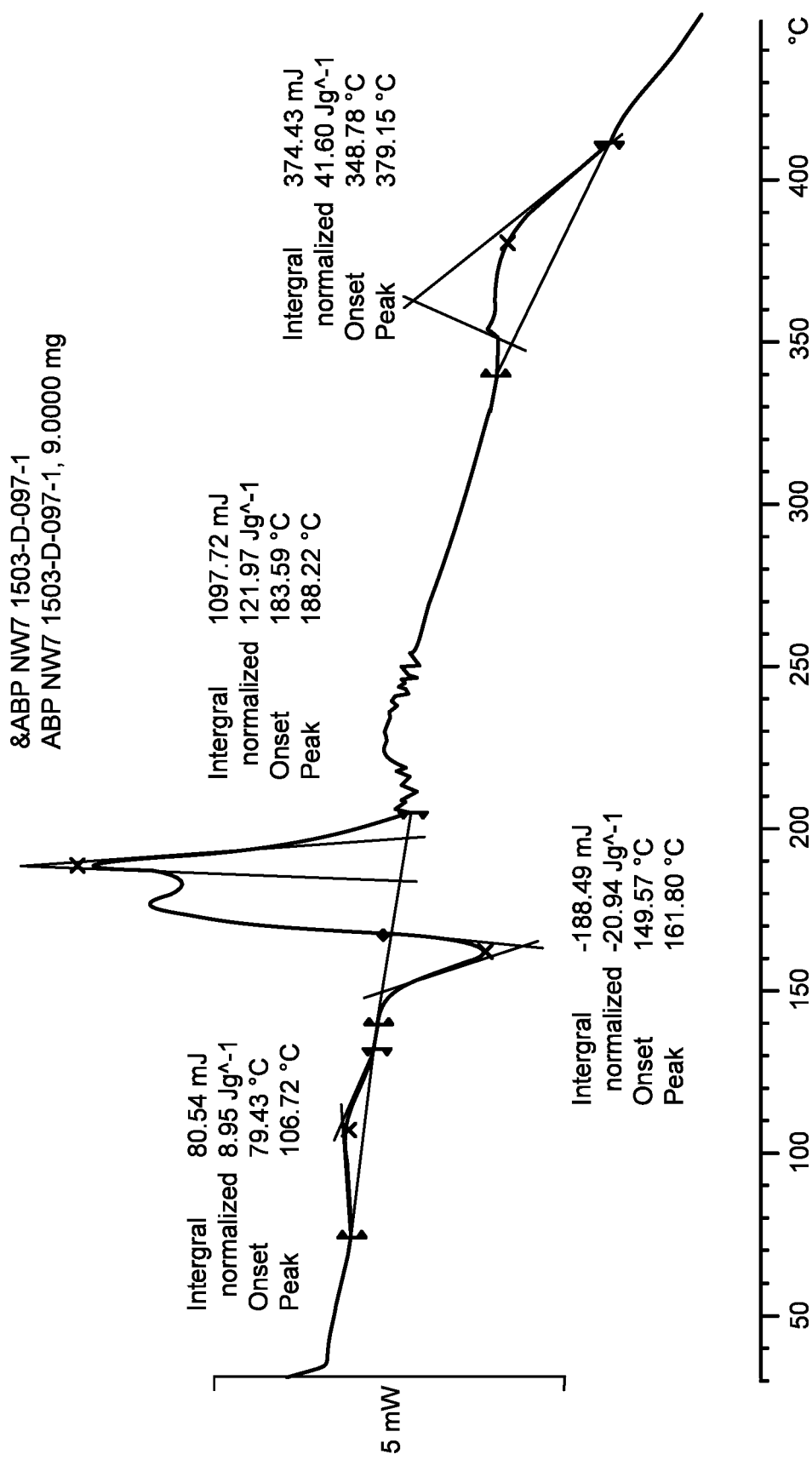
FIG. 6 shows a differential scanning calorimetry (DSC) plot of cystalline Form III of the compound of Formula (I).

In some embodiments, the crystalline Form III is further characterized by a differential scanning calorimetry (DSC) thermogram substantially in accordance with FIG. 6.

In some embodiments, the crystalline Form III is characterized by an XRPD pattern substantially in accordance with FIG. 5; and is further characterized by a differential scanning calorimetry (DSC) thermogram substantially in accordance with FIG. 6.

A $^1H$ NMR spectrum of the crystalline Form III can be used to determine the content of one or more residual solvents (e.g., ethanol and/or methyl tert-butyl ether). In some embodiments, the crystalline Form III is substantially free of ethanol, as determined by a $^1H$ NMR spectrum. In some embodiments, the crystalline Form III has methyl tert-butyl ether in an amount of 0.40% by weight, as determined by a $^1H$ NMR spectrum.

III-4. Crystalline Form IV

In one embodiment, the present disclosure provides crystalline Form IV of a compound of Formula (I), characterized by an X-ray powder diffraction (XRPD) pattern including three or more peaks at 6.0, 11.2, 14.1, 17.0, 19.5, 23.2, 25.1, 27.1, and 28.9 degrees 2θ (±0.2 degrees 2θ).

Crystalline Form IV of the compound of Formula (I) can be characterized by an X-ray powder diffraction (XRPD) pattern having one or more, e.g., two, three, four, five, or more, peaks at 6.0, 11.2, 14.1, 17.0, 19.5, 23.2, 25.1, 27.1, and 28.9 degrees 2θ (±0.2 degrees 2θ), wherein the XRPD is made using $CuK_{\alpha 1}$ radiation. In some embodiments, the crystalline Form IV of the compound of Formula (I) is characterized by an XRPD pattern including four or more peaks at 6.0, 11.2, 14.1, 17.0, 19.5, 23.2, 25.1, 27.1, and 28.9 degrees 2θ (±0.2 degrees 2θ). In some embodiments, the crystalline Form IV of the compound of Formula (I) is characterized by an XRPD pattern including five or more peaks at 6.0, 11.2, 14.1, 17.0, 19.5, 23.2, 25.1, 27.1, and 28.9 degrees 2θ (±0.2 degrees 2θ). In some embodiments, the crystalline Form IV of the compound of Formula (I) is characterized by an XRPD pattern including six or more peaks at 6.0, 11.2, 14.1, 17.0, 19.5, 23.2, 25.1, 27.1, and 28.9 degrees 2θ (±0.2 degrees 2θ). In some embodiments, the crystalline Form IV of the compound of Formula (I) is characterized by an XRPD pattern including seven or more peaks at 6.0, 11.2, 14.1, 17.0, 19.5, 23.2, 25.1, 27.1, and 28.9 degrees 2θ (±0.2 degrees 2θ).

In some embodiments, the crystalline Form IV of the compound of Formula (I) is characterized by an XRPD pattern including peaks at 14.1, 17.0, 19.5, 23.2, and 25.1 degrees 2θ (±0.2 degrees 2θ). In some embodiments, the XRPD pattern further includes one or more peaks at 6.0, 11.2, 27.1, and 28.9 degrees 2θ (±0.2 degrees 2θ). In some embodiments, the XRPD pattern further includes two or more peaks at 6.0, 11.2, 27.1, and 28.9 degrees 2θ (±0.2 degrees 2θ). In some embodiments, the XRPD pattern further includes three or more peaks at 6.0, 11.2, 27.1, and 28.9 degrees 2θ (±0.2 degrees 2θ). In some embodiments, the XRPD pattern further includes four peaks at 6.0, 11.2, 27.1, and 28.9 degrees 2θ (±0.2 degrees 2θ).

In some embodiments, the crystalline Form IV is characterized by an XRPD pattern including peaks at 6.0, 11.2, 14.1, 17.0, 19.5, 23.2, 25.1, 27.1, and 28.9 degrees 2θ (±0.2 degrees 2θ).

Figure 7:
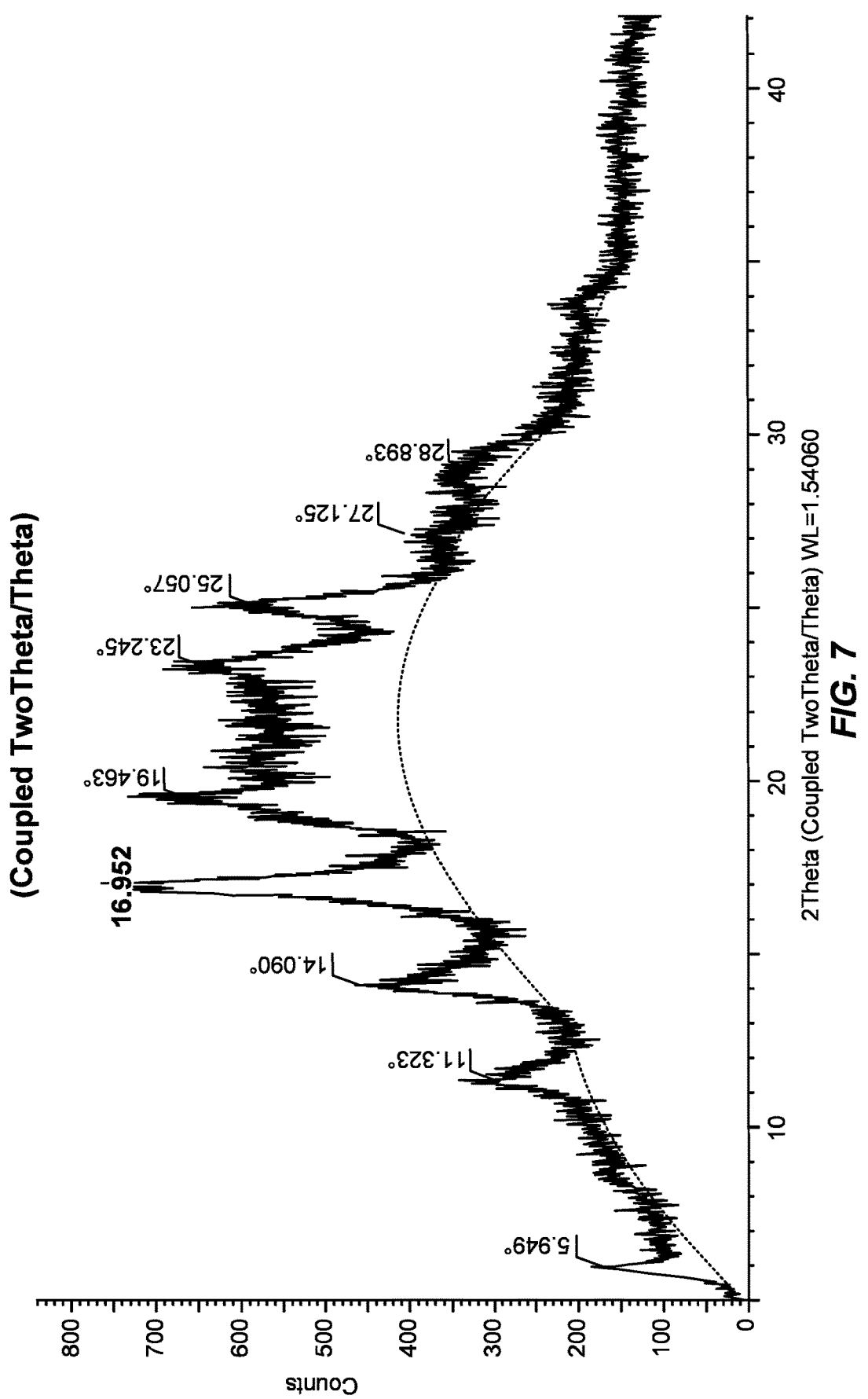
FIG. 7 shows an X-ray powder diffraction (XRPD) pattern of cystalline Form IV of the compound of Formula (I).

In some embodiments, the crystalline Form IV is characterized by an XRPD pattern substantially in accordance with FIG. 7.

In some embodiments, the crystalline Form IV is substantially free of other crystalline or amorphous forms of a compound of Formula (I).

A $^1$H NMR spectrum of the crystalline Form IV can be used to determine the content of one or more residual solvents (e.g., THF and/or ethyl acetate). In some embodiments, the crystalline Form IV has a content of THF in an amount of 0.05%, as determined by a $^1$H NMR spectrum. In some embodiments, the crystalline Form IV has ethyl acetate in an amount of 0.38% by weight, as determined by a $^1$H NMR spectrum.

III-5. Crystalline Form V

In one embodiment, the present disclosure provides crystalline Form V of a compound of Formula (I), characterized by an X-ray powder diffraction (XRPD) pattern including three or more peaks at 10.4, 15.1, 15.8, 16.3, 16.8, 18.5, 19.1, 19.7, 21.7, 22.1, 23.0, 23.5, 26.0, 26.5, 28.4, 28.9, and 31.4 degrees 2θ (±0.2 degrees 2θ).

Crystalline Form V of the compound of Formula (I) can be characterized by an X-ray powder diffraction (XRPD) pattern having one or more, e.g., two, three, four, five, or more, peaks at 10.4, 15.1, 15.8, 16.3, 16.8, 18.5, 19.1, 19.7, 21.7, 22.1, 23.0, 23.6, 26.0, 26.5, 28.4, 28.9, and 31.4 degrees 2θ (±0.2 degrees 2θ), wherein the XRPD is made using CuK$_{\alpha 1}$ radiation. In some embodiments, the crystalline Form V of the compound of Formula (I) is characterized by an XRPD pattern including four or more peaks at 10.4, 15.1, 15.8, 16.3, 16.8, 18.5, 19.1, 19.7, 21.7, 22.1, 23.0, 23.6, 26.0, 26.5, 28.4, 28.9, and 31.4 degrees 2θ (±0.2 degrees 2θ). In some embodiments, the crystalline Form V of the compound of Formula (I) is characterized by an XRPD pattern including five or more peaks at 10.4, 15.1, 15.8, 16.3, 16.8, 18.5, 19.1, 19.7, 21.7, 22.1, 23.0, 23.6, 26.0, 26.5, 28.4, 28.9, and 31.4 degrees 2θ (±0.2 degrees 2θ). In some embodiments, the crystalline Form V of the compound of Formula (I) is characterized by an XRPD pattern including six or more peaks at 10.4, 15.1, 15.8, 16.3, 16.8, 18.5, 19.1, 19.7, 21.7, 22.1, 23.0, 23.6, 26.0, 26.5, 28.4, 28.9, and 31.4 degrees 2θ (±0.2 degrees 2θ). In some embodiments, the crystalline Form V of the compound of Formula (I) is characterized by an XRPD pattern including seven or more peaks at 10.4, 15.1, 15.8, 16.3, 16.8, 18.5, 19.1, 19.7, 21.7, 22.1, 23.0, 23.6, 26.0, 26.5, 28.4, 28.9, and 31.4 degrees 2θ (±0.2 degrees 2θ).

In some embodiments, the crystalline Form V of the compound of Formula (I) is characterized by an XRPD pattern including peaks at 15.8, 16.3, 16.8, 18.5, 19.1, 21.7, 22.1, and 23.0 degrees 2θ (±0.2 degrees 2θ). In some embodiments, the XRPD pattern further includes one or more peaks at 10.4, 15.1, 19.7, and 23.6 degrees 2θ (±0.2 degrees 2θ). In some embodiments, the XRPD pattern further includes two or more peaks at 10.4, 15.1, 19.7, 23.6 degrees 2θ (±0.2 degrees 2θ). In some embodiments, the XRPD pattern further includes three or more peaks at 10.4, 15.1, 19.7, 23.6 degrees 2θ (±0.2 degrees 2θ). In some embodiments, the XRPD pattern further includes four peaks at 10.4, 15.1, 19.7, 23.6 degrees 2θ (±0.2 degrees 2θ).

In some embodiments, the crystalline Form V is characterized by an XRPD pattern including peaks at 10.4, 15.1, 15.8, 16.3, 16.8, 18.5, 19.1, 19.7, 21.7, 22.1, 23.0, and 23.6 degrees 2θ (±0.2 degrees 2θ).

Figure 8:
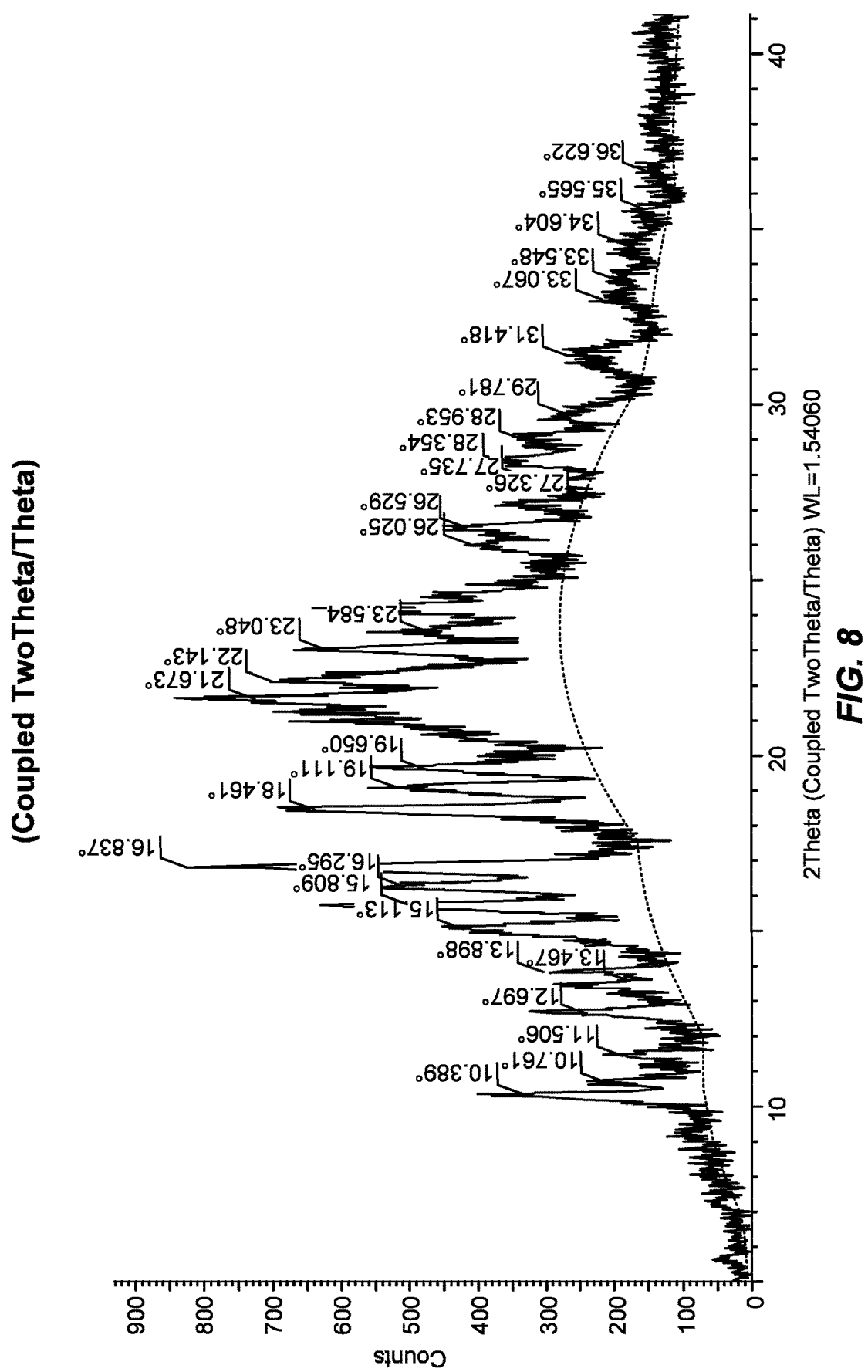
FIG. 8 shows an X-ray powder diffraction (XRPD) pattern of cystalline Form V of the compound of Formula (I).

In some embodiments, the crystalline Form V is characterized by an XRPD pattern substantially in accordance with FIG. 8.

In some embodiments, the crystalline Form V is substantially free of other crystalline or amorphous forms of a compound of Formula (I).

In some embodiments, the crystalline Form V is characterized by a differential scanning calorimetry (DSC) thermogram including an endotherm at from about 135° C. to about 172° C. In some embodiments, the crystalline Form V is further characterized by a differential scanning calorimetry (DSC) thermogram including an endothermic peak at about 150.4° C. In some embodiments, the differential scanning calorimetry (DSC) thermogram further includes an exotherm at from about 171 to about 210° C. In some embodiments, the differential scanning calorimetry (DSC) thermogram is characterized by an exothermic peak at about 177.8° C. In some embodiments, the crystalline Form V is further characterized by a melting point of about 150.4° C. as determined by a differential scanning calorimetry thermogram (DSC). In some embodiments, the crystalline Form V is further characterized by a melting point onset of about 135.8° C. as determined by a differential scanning calorimetry thermogram (DSC).

Figure 9:
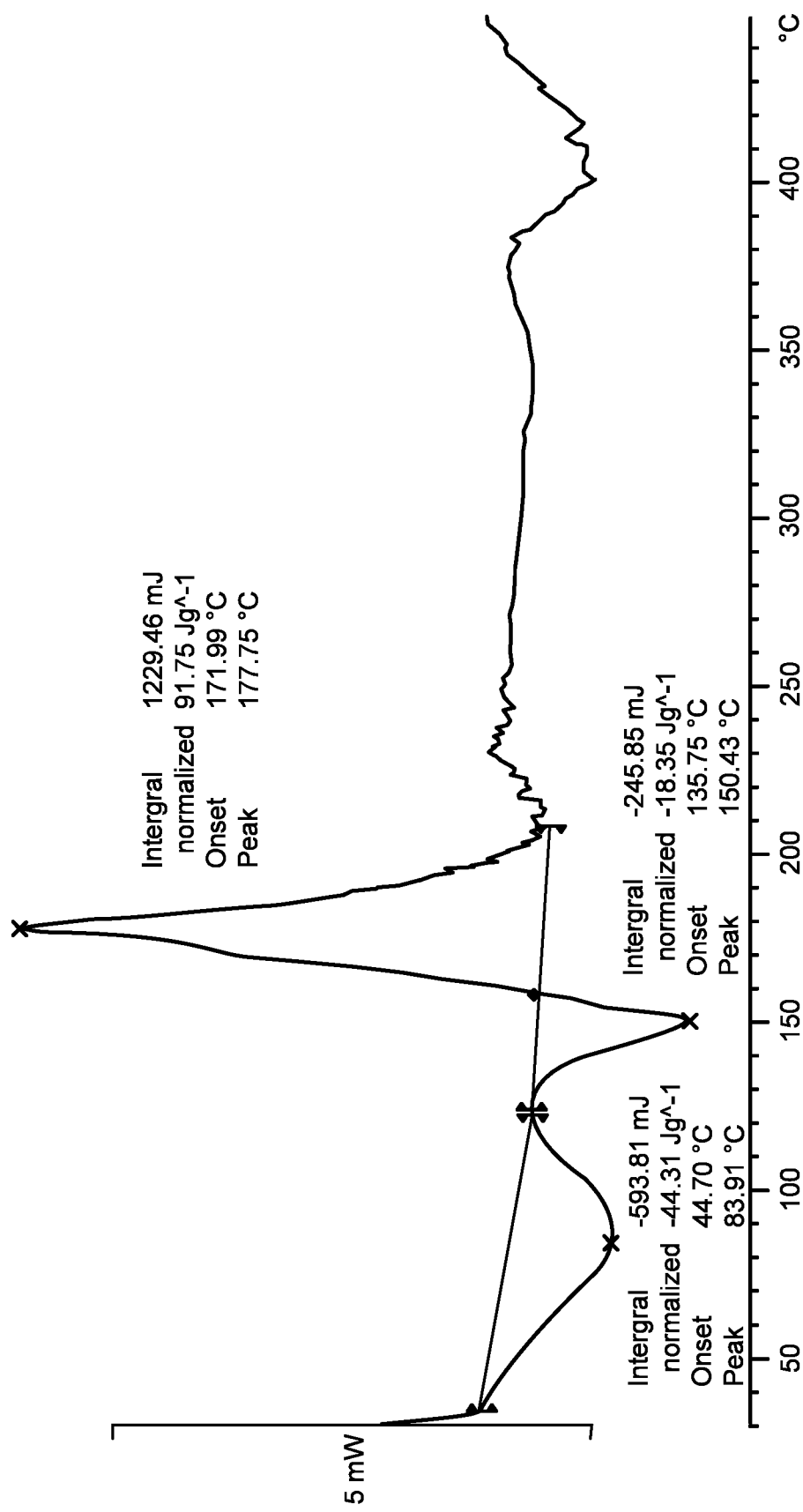
FIG. 9 shows a differential scanning calorimetry (DSC) plot of cystalline Form V of the compound of Formula (I).

In some embodiments, the crystalline Form V is further characterized by a differential scanning calorimetry (DSC) thermogram substantially in accordance with FIG. 9.

In some embodiments, the crystalline Form V is characterized by an XRPD pattern substantially in accordance with FIG. 8; and is further characterized by a differential scanning calorimetry (DSC) thermogram substantially in accordance with FIG. 9.

A $^1$H NMR spectrum of the crystalline Form V can be used to determine the content of one or more residual solvents (e.g., ethanol and/or ethyl acetate). In some embodiments, the crystalline Form V has a content of ethanol in an amount of 7.6%, as determined by a $^1$H NMR spectrum. In some embodiments, the crystalline Form V is in an ethyl acetate solvate, an ethanol solvate form, or a combination thereof. In some embodiments, crystalline Form V is an ethanol solvate.

III-5. Crystalline Form VI

In one embodiment, the present disclosure provides crystalline Form VI of a compound of Formula (I), characterized by an X-ray powder diffraction (XRPD) pattern including three or more peaks at 5.8, 10.4, 16.2, 19.4, 21.3, 22.4, 24.4, 27.5, and 31.1 degrees 2θ (±0.2 degrees 2θ).

Crystalline Form VI of the compound of Formula (I) can be characterized by an X-ray powder diffraction (XRPD) pattern having one or more, e.g., two, three, four, five, or more, peaks at 5.8, 10.4, 16.2, 19.4, 21.3, 22.4, 24.4, 27.5, and 31.1 degrees 2θ (±0.2 degrees 2θ), wherein the XRPD is made using CuK$_{\alpha 1}$ radiation. In some embodiments, the crystalline Form VI of the compound of Formula (I) is characterized by an XRPD pattern including four or more peaks at 5.8, 10.4, 16.2, 19.4, 21.3, 22.4, 24.4, 27.5, and 31.1 degrees 2θ (±0.2 degrees 2θ). In some embodiments, the crystalline Form VI of the compound of Formula (I) is characterized by an XRPD pattern including five or more peaks at 5.8, 10.4, 16.2, 19.4, 21.3, 22.4, 24.4, 27.5, and 31.1 degrees 2θ (±0.2 degrees 2θ). In some embodiments, the crystalline Form VI of the compound of Formula (I) is characterized by an XRPD pattern including six or more peaks at 5.8, 10.4, 16.2, 19.4, 21.3, 22.4, 24.4, 27.5, and 31.1 degrees 2θ (±0.2 degrees 2θ).

In some embodiments, the crystalline Form VI of the compound of Formula (I) is characterized by an XRPD pattern including peaks at 19.4, 21.3, 22.4, and 24.4 degrees 2θ (±0.2 degrees 2θ). In some embodiments, the XRPD pattern further includes one or more peaks at 5.8, 10.4, 27.5 and 31.1 degrees 2θ (±0.2 degrees 2θ). In some embodiments, the XRPD pattern further includes two or more peaks at 5.8, 10.4, 27.5 and 31.1 degrees 2θ (±0.2 degrees 2θ). In some embodiments, the XRPD pattern further includes three or more peaks at 5.8, 10.4, 27.5 and 31.1 degrees 2θ (±0.2 degrees 2θ).

In some embodiments, the crystalline Form VI is characterized by an XRPD pattern including peaks at 5.8, 10.4, 16.2, 19.4, 21.3, 22.4, and 24.4 degrees 2θ (±0.2 degrees 2θ).

Figure 10:
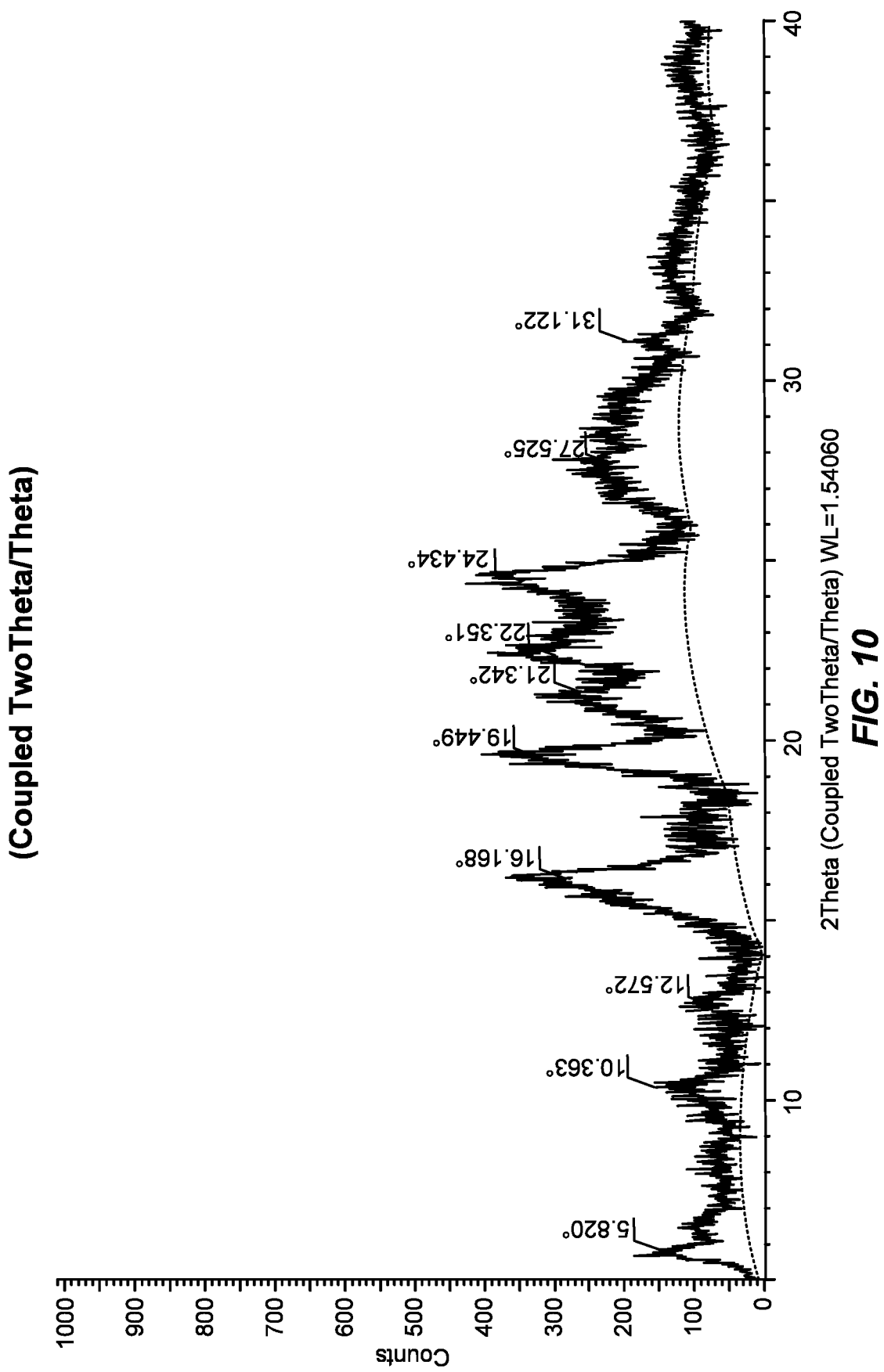
FIG. 10 shows an X-ray powder diffrations (XRPD) pattern of cystalline Form VI of the compound of Formula (I).

In some embodiments, the crystalline Form VI is characterized by an XRPD pattern substantially in accordance with FIG. 10.

In some embodiments, the crystalline Form VI is substantially free of other crystalline or amorphous forms of a compound of Formula (I).

In some embodiments, the crystalline Form VI is characterized by a differential scanning calorimetry (DSC) thermogram including an endotherm at from about 116° C. to about 170° C. In some embodiments, the crystalline Form VI is further characterized by a differential scanning calorimetry (DSC) thermogram including an endothermic peak at about 142.9° C. In some embodiments, the differential scanning calorimetry (DSC) thermogram further includes an exotherm at from about 187 to about 210° C. In some embodiments, the differential scanning calorimetry (DSC) thermogram is characterized by an exothermic peak at about 193.9° C. In some embodiments, the crystalline Form VI is further characterized by a melting point of about 142.9° C. as determined by a differential scanning calorimetry thermogram (DSC). In some embodiments, the crystalline Form VI is further characterized by a melting point onset of about 116.6° C. as determined by a differential scanning calorimetry thermogram (DSC).

Figure 11:
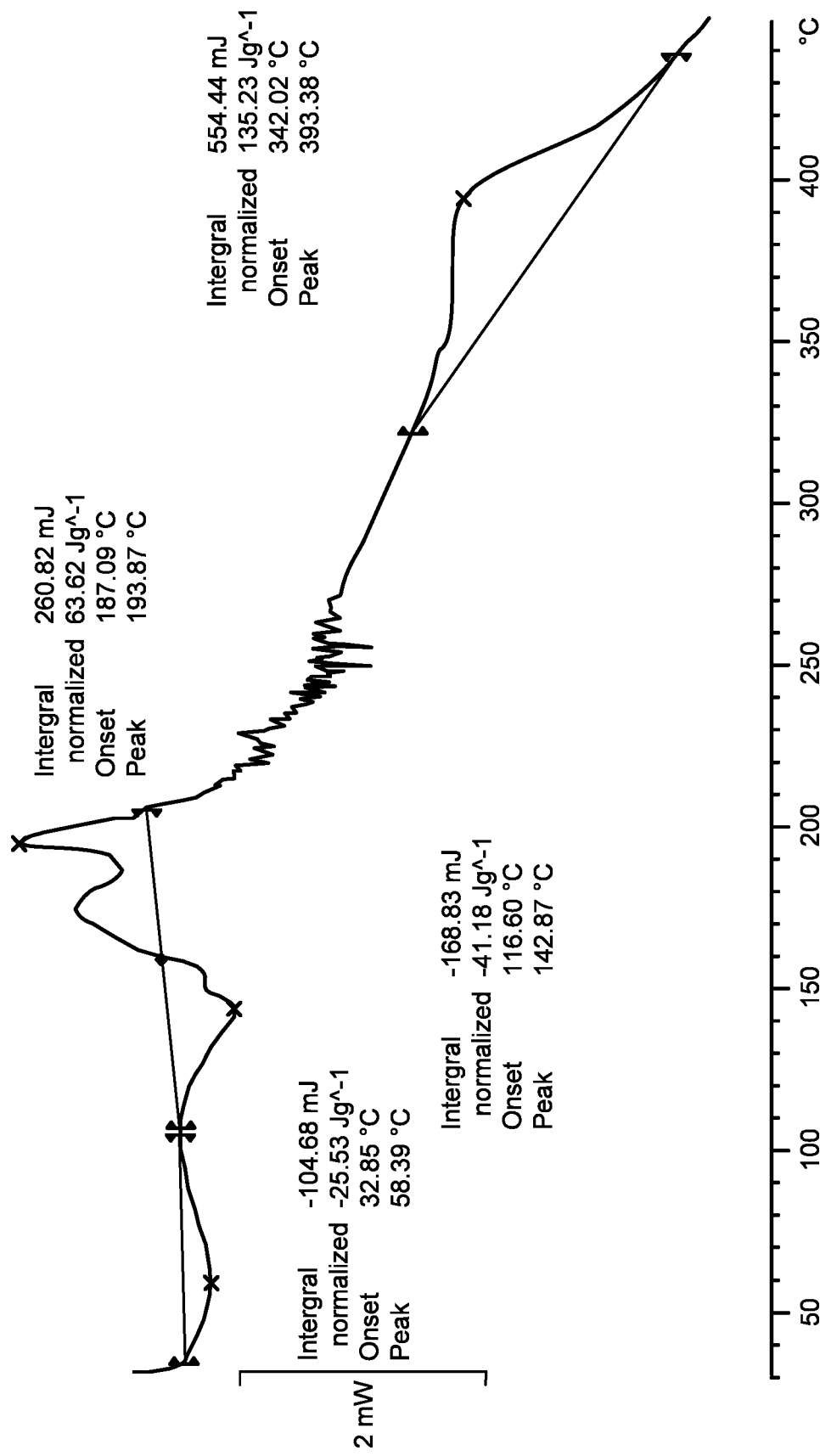
FIG. 11 shows a differential scanning calorimetry (DSC) plot of cystalline Form VI of the compound of Formula (I).
Figure 12A:
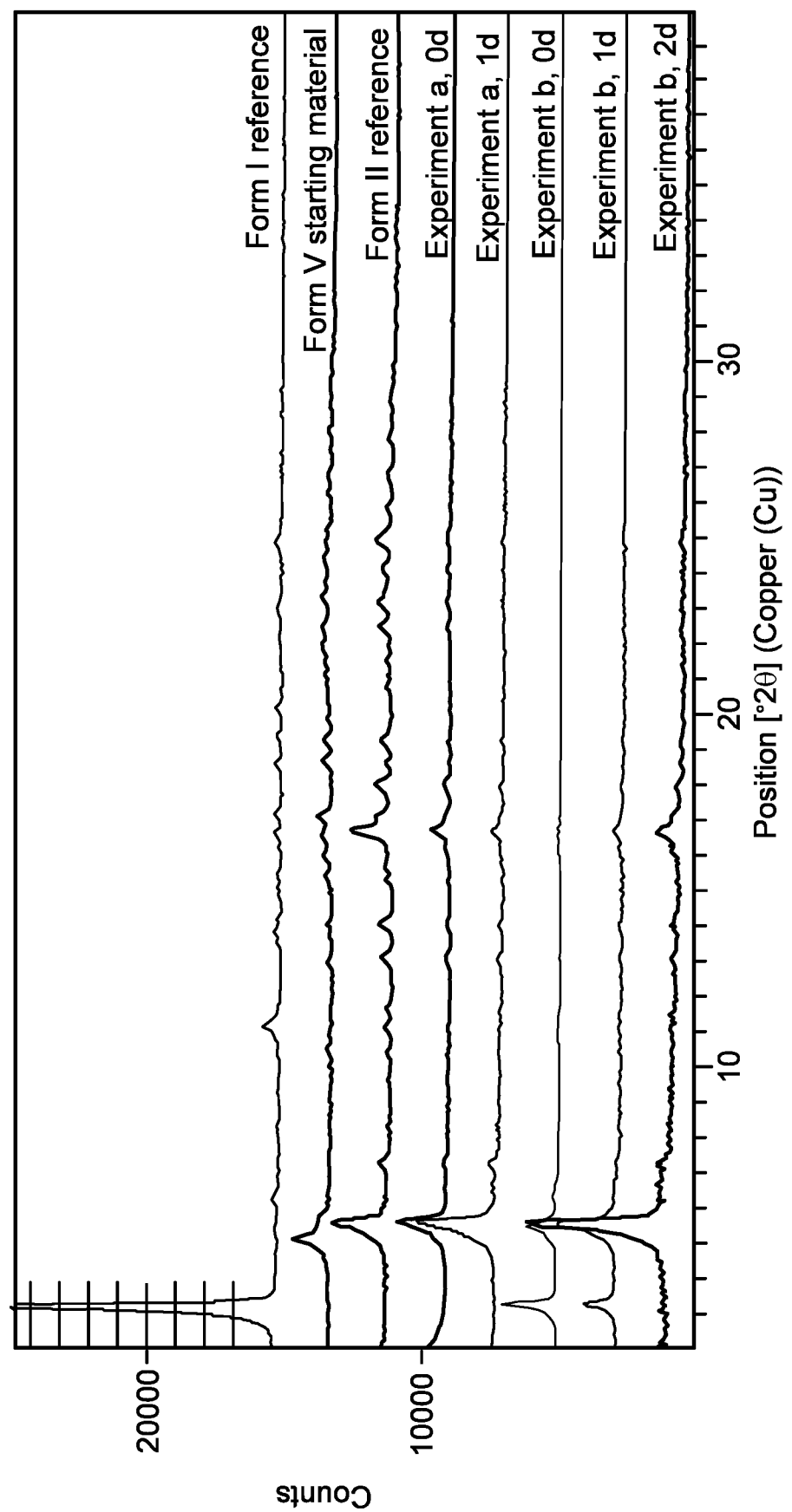
FIG. 12A-D shows the X-ray powder diffraction (XRPD) pattern of solids recovered from competitive slurry experiments using varying amounts of ethanol and ethyl acetate.
Figure 12B:
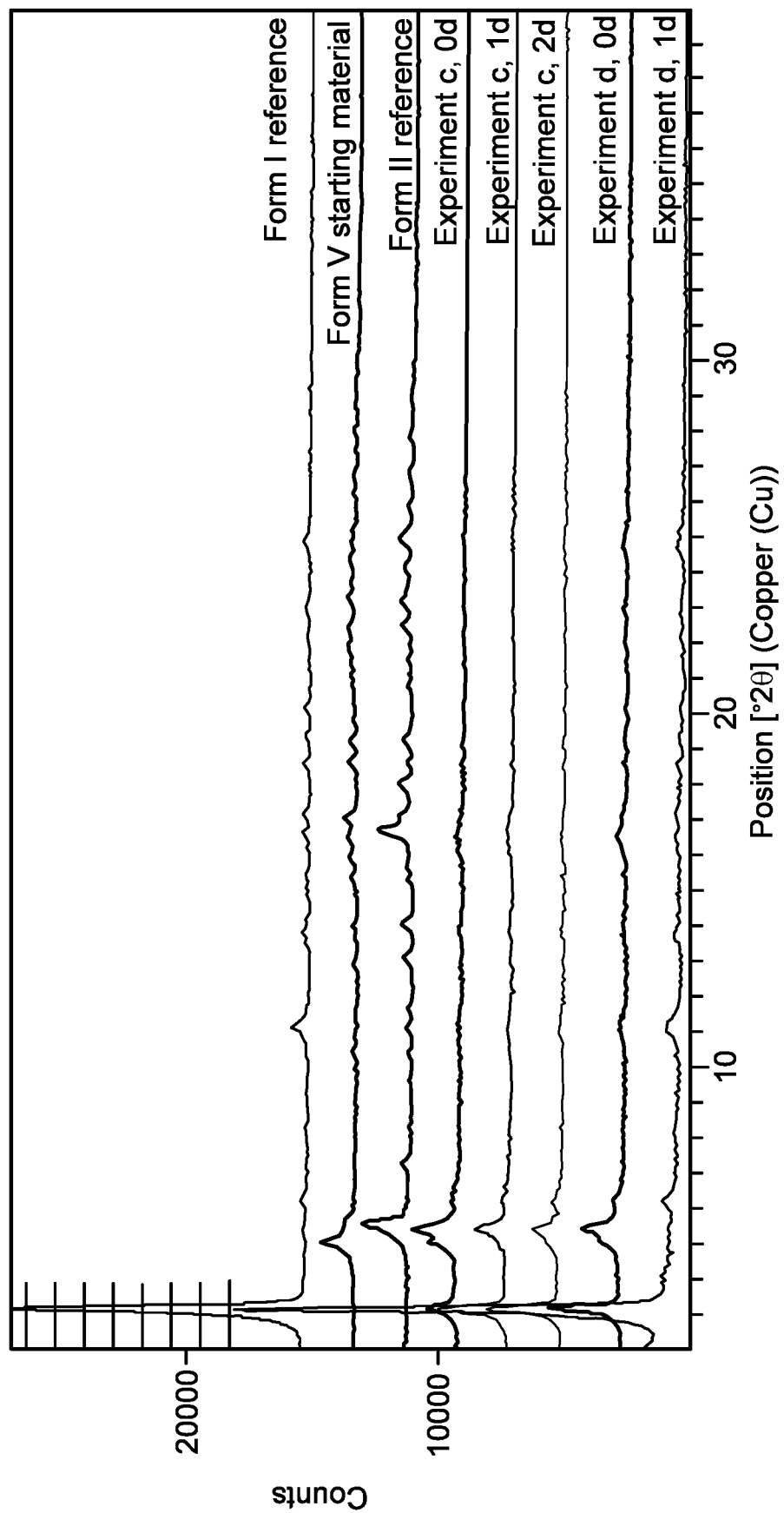
Figure 12C:
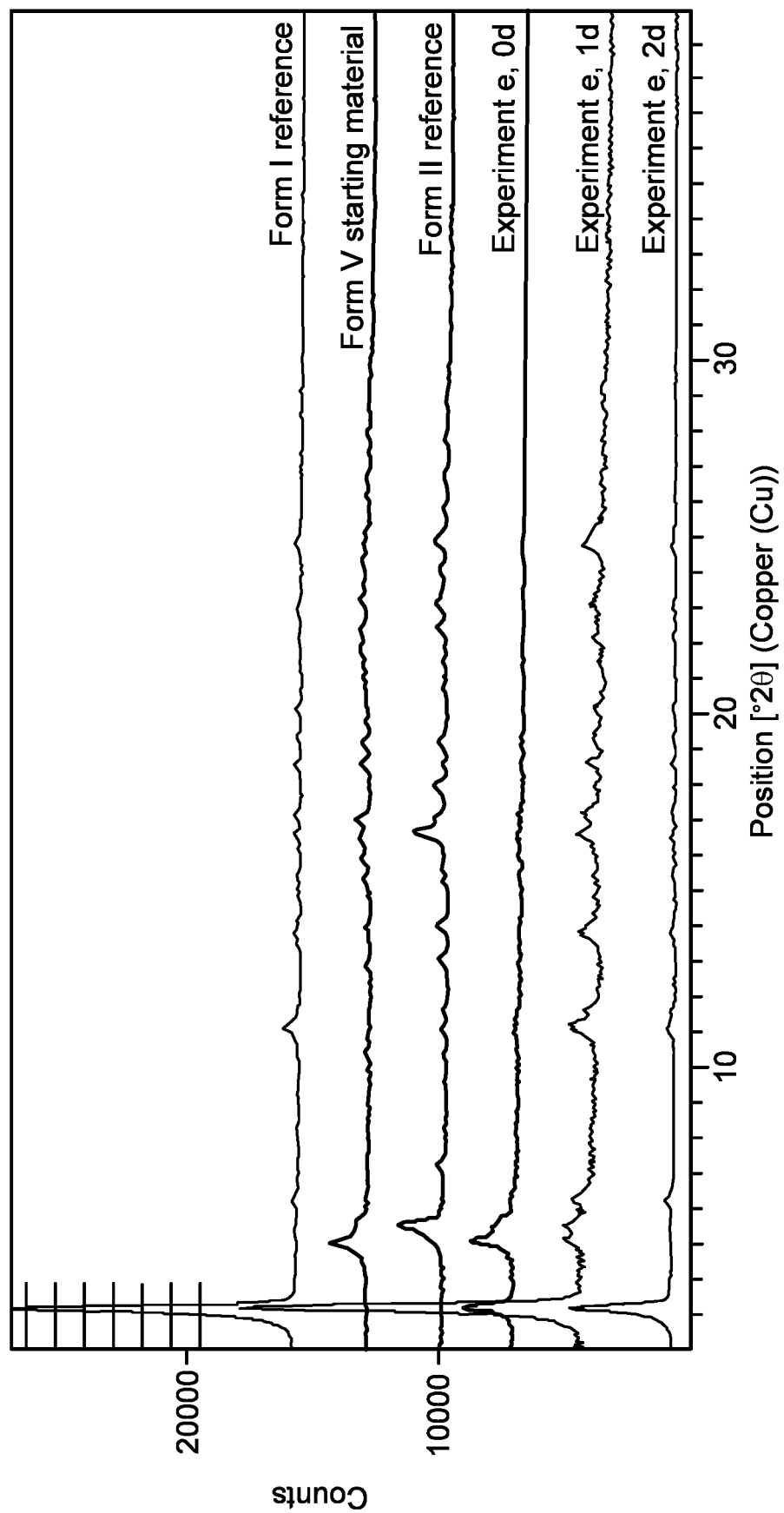
Figure 12D:
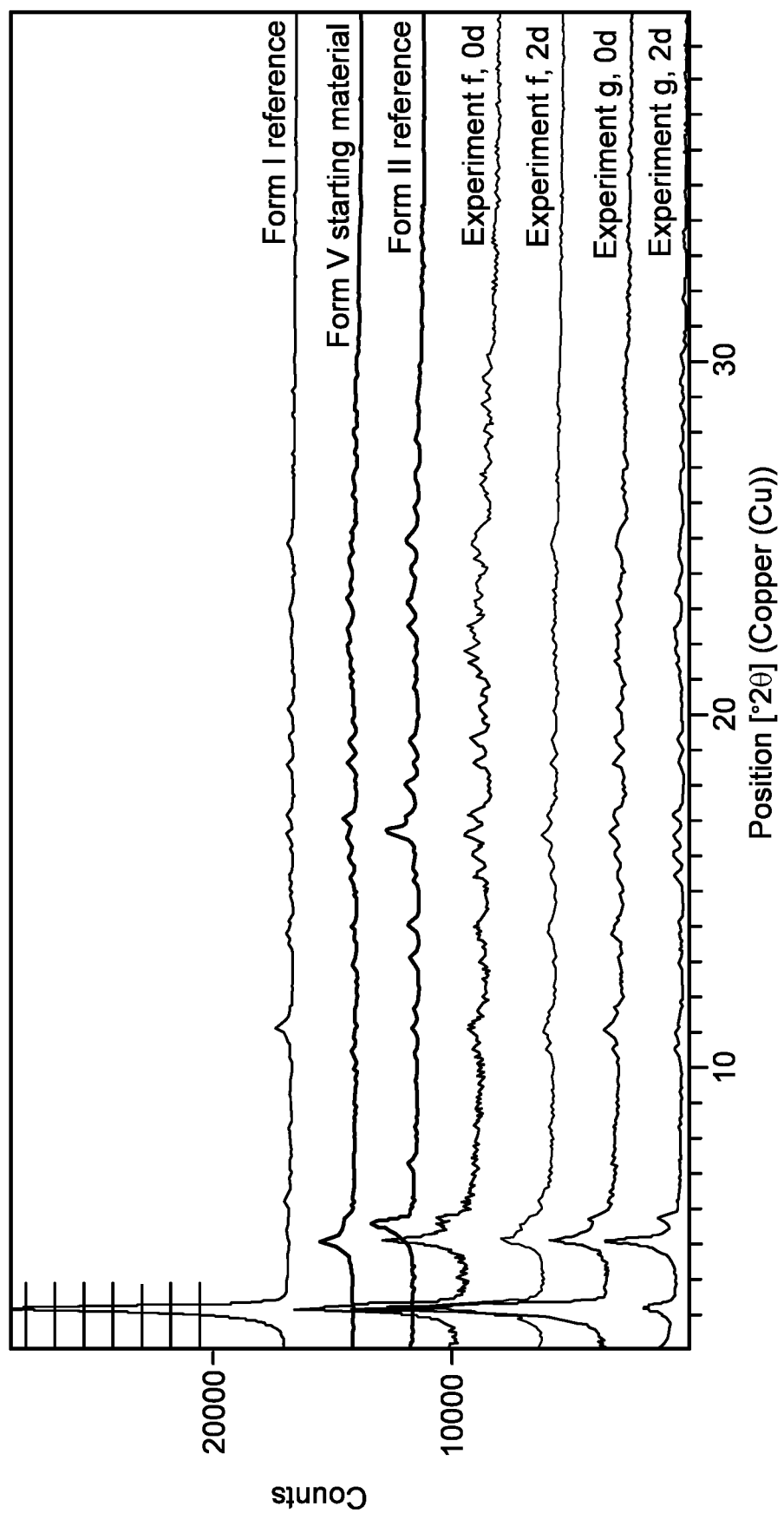

In some embodiments, the crystalline Form VI is further characterized by a differential scanning calorimetry (DSC) thermogram substantially in accordance with FIG. 11.

In some embodiments, the crystalline Form VI is characterized by an XRPD pattern substantially in accordance with FIG. 10; and is further characterized by a differential scanning calorimetry (DSC) thermogram substantially in accordance with FIG. 11.

IV. Processes for Preparing Crystalline Forms

In another aspect, the present disclosure provides a process for preparing a crystalline form of a compound of Formula (I). The process includes:
a) forming a first mixture including a compound of Formula (I) and a solvent at a temperature of at least 20° C.; and
b) adding an anti-solvent to the first mixture to form a second mixture, or
a) forming a first mixture including a compound of Formula (I) and a solvent at a temperature of at least 20° C.;
c) cooling the first or second mixture and stirring to form a precipitate;
d) isolating the precipitate; and
e) drying the precipitate to provide the crystalline form of Formula (I),
wherein the solvent is a $C_{1-4}$alkyl alcohol, a di-($C_{1-4}$alkyl) ether, a 5-6 membered cyclic ether, acetic acid, or water; and the anti-solvent is a $C_{5-7}$ alkane, $C_{1-4}$alkyl alcohol, a di-($C_{1-4}$alkyl) ether,
a 5-6 membered cyclic ether, a di-($C_{1-4}$alkyl) ketone, $C_{1-4}$alkyl-C(O)O—$C_{1-4}$alkyl, or an aromatic hydrocarbon solvent,
provided that the solvent and anti-solvent are not each a $C_{1-4}$alkyl alcohol, a di-($C_{1-4}$alkyl) ether, or a 5-6 membered cyclic ether.

In general, the morphology of the starting material (i.e., the compound of Formula (I)) is unimportant with respect to the successful recovery of crystalline material, although the kinetics of initial dissolution may be affected and a greater proportion of solvent may be required. For example, either amorphous material obtained via lyophilization or preexisting crystalline material may be used to obtain the desired crystalline form. In some cases, it may be beneficial to first isolate the compound of Formula (I) as a first crystalline form, and use the first crystalline form as the starting material to obtain the desired crystalline form. In special cases, a metastable form is heated under vacuum to synthesize the desired form.

The sodium content of the starting material can also affect the success of the crystallization. In general, samples with a sodium content of 0.5% by weight or greater are more difficult to crystallize, although more solvent can be used to help mitigate this problem.

Single Solvents and Binary Solvent Mixtures

Several solvents can be used to generate the desired crystalline form, either through use of a single solvent or a binary solvent mixture. In the case of a single solvent the starting material can be dissolved by heating in a solvent capable of forming a reasonably concentrated solution, followed by cooling to precipitate the desired crystalline form. Suitable solvents for use alone or as a mixture include but are not limited to isopropanol, ethanol, methanol, acetonitrile, acetic acid, tetrahydrofuran, and water. Alternatively, the starting material can be dissolved in a solvent capable of forming a reasonably concentrated solution at ambient temperature, followed by slow evaporation of the solvent (e.g., under ambient conditions, under a flow of an inert gas (i.e., $N_2$ or Ar) or under reduced pressure), to precipitate the desired crystalline form.

In the case of a binary solvent mixture, the material is first dissolved in a solvent capable of forming a reasonably concentrated solution as outlined above followed by the addition of a less polar solvent (e.g., an anti-solvent) in which the material is not readily soluble to precipitate the desired material. In cases wherein the solvent was initially heated to dissolve the material, the anti-solvent can be added while the solution is hot, or after it has cooled, e.g., to room temperature. In a selected example, the material is dissolved in ethanol at room temperature and ethyl acetate added to precipitate the desired crystalline form. Suitable precipitating solvents (as anti-solvents) include but are not limited to toluene, ethyl acetate, diethyl ether, acetone, methyl tert-butyl ether, isopropanol, pentane, hexane, heptane, and acetonitrile.

In some embodiments, the solvent is a $C_{1-4}$alkyl alcohol, a di-($C_{1-4}$alkyl) ether, or a 5-6 membered cyclic ether, or a mixture thereof. In some embodiments, the solvent is a $C_{1-4}$alkyl alcohol or a 5-6 membered cyclic ether. Suitable $C_{1-4}$alkyl alcohols include, but are not limited to, methanol, ethanol, or iso-propanol. Suitable di-($C_{1-4}$alkyl) ethers include, but are not limited to, diethyl ether, methyl ethyl ether, or methyl tert-butyl ether. Suitable 5-6 membered cyclic ethers include, but are not limited to, tetrahydrofuran, methyl tetrahydrofuran, or dioxanes. In some embodiments, the solvent is ethanol, tetrahydrofuran or a mixture thereof. In some embodiments, the solvent is ethanol. In some embodiments, the solvent is tetrahydrofuran. In some embodiments, the solvent further comprises water.

In some embodiments, the present disclosure provides a process for preparing the crystalline Form II, V or VI of the compound of Formula (I), the process including:
a) forming a first mixture including a compound of Formula (I) and ethanol at a temperature of at least 20° C.;
c) cooling the first mixture and stirring to form a precipitate;
d) isolating the precipitate; and
e) drying the precipitate to provide the crystalline Form II or V of Formula (I).

The temperature at which step a) is conducted can influence the identity of the resulting crystalline form. Without wishing to be bound by theory, low temperatures favor the formation of crystalline Form VI, moderate temperatures favor the formation of crystalline Form V, and higher temperatures favor the formation of crystalline Form II. In some embodiments, step a) is conducted at a temperature from 20° C. to 30° C. In some embodiments, step a) is conducted at a temperature from 30° C. to 40° C. In some embodiments, step a) is conducted at a temperature from 40° C. to 65° C.

In some embodiments, the present disclosure provides a process for preparing crystalline Form I, II, III, IV or V of the compound of Formula (I), the process including:
a) forming a first mixture including a compound of Formula (I) and a solvent at a temperature of at least 20° C.;
b) adding an anti-solvent to the first mixture to form a second mixture;
c) cooling the second mixture and stirring to form a precipitate;
d) isolating the precipitate; and
e) drying the precipitate to provide the crystalline Form I, II, III, IV, or V of Formula (I), respectively,
wherein the solvent is ethanol or tetrahydrofuran; and the anti-solvent is ethyl acetate, methyl tert-butyl ether, heptane, or toluene.

In some embodiments, the present disclosure provides a process for preparing crystalline Form I of the compound of Formula (I), the process including:
a) forming a first mixture including a compound of Formula (I) and ethanol at a temperature of at least 20° C.;
b) adding an anti-solvent to the first mixture to form a second mixture;
c) cooling the second mixture and stirring to form a precipitate;
d) isolating the precipitate; and
e) drying the precipitate to provide the crystalline Form I of Formula (I),
wherein the anti-solvent is ethyl acetate or toluene.

In some embodiments, the present disclosure provides a process for preparing crystalline Form I of the compound of Formula (I), the process including:
a) forming a first mixture including a compound of Formula (I) and ethanol at a temperature of at least 20° C.;
b) adding ethyl acetate to the first mixture to form a second mixture;
c) cooling the second mixture and stirring to form a precipitate;
d) isolating the precipitate; and
e) drying the precipitate to provide the crystalline Form I of Formula (I).

In some embodiments, the present disclosure provides a process for preparing crystalline Form I of the compound of Formula (I), the process including:
a) forming a first mixture including a compound of Formula (I) and ethanol at a temperature of at least 20° C.;
b) adding toluene to the first mixture to form a second mixture;
c) cooling the second mixture and stirring to form a precipitate;
d) isolating the precipitate; and
e) drying the precipitate to provide the crystalline Form I of Formula (I).

In some embodiments, the present disclosure provides a process for preparing crystalline Form II, V, or a mixture of Forms II and V of the compound of Formula (I), the process including:
a) forming a first mixture including a compound of Formula (I) and ethanol at a temperature of at least 20° C.;
b) adding heptane to the first mixture to form a second mixture;
c) cooling the second mixture and stirring to form a precipitate;
d) isolating the precipitate; and
e) drying the precipitate to provide the crystalline Form II of Formula (I).

In some embodiments, the present disclosure provides a process for preparing crystalline Form III of the compound of Formula (I), the process including:
a) forming a first mixture including a compound of Formula (I) and ethanol at a temperature of at least 20° C.;
b) adding methyl tert-butyl ether to the first mixture to form a second mixture;
c) cooling the second mixture and stirring to form a precipitate;
d) isolating the precipitate; and
e) drying the precipitate to provide the crystalline Form III of Formula (I).

In some embodiments, the present disclosure provides a process for preparing crystalline Form IV of the compound of Formula (I), the process including:
a) forming a first mixture including a compound of Formula (I) and tetrahydrofuran at a temperature of at least 20° C.;
b) adding ethyl acetate to the first mixture to form a second mixture;
c) cooling the second mixture and stirring to form a precipitate;
d) isolating the precipitate; and
e) drying the precipitate to provide the crystalline Form IV of Formula (I).

In some embodiments, the first mixture comprises a crude compound of Formula (I). In other embodiments, the first mixture comprises a crystalline form of a compound of Formula (I), e.g., a crystalline form of a compound of Formula (I) according to this disclosure, or a crystalline form described in WO 2020/123772 (i.e., Form A or Form B). In some embodiments, the first mixture comprises crystalline Form A, B, I, II, III, IV, V or VI. In some embodiments, the first mixture comprises crystalline Form A or B. In some embodiments, the first mixture comprises crystalline Form A. In some embodiments, the first mixture comprises crystalline Form B.

In some embodiments, the first and/or second mixture are a solution including the compound of Formula (I). In some embodiments, the first and/or second mixture are a solution including the compound of Formula (I) and ethanol. In some embodiments, the first and/or second mixture are a hazy solution including the compound of Formula (I) and ethanol. In some embodiments, the first and/or second mixture are a hazy solution including the compound of Formula (I) and tetrahydrofuran.

Slow evaporation of a saturated solution of material in an appropriate solvent or mixture is also effective in obtaining crystalline material. In general, the sample has lower crystallinity as measured by XRPD. Suitable solvents include but are not limited to acetone, tetrahydrofuran, ethanol, methanol, acetonitrile, and water.

Solvent/Antisolvent Ratio

In the case of a binary solvent mixture, the formation of the crystalline form can be sensitive to the ratio of solvent to precipitating solvent. For example, if the material is dissolved in ethanol and ethyl acetate is added as a precipitating solvent, the final ethanol to ethyl acetate ratio can vary from 4:1 to 1:4, e.g. 4:1, 3:1, 2:1, 1:1, 1:2, 1:3 or 1:4. In some embodiments, the final ethanol to ethyl acetate ratio is 2:1. Without wishing to be bound by theory, solvent systems characterized by a greater ethanol content than ethyl acetate content tend to favor the formation of crystalline Form II. By contrast solvent systems characterized by a lower ethanol content than ethyl acetate content tend to favor the formation of crystalline Form I. In one embodiment, the ethanol content is greater than the ethyl acetate content. In another embodiment the ethanol content is lower than the ethyl acetate content. In some embodiments, the ethanol to ethyl acetate ratio is 4:1, 3:1, 2:1 or 1:1. In alternative embodiments the ethanol to ethyl acetate content is 1:1, 1:2, 1:3 or 1:4.

In some embodiments, the ethanol to ethyl acetate ratio is from 1:1 to 1:4. In some embodiments, the ethanol to ethyl acetate ratio is from 1:1 to 1:2. In some embodiments, the ethanol to ethyl acetate ratio is about 5:8. In some embodiments, the ethanol to toluene ratio is from 1:1 to 1:4. In some embodiments, the ethanol to toluene ratio is about 1:2. In some embodiments, the ethanol to methyl tert-butyl ether ratio is from 1:1 to 1:4. In some embodiments, the ethanol to methyl tert-butyl ether ratio is about 1:2. In some embodiments, the ethanol to methyl tert-butyl ether ratio is about 5:14. In some embodiments, the tetrahydrofuran to ethyl acetate ratio is from 1.5:1 to 1:2. In some embodiments, the tetrahydrofuran to ethyl acetate ratio is about 5:4. In some embodiments, the ethanol to heptane ratio is from 1:1 to 1:4.

If slow evaporation is used to obtain crystalline material, a mixture of solvents may be used. In some embodiments the ratio of solvents can vary from 4:1 to 1:1. In another embodiment, slow evaporation of one solvent can be used to obtain crystalline material.

Solvent/Compound Ratio

The ratio or concentration of compound relative to solvent can be variable depending on the solvent or solvent mixture used. Typical concentrations can range from 250 mg/mL to 10 mg/mL with the limiting factor at the higher end being the solubility of the material or the ease of recovery the material once crystallization has occurred. For example, approximately 200 mg of amorphous material can be dissolved in 1 mL of ethanol with subsequent addition of an anti-solvent (e.g., ethyl acetate, heptane, or toluene) added to afford the crystalline form.

Temperature Control

In general, the maximum heating temperature used in the above methods can range from 20° C. to the reflux temperature of the solvent. Most typical temperatures range from 20° C. to 60° C. Once a solution has been obtained, and, if required, a precipitating solvent added, the mixture is cooled to room temperature. The rate of cooling can affect the size, shape, and quality of the crystals. If the solution is subjected to prolonged heating over 60° C. or contains a reactive solvent, decomposition can occur.

In some embodiments, step a) is conducted at a temperature of from 20° C. to 100° C. In some embodiments, step a) is conducted at a temperature of from 40° C. to 80° C. In some embodiments, step a) is conducted at a temperature of from 55° C. to 60° C. In some embodiments, step a) is conducted at a temperature of from 35° C. to 55° C. In some embodiments, step a) is conducted at a temperature from 35° C. to 40° C. In some embodiments, step a) is conducted at a temperature from 20° C. to 25° C.

In some embodiments, when step b) is present, step b) is conducted at a temperature of from 20° C. to 100° C. In some embodiments, when step b) is present, step b) is conducted at a temperature of from 40° C. to 80° C. In some embodiments, when step b) is present, step b) is conducted at a temperature of from 55° C. to 60° C. In some embodiments, when step b) is present, step b) is conducted at a temperature of from 35° C. to 55° C. In some embodiments, when step b) is present, step b) is conducted at a temperature of from 35° C. to 40° C. In some embodiments, when step b) is present, step b) is conducted at a temperature of from 20° C. to 25° C.

In some embodiments, steps a) and b) are each conducted at a temperature of from about 55° C. to about 60° C. In some embodiments, steps a) and b) are each conducted at a temperature of from about 35° C. to 55° C. In some embodiments, steps a) and b) are each conducted at a temperature of from about 35° C. to 40° C. In some embodiments, steps a) and b) are each conducted at a temperature of from about 20° C. to 25° C.

Rate of Crystallization

Several factors significantly impact the rate of crystallization. These include, but are not limited to: rate of precipitating solvent addition, rate of mixture cooling, and presence of nucleation sites such as dust, seed crystals, or defects on the glass surface. Variations in these parameters can affect the size, shape, and quality of the crystals.

In some embodiments, step c) is conducted by c-1) cooling the first or the second mixture to room temperature for a period of from 30 minutes to 3 hours; and c-2) stirring at room temperature for a period of from 12 hours to 72 hours to form the precipitate. In some embodiments, step c) is conducted by c-1) cooling the first or the second mixture to room temperature for a period of from 1 to 2 hours; and c-2) stirring at room temperature for a period of about 18 hours to form the precipitate.

In some embodiments, a crystal seed of the compound of Formula (I) is added during step c).

Isolation of the Crystal Form

Several methods for isolation of the desired crystalline form from the supernatant can be used including filtration, decantation, and solvent evaporation. In general, the crystalline form was obtained by collecting any formed solids by vacuum filtration, followed by air-drying and subsequent exposure to high vacuum to remove any residual solvent.

In some embodiments, the isolating of step d) is conducted by filtration.

In some embodiments, the drying of step e) is conducted a temperature of from about 55° C. to about 60° C. under vacuum. In some embodiments, the drying of step e) is conducted at ambient temperature, e.g., between about 20° C. and 25° C. under vacuum.

Table 1 summarizes the preparation of crystalline forms of Formula (I).

TABLE 1

Crystallization summary

| (I) (g) | Solvent (v/w parts) | Anti-solvent (v/w parts) | Addition mode | Add'n Temp (° C.) | Crude % yield | Temp (° C.) | (hrs) | wt % residual solvent | wt % residual anti-solvent | XRPD |
|---|---|---|---|---|---|---|---|---|---|---|
| 1.00 | 8.0 THF | 11.0 EtOAc | Normal[B] | 20 | 87 | 40-45 | 18 | 0.28 | 1.34 | — |
|  |  |  |  |  |  | 55-60 | 48 | 0.22 | 1.05 | — |
| 1.00 | 8.0 THF |  | Normal[B] | 20 | 90 | 40-45 | 18 | 1.03 | 6.96 | — |
|  |  | 8.0 iPrOAc |  |  |  | 55-60 | 48 | 0.89 | 6.46 | — |
| 1.00 | 8.0 THF | 6.0 MTBE | Normal[B] | 20 | 53 | 40-45 | 18 | 0.73 | 1.43 | — |
|  |  |  |  |  |  | 55-60 | 48 | 0.46 | 0.90 | — |
| 1.00 | 8.0 THF | 11.0 EtOAc | Inverse[C] + seeds | 20 | 87 | 55-60 | 48 | 0.95 | 3.15 | Amorphous |
| 1.00 | 8.0 THF | 8.0 iPrOAc | Inverse[C] + seeds | 20 | 89 | 55-60 | 48 | 0.98 | 6.10 | — |
| 1.00 | 8.0 THF | 8.0 MTBE | Inverse[C] + seeds | 20 | Semi-solid/Gel | — | — | — | — | — |
| 1.00 | 5.0 THF | 4.0 EtOAc | Normal[B] | ~60 | 58[A] | 55-60 | 72 | 0.06 | 0.08 | Form IV |
| 1.00 | 6.0 THF | 4.0 MTBE | Normal[B] | ~60 | 43 | 55-60 | 72 | 1.82 | 2.14 | — |
| 1.00 | 3.0 THF | 5.0 IPA | Normal[D] | ~60 | 56 | 55-60 | 18 | 0.06 | 0.91 | Form A[F] |
| 1.00 | 4.0 THF | 5.0 MEK | Normal[D] | ~60 | Emulsion | — | — | — | — | — |
| 1.00 | 7.0 EtOH | — | — | ~60 | 37 | 55-60 | 18 | 0.68 | — | Form II |
| 1.00 | 13.0 THF | 4.0 EtOAc | All-in[E] | ~60 | 16 | 55-60 | 18 | 0.12 | 0.47 |  |
| 1.00 | 5.0 THF | 4.0 EtOAc | Normal[B] | ~60 | 83 | 55-60 | 18 | 0.09 | 0.25 |  |
| 0.50 | 5.0 THF | 4.0 MeTHF + 8 MeTHF | Normal[B] | ~60 | Solution | — | — | — | — | — |
| 0.50 | 6.0 THF | 10.0 IPA + 8 IPA | Normal[D] | ~60 | Solution | — | — | — | — | — |
| 0.50 | 5.0 EtOH | 10.0 MTBE | Normal[B] | ~60 | 68 | 55-60 | 18 | ~0 | 0.40 | Form III |
| 1.00 | 5.0 THF | 3.0 Toluene | Normal[B] | ~60 | 75 | 55-60 | 72 | 0.32 | 1.90 |  |
| 1.00 | 5.0 EtOH | 10.0 Toluene | Normal[B] | ~60 | 82 | 55-60 | 72 | 0.04 | ~0 | Form I |
| 1.00 | 5.0 EtOH | 8.0 EtOAc | Normal[B] | ~60 | 82 | 55-60 | 72 | 0.04 | 0.04 | Form I |
| 3.00 | 5.0 THF | 4.0 EtOAc | Normal[B] + seeds | 55-60 | 93 | 55-60 | 18 | 0.05 | 0.38 | Form IV |
| 3.00 | 5.0 EtOH | 14.0 MTBE | Normal[B] + seeds | 55-60 | 82 | 55-60 | 18 | 0.14 | 1.56 | Form III |
| 3.00 | 5.0 EtOH | 8.0 EtOAc | Normal[B] + seeds | 55-60 | 83 | 55-60 | 18 | ~0 | 0.02 | Form I |
| 3.00 | 5.0 THF | 5.0 EtOAc | Normal[B] | 55-60 | 94 | 55-60 | 72 | 0.16 | 0.72 |  |
| 3.00 | 5.0 EtOH | 10.0 EtOAc | Normal[B] | 55-60 | 85 | 55-60 | 72 | 0.03 | 0.15 |  |
| 1.00 | 5.0 THF | 3.0 DCM | Normal[B] | 45-60 reflux | 94 | 55-60 | 20 | 6.97 | 0.38 |  |
| 1.00 | 5.0 EtOH | 3.0 DCM | Normal[B] | 45-60 reflux | 32 | 55-60 | 20 | 0.06 | ~0 |  |
| 1.00 | 5.00 EtOH | 10.0 EtOAc | Normal[B] | 55-60 21.5 h HOLD | 77 | 55-60 | 18 | 0.51 | 1.16 | Form I |
| 1.00 | 5.00 EtOH, 0.25 H$_2$O | 10.0 EtOAc | Normal[B] | 55-60 | 59 | 55-60 | 20 | 0.05 | 0.39 |  |

TABLE 1-continued

Crystallization summary

| (I) (g) | Solvent (v/w parts) | Anti-solvent (v/w parts) | Addition mode | Add'n Temp (° C.) | Crude % yield | Temp (° C.) | (hrs) | wt % residual solvent | wt % residual anti-solvent | XRPD |
|---|---|---|---|---|---|---|---|---|---|---|
| 1.00 | 5.00 EtOH, 0.25 THF, 0.25 MeTHF | 10.0 EtOAc | Normal[B] | 55-60 | 75 | 55-60 | 18 | 0.73 | 0.93 | Form I |
| 1.00 | 5.00 EtOH, 0.10 H₂O | 10.0 EtOAc | Normal[B] | 55-60 | 80 | 55-60 | 20 | 0.49 | 1.01 | |
| 1.00 | 5.00 EtOH, 0.10 THF, 0.10 MeTHF | 10.0 EtOAc | Normal[B] | 55-60 | 83 | 55-60 | 20 | 0.44 | 1.00 | |
| 1.00 | 5.00 EtOH, 0.25 MeTHF | 10.0 EtOAc | Normal[B] | 55-60 | 84 | 55-60 | 20 | 0.47 | 1.02 | |

[A]The isolation was not optimized for yield. Some product was left behind on flask wall during the filtration.
[B]Normal addition: addition of the anti-solvent into the compound of Formula (I)/solvent batch.
[C]Inverse addition: addition of the compound of Formula (I)/solvent into the anti-solvent batch.
[D]Normal addition: addition of the solvent into the compound of Formula (I)/anti-solvent batch.
[E]All-in: The compound of Formula (I)/solvent/anti-solvent all added at the start. Additional solvent added at elevated temp to try to solubilize the compound of Formula (I).
[F]Form A of the compound of Formula (I) is disclosed in PCT/US2019/065916.

V. Compositions

The crystalline form of a compound of Formula (I) may be in the form of, or used to prepare compositions (e.g., further processed with one or more excipients) suitable for administration to a subject. In general, such compositions are "pharmaceutical compositions" including a compound of Formula (I) and one or more pharmaceutically acceptable or physiologically acceptable diluents, carriers or excipients. In certain embodiments, the compound of Formula (I) is present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present disclosure.

The pharmaceutical compositions containing the active ingredient (e.g., a compound of Formula (I)) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of an CD73 inhibitor contemplated by the present disclosure (i.e., a compound of Formula (I)), and one or more pharmaceutically and physiologically acceptable formulation agents. Suitable pharmaceutically acceptable or physiologically acceptable diluents, carriers or excipients include, but are not limited to, anti-oxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Typical buffers that may be used in the compositions according to this disclosure include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. A variety of drug delivery apparatus may be used to deliver a crystalline form of a compound of Formula (I), including implants (e.g., implantable pumps) and catheter systems, slow injection pumps and devices, all of which are well known to the skilled artisan.

Depot injections, which are generally administered subcutaneously or intramuscularly, may also be utilized to release the crystalline form of a compound of Formula (I) disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present disclosure contemplates the administration of a crystalline form of a compound of Formula (I) in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The crystalline forms of the compound of Formula (I) contemplated by the present disclosure may be in the form of any other suitable pharmaceutical composition (e.g., sprays for nasal or inhalation use) currently known or developed in the future.

VI. Methods of Use

The present disclosure contemplates the use of a crystalline form of a compound of Formula (I) described herein in the treatment or prevention of a broad range of diseases, disorders and/or conditions, and/or the symptoms thereof. While particular uses are described in detail hereafter, it is to be understood that the present disclosure is not so limited. Furthermore, although general categories of particular diseases, disorders and conditions are set forth hereafter, some of the diseases, disorders and conditions may be a member of more than one category, and others may not be a member of any of the disclosed categories.

The use of a crystalline form of a compound of Formula (I) in the methods of treatment described herein encompasses the direct use (e.g., administration) of a crystalline form according to this disclosure to a subject, as well as the use of a crystalline form in the preparation of a medicament for the treatment of the indications described herein. In some embodiments, the crystalline form of the compound described herein is preserved in the final dosage form administered to a subject. In other embodiments, the crystalline form may undergo a physical change, for example, to an amorphous form, a different crystalline form, or a solubilized form, prior to administration to a subject.

Oncology-related Disorders. In accordance with the present disclosure, a compound of Formula (I) (e.g., a crystalline form described herein) can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas such as pancreatic adenocarcinoma, lymphomas, carcinomas, melanomas, leukemias, myelomas, sarcomas, teratocarcinomas, chemically-induced cancers, metastasis, and angiogenesis. The disclosure contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer is metastatic or at risk of becoming metastatic, or may occur in a diffuse tissue, including cancers of the blood or bone marrow (e.g., leukemia). In some further embodiments, the crystalline form of a compound of Formula (I) can be used to overcome T-cell tolerance.

In one embodiment, the cancer is a gastrointestinal malignancy such as pancreatic cancer. In one embodiment, the cancer is metastatic pancreatic adenocarcinoma. In one embodiment, a patient is treated for pancreatic cancer using the compound of Formula (I) and an anti-PD-1 antibody. In another embodiment, a patient is treated for first line metastatic pancreatic cancer using a compound of Formula (I) and an anti-PD-1 antibody and standard of care agents for pancreatic cancer such as those described herein. Patients may be treatment experienced or treatment naïve.

In some embodiments, the present disclosure provides methods for treating a proliferative condition, cancer, tumor, or precancerous condition with a compound of Formula (I) (e.g., a crystalline form described herein) and at least one additional therapeutic or diagnostic agent, examples of which are set forth elsewhere herein.

In some embodiments, the methods described herein may be indicated as first line, second line or third line treatments.

Immune-related Disorders and Disorders with an Inflammatory Component. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the compound of Formula (I) (e.g., a crystalline form described herein) such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The compound of Formula (I) (e.g., a crystalline form described herein) can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The compound of Formula (I) (e.g., a crystalline form described herein) can also be used to stimulate the immune system of patients suffering from iatrogenically-induced immune suppression, including those who have undergone bone marrow transplants, chemotherapy, or radiotherapy.

In particular embodiments of the present disclosure, the compound of Formula (I) (e.g., a crystalline form described herein) is used to increase or enhance an immune response to an antigen by providing adjuvant activity. In a particular embodiment, at least one antigen or vaccine is administered to a subject in combination with a compound of Formula (I)

(e.g., a crystalline form described herein) to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with a compound of Formula (I) (e.g., a crystalline form described herein).

Microbial-related Disorders. By inhibiting the immunosuppressive and anti-inflammatory activity of CD73, the present disclosure contemplates the use of a compound of Formula (I) (e.g., a crystalline form described herein) in the treatment and/or prevention of any viral, bacterial, fungal, parasitic or other infective disease, disorder or condition for which treatment with an CD73 inhibitor may be beneficial. Examples of such diseases and disorders include HIV and AIDS, staphylococcal and streptococcal infections (e.g., *Staphylococcus aureus* and *streptococcus sanguinis*, respectively), *Leishmania, Toxoplasma, Trichomonas, Giardia, Candida albicans, Bacillus anthracis*, and *Pseudomonas aeruginosa*. Compounds of the disclosure can be used to treat sepsis, decrease or inhibit bacterial growth, and reduce or inhibit inflammatory cytokines.

CNS-related and Neurological Disorders. Inhibition of CD73 may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Other Disorders. Embodiments of the present disclosure contemplate the administration of a compound of Formula (I) (e.g., a crystalline form described herein) to a subject for the treatment or prevention of any other disorder that may benefit from at least some level of CD73 inhibition. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

In some embodiments, a compound of Formula (I) (e.g., a crystalline form described herein) may be used to inhibit statin-induced adenosine production, or reduce or decrease increases in blood glucose caused by a statin in a subject taking a statin (e.g., lovastatin and pravastatin).

Selection of Patients.

In some instances, the methods according to this disclosure may be indicated in certain patients, for example based on CD73 as a biomarker, high microsatellite instability, or high tumor mutational burden. In some instances, the subject is identified as having an oncogene driven or oncogene addicted cancer that has a mutation in at least one gene associated with CD73. Methods of testing determining CD73 levels and the presence of CD73 associated oncogenes are disclosed in WO 2020/185859 and WO 2020/205527.

Routes of Administration

The present disclosure contemplates the administration of a crystalline form of a compound of Formula (I), and compositions thereof, in any appropriate manner. In one or more embodiments, the crystalline form of a compound of Formula (I) is useful in the manufacture of a medicament suitable for administration to a subject. In some embodiments, the crystalline form of the compound of Formula (I) is preserved in the medicament administered to a subject. In other embodiments, the crystalline form of the compound of Formula (I) undergoes a physical change, e.g., to an amorphous form, or a different crystalline form, during preparation of the medicament. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the crystalline form of a compound of Formula (I) disclosed herein over a defined period of time.

Particular embodiments of the present disclosure contemplate oral administration. Other embodiments of the present disclosure contemplate parenteral administration.

5'-Nucleotidase, Ecto and Inhibition Thereof

Human CD73 (also referred to as 5'-nucleotidase, ecto; NT5E; or 5NT) is a 574 amino acid residue protein (Accession No. AAH6593). Eukaryotic CD73 functions as a noncovalent homodimer with two structural domains, wherein the N- and C-terminal domains are connected by a hinge region that enables the enzyme to undergo large domain movements and switch between open and closed conformations (Knapp, K. et al. (2012) Structure 20:2161-73).

CD73 inhibitors can modulate purinergic signaling, a type of extracellular signaling mediated by purine nucleotides and nucleosides such as ATP and adenosine. Purinergic signaling involves the activation of purinergic receptors in the cell and/or in nearby cells, resulting in the regulation of cellular functions. The enzymatic activity of CD73 plays a strategic role in calibrating the duration, magnitude, and chemical nature of purinergic signals delivered to various cells (e.g., immune cells). Alteration of these enzymatic activities can change the course or dictate the outcome of several pathophysiological events, including cancer, autoimmune and inflammatory diseases, infections, atherosclerosis, and ischemia-reperfusion injury, suggesting that these ecto-enzymes represent novel therapeutic targets for managing a variety of disorders.

Studies using tissues that overexpress CD73 and using CD73 knock-out mice have provided evidence that CD73 inhibitors have potential utility for melanomas, lung cancer, prostate cancer, and breast cancer (see, e.g., Sadej R. (2006) Melanoma Res 16:213-22). Because higher expression levels of CD73 are associated with tumor neovascularization, invasiveness, resistance to chemotherapy, and metastasis, CD73 inhibitors can be used to control tumor progression and metastasis. Other potential utilities are discussed elsewhere herein.

Although the compound of Formula (I) is believed to exert its activity by inhibition of CD73, a precise understanding of the compound's underlying mechanism of action is not required to practice the disclosure. For example, the compound can also exert its activity, at least in part, through modulation (e.g., inhibition) of other components of the purinergic signaling pathway (e.g., CD39). The purinergic signaling system consists of transporters, enzymes and receptors responsible for the synthesis, release, action, and extracellular inactivation of (primarily) ATP and its extracellular breakdown product adenosine (Sperlagh, B. et al. (December 2012) Neuropsychopharmacologia Hungarica 14(4):231-38). There are several potential opportunities for modulation of the signaling process. However, some of these opportunities are more tractable than others.

VII. Combination Therapy

The present disclosure contemplates the use of a compound of Formula (I) (e.g., a crystalline form described herein) in combination with one or more active therapeutic agents. The additional active therapeutic agents can be small chemical molecules; macromolecules such as proteins, antibodies, peptibodies, peptides, DNA, RNA or fragments of such macromolecules; or cellular or gene therapies. In such combination therapy, the various active agents frequently have different, complementary mechanisms of action. Such combination therapy may be advantageous by allowing a dose reduction of one or more of the agents, thereby reducing or eliminating the adverse effects associated with one or more of the agents. The compound of Formula (I) of the present disclosure may also be useful in overcoming adenosine-dependent immunosuppression, leading to enhanced therapeutic efficacy of other agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, a compound of Formula (I) (e.g., a crystalline form described herein) is administered or applied sequentially, e.g., where one agent is administered prior to one or more other agents. In other embodiments, the agents are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The compound of Formula (I) (e.g., a crystalline form described herein) may be used in combination with at least one other (active) agent in any manner appropriate under the circumstances. In one embodiment, treatment with the at least one active agent and the crystalline form of the compound of Formula (I) is maintained over a period of time. In another embodiment, treatment with the at least one active agent is reduced or discontinued (e.g., when the subject is stable), while treatment with the crystalline form of the compound of Formula (I) is maintained at a constant dosing regimen. In a further embodiment, treatment with the at least one active agent is reduced or discontinued (e.g., when the subject is stable), while treatment with the crystalline form of the compound of Formula (I) is reduced (e.g., lower dose, less frequent dosing or shorter treatment regimen). In yet another embodiment, treatment with the at least one active agent is reduced or discontinued (e.g., when the subject is stable), and treatment with the crystalline form of the compound of Formula (I) is increased (e.g., higher dose, more frequent dosing or longer treatment regimen). In yet another embodiment, treatment with the at least one active agent is maintained and treatment with the crystalline form of the compound of Formula (I) is reduced or discontinued (e.g., lower dose, less frequent dosing or shorter treatment regimen). In yet another embodiment, treatment with the at least one active agent and treatment with the crystalline form of the compound of Formula (I) is reduced or discontinued (e.g., lower dose, less frequent dosing or shorter treatment regimen).

Oncology-related Disorders. The present disclosure provides methods for treating and/or preventing a proliferative condition, cancer, tumor, or precancerous disease, disorder or condition with a compound of Formula (I) (e.g., a crystalline form according to this disclosure) and at least one additional therapeutic or diagnostic agent.

In some embodiments, one or more of the additional therapeutic agents is an immunomodulatory agent. Suitable immunomodulatory agents that may be used in the present disclosure target CD40L, B7, and B7RP1; activating monoclonal antibodies (mAbs) to stimulatory receptors, such as, anti-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); indoleamine 2,3-dioxygenase 1 (IDO1) inhibitors and immune-stimulatory oligonucleotides.

In certain embodiments, the present disclosure provides methods for tumor suppression of tumor growth including administration of a compound of Formula (I) (e.g., as a crystalline form described herein) in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) contemplated by the present disclosure include: (i) BCR-ABL kinase inhibitors (e.g., GLEEVEC®); (ii) epidermal growth factor receptor tyrosine kinase inhibitors (EGFR TKIs), including small molecule inhibitors (e.g., gefitinib, erlotinib, afatinib, and osimertinib), and anti-EGFR antibodies; (iii) inhibitors of the human epidermal growth factor (HER) family of transmembrane tyrosine kinases, e.g., HER-2/neu receptor inhibitors (e.g., HERCEPTIN®), and HER-3 receptor inhibitors; (iv) vascular endothelial growth factor receptor (VEGFR) inhibitors including small molecule inhibitors (e.g., axitinib, sunitinib and sorafenib), and anti-VEGF antibodies (e.g., bevacizumab); (v) inhibitors of AKT family kinases or the AKT pathway (e.g., rapamycin); (vi) inhibitors of serine/threonine-protein kinase B-Raf (BRAF), such as, for example, vemurafenib, dabrafenib and encorafenib; (vii) inhibitors of rearranged during transfection (RET), including, for example, selpercatinib and pralsetinib; (viii) tyrosine-protein kinase Met (MET) inhibitors (e.g., tepotinib, tivantinib, cabozantinib and crizotinib); (ix) anaplastic lymphoma kinase (ALK) inhibitors (e.g., ensartinib, ceritinib, lorlatinib, crizotinib, and brigatinib); (x) inhibitors of the RAS signaling pathway (e.g., inhibitors of KRAS, HRAS, RAF, MEK, ERK) as described elsewhere herein; (xi) FLT-3 inhibitors (e.g., gilteritinib); (xii) inhibitors of Trop-2, such as, for example, the antibody drug conjugate sacituzumab govitecan-hziy; (xiii) inhibitors of the JAK/STAT pathway, e.g., JAK inhibitors including tofacitinib and ruxolitinib, or STAT inhibitors such as napabucasin; (xiv) inhibitors of NF-κB; (xv) cell cycle kinase inhibitors (e.g., flavopiridol); (xvi) phosphatidyl inositol kinase (PI3K) inhibitors; and (xix) protein kinase B (AKT) inhibitors (e.g., capivasertib, miransertib). Agents involved in immunomodulation can also be used in combination with the crystal forms described herein for the suppression of tumor growth in cancer patients. In one or more embodiments, the additional therapeutic agent comprises an inhibitor of EGFR, VEGFR, HER-2, HER-3, BRAF, RET, MET, ALK, RAS (e.g., KRAS, MEK, ERK), FLT-3, JAK, STAT, NF-κB, PI3K, AKT, or any combinations thereof.

In other embodiments, the present disclosure provides methods for treating cancer in a subject, including administering to the subject a therapeutically effective amount of a compound of Formula (I) (e.g., as a crystalline form described herein) and at least one chemotherapeutic agent. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU) with or without leucovorin; folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab-paclitaxel, and docetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; anthracyclines; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as abiraterone, apalutamide, darolutamide, flutamide, nilutamide, bicalutamide, leuprolide, enzalutamide, and goserelin; and pharmaceutically acceptable salts, acids or derivatives of any of the above. In certain embodiments, combination therapy includes administration of a hormone or related hormonal agent.

In some embodiments, the additional chemotherapeutic agent is selected from nab-paclitaxel, gemcitabine and combinations thereof. In some embodiments, the additional chemotherapeutic agent is selected from enzalutamide, docetaxel and combinations thereof.

In some embodiments drawn to methods of treating cancer, the administration of a therapeutically effective amount of a compound of Formula (I) (e.g., as a crystalline form described herein) in combination with at least one chemotherapeutic agent results in a cancer survival rate greater than the cancer survival rate observed by administering either agent alone. In further embodiments drawn to methods of treating cancer, the administration of a therapeutically effective amount of a compound of Formula (I) in combination with at least one chemotherapeutic agent results in a reduction of tumor size or a slowing of tumor growth greater than reduction of the tumor size or tumor growth observed by administration of either agent alone.

Combinations of a compound of Formula (I) (e.g., a crystalline form described herein) with a poly(ADP-ribose) polymerase (PARP) inhibitor is also contemplated. Exemplary PARP inhibitors contemplated by this disclosure include olaparib, niraparib and rucaparib.

In one or more embodiments, combinations of a compound of Formula (I) (e.g., a crystalline form described herein) with inhibitors of the Bcl-2 family of proteins, such as, for example inhibitors of BCL-2 (e.g., venetoclax and navitoclax), and inhibitors of MCL-1 are also contemplated.

Combinations of a compound of Formula (I) (e.g., a crystalline form described herein) with inhibitors of the CD47-SIRPα pathway (e.g., the anti-CD47 antibody, magrolimab) are also contemplated.

In one or more embodiments, combinations of a compound of Formula (I) (e.g., a crystalline form described herein) with DNA methyltransferase (DNMT) inhibitors or hypomethylating agents is also contemplated. Exemplary DNMT inhibitors include decitabine, zebularine and azacitadine.

In one or more embodiments, combinations of a compound of Formula (I) (e.g., a crystalline form described herein) with a histone deacetylase (HDAC) inhibitor is also contemplated. Exemplary HDAC inhibitors include vorinostat, givinostat, abexinostat, panobinostat, belinostat and trichostatin A.

In some embodiments, a compound of Formula (I) (e.g., a crystalline form described herein) are combined with a menin-MLL inhibitor.

In some embodiments, combination of a compound of Formula (I) (e.g., a crystalline form described herein) with a isocitrate dehydrogenase (IDH) inhibitor, e.g., IDH-1 or IDH-2, is also contemplated. An exemplary IDH-1 inhibitor is ivosidenib. An exemplary IDH-2 inhibitor is enasidenib.

Additional treatment modalities that may be used in combination with a the compound of Formula (I) (e.g., a crystalline form described herein) include radiotherapy, surgical resection, a monoclonal antibody against a tumor antigen, a complex of a monoclonal antibody and toxin, a T-cell adjuvant, bone marrow transplant, or antigen presenting cells (e.g., dendritic cell therapy) including toll-like receptor (TLR) agonists which are used to stimulate such antigen presenting cells.

Immune Checkpoint Inhibitors. The present disclosure contemplates the use of the compound of Formula (I) (e.g., a crystalline form described herein) in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

Examples of immune checkpoints (ligands and receptors), some of which are selectively upregulated in various types of tumor cells, that are candidates for blockade include PD-1 (programmed cell death protein 1); PD-L1 (PD-1 ligand); BTLA (B and T lymphocyte attenuator); CTLA-4 (cytotoxic T-lymphocyte associated antigen 4); TIGIT (T cell immunoreceptor with Ig and ITIM domains); TIM-3 (T-cell membrane protein 3); LAG-3 (lymphocyte activation gene 3); A2aR (adenosine A2a receptor A2aR); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). See Pardoll, (April 2012) Nature Rev. Cancer 12:252-64.

The present disclosure contemplates the use of the compound of Formula (I) (e.g., a crystalline form described herein) in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA-4 monoclonal antibody ipilimumab (YERVOY®; Bristol-Myers Squibb) became the first immune checkpoint inhibitor to receive regulatory approval in the US. Fusion proteins comprising CTLA-4 and an antibody (CTLA4-Ig; abatcept (ORENCIA®; Bristol-Myers Squibb)) have been used for the treatment of rheumatoid arthritis, and other fusion proteins have been shown to be effective in renal transplantation patients that are sensitized to Epstein Barr Virus. The next class of immune checkpoint inhibitors to receive regulatory approval were against PD-1 and its ligands PD-L1 and PD-L2. Approved anti-PD1 antibodies include nivolumab (OPDIVO; Bristol-Myers Squibb) and pembrolizumab (KEYTRUDA®; Merck) for various cancers, including squamous cell carcinoma, classical Hodgkin lymphoma and urothelial carcinoma. Approved anti-PDL1 antibodies include avelumab (BAVENCIO®, EMD Serono & Pfizer), atezolizumab (TECENTRIQ®; Roche/Genentech), and durvalumab (IMFINZI®, AstraZeneca) for certain cancers, including urothelial carcinoma. While there are no approved therapeutics targeting TIGIT or its ligands CD155 and CD112, those in development include BMS-986207 (Bristol-Myers Squibb), MTIG7192A/RG6058 (Roche/Genentech), OMP-31M32 (OncoMed), and domvanalimab (AB154). In some combinations provided herein, the immune checkpoint inhibitor is selected from ipilmumab, tremelimumab, BMS-986016, IMP-731, IMP-321, cobolimab, MBG453, Sym023, INCAGN2390, LY3321367, BMS, 986258, SHR1702, MEDI-0680, pidilizumab (CT-011), nivolumab, pembrolizumab, avelumab, atezolizumab, budigalimab, BI-75091, camrelizumab, cosibelimab, durvalumab, dostarlimab, cemiplimab, sintilimab, tislelizumab, toripalimab, retifanlimab, sasanlimab, domvanalimab (AB154), and zimberelimab (AB122).

In one aspect of the present disclosure, the compound of Formula (I) (e.g., a crystalline form described herein) is combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), B7-H6, and B7-H7 (HHLA2). Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT13R, LIGHT, DcR3, HVEM, VEGI/TL1A, TRAMP/DR3, EDAR, EDA1, XEDAR, EDA2, TNFR1, Lymphotoxin a/TNF13, TNFR2, TNFa, LT13R, Lymphotoxin a 1132, FAS, FASL, RELT, DR6, TROY, NGFR.

In another aspect, the immuno-oncology agent is a cytokine that inhibits T cell activation (e.g., IL-6, IL-10, TGF-B, VEGF, and other immunosuppressive cytokines) or a cytokine that stimulates T cell activation, for stimulating an immune response.

In one aspect, T cell responses can be stimulated by a combination of an oral formulation comprising a compound of Formula (I) and a chelating agent and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD2. Other agents that can be combined with an oral formulation comprising a compound of Formula (I) and a chelating agent for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (W011/70024, W011/107553, W011/131407, W013/87699, W013/119716, W013/132044) or FPA-008 (W011/140249; W013169264; W014/036357).

In another aspect, the compound of Formula (I) (e.g., a crystalline form described herein) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

Immune Modulators. The present disclosure contemplates the use of the compound of Formula (I) (e.g., a crystalline form described herein) in combination with therapeutic agents that modulate the tumor microenvironment or augment or mediate immune responses. Examples of these agents include indoleamine 2,3-dioxygenase 1 (IDO-1) inhibitors, adenosine receptor antagonists and arginase inhibitors. IDO-1 breaks down tryptophan which impairs the activation of anti-tumor T cells. Similarly, arginase has been shown to be responsible for tumor immune escape through ARG-1, which depletes arginine from the tumor microenvironment leading to impaired T cell function such as stopped proliferation and secretion of cytokines. Exemplary arginase compounds can be found, for example, in WO 2019/173188 and WO 2020/102646. Adenosine signaling through $A_{2A}R$ and $A_{2B}R$ leads to the impairment of maturation and/or activation of T cells, NK cells and dendritic cells, which then impairs the activation of the immune system against cancer cells. In some embodiments, the present disclosure contemplates combination with the adenosine receptor antagonists described in WO/2018/136700, WO 2018/204661, WO 2018/213377, or WO/2020/023846.

In certain embodiments, the present disclosure contemplates the use of a compound of Formula (I) (e.g., a crystalline form described herein) in combination with other agents that modulate the level of adenosine. Such therapeutic agents may act on the other ectonucleotides that catalyze the conversion of ATP to adenosine, including ectonucleoside triphosphate diphosphohydrolase 1 (ENTPD1, also known as CD39 or Cluster of Differentiation 39), which hydrolyzes ATP to ADP and ADP to AMP.

In certain embodiments, the present invention contemplates the use a compound of Formula (I) (e.g., a crystalline form described herein) with inhibitors of HIF-2α, which plays an integral role in cellular response to low oxygen availability. Under hypoxic conditions, the hypoxia-inducible factor (HIF) transcription factors can activate the expression of genes that regulate metabolism, angiogenesis, cell proliferation and survival, immune evasion, and inflammatory response. HIF-2α overexpression has been associated with poor clinical outcomes in patients with various cancers; hypoxia is also prevalent in many acute and chronic inflammatory disorders, such as inflammatory bowel disease and rheumatoid arthritis. Exemplary HIF-2a inhibitors include belzutifan, ARC-HIF2, PT-2385, and those described in PCT/US2020/063000 and PCT/US2021/022912.

In certain embodiments, the present disclosure contemplates the use of a compound of Formula (I) (e.g., a crystalline form described herein) in combination with inhibitors of phosphatidylinositol 3-kinases (PI3Ks), particularly the PI3Kγ isoform. PI3Kγ inhibitors can stimulate an anti-cancer immune response through the modulation of myeloid cells, such as by inhibiting suppressive myeloid cells, dampening immune-suppressive tumor-infiltrating macrophages or by stimulating macrophages and dendritic cells to make cytokines that contribute to effective T-cell responses leading to decreased cancer development and spread. In one embodiment, the PI3Kγ inhibitor is IPI-549. In another embodiment the PI3K inhibitor is chosen from those described in PCT/US2020/035920.

The present disclosure also contemplates the combination of a compound of Formula (I) (e.g., a crystalline form described herein) with one or more RAS signaling inhibitors. Oncogenic mutations in the RAS family of genes, e.g., HRAS, KRAS, and NRAS, are associated with a variety of cancers. For example, mutations of G12C, G12D, G12V, G12A, G13D, Q61H, G13C and G12S, among others, in the KRAS family of genes have been observed in multiple tumor types. Direct and indirect inhibition strategies have been investigated for the inhibition of mutant RAS signaling. Indirect inhibitors target effectors other than RAS in the RAS signaling pathway, and include, but are not limited to, inhibitors of RAF, MEK, ERK, PI3K, PTEN, SOS (e.g., SOS1), mTORC1, SHP2 (PTPN11), and AKT. Non-limiting examples of indirect inhibitors under development include RMC-4630, RMC-5845, RMC-6291, RMC-6236, JAB-3068, JAB-3312, TN0155, RLY-1971, BI1701963. Direct inhibitors of RAS mutants have also been explored, and generally target the KRAS-GTP complex or the KRAS-GDP complex. Exemplary direct RAS inhibitors under development include, but are not limited to, sotorasib (AMG510), MRTX849, mRNA-5671 and ARS1620. In some embodiments, the one or more RAS signaling inhibitors are selected from the group consisting of RAF inhibitors, MEK inhibitors, ERK inhibitors, PI3K inhibitors, PTEN inhibitors, SOS1 inhibitors, mTORC1 inhibitors, SHP2 inhibitors, and AKT inhibitors. In other embodiments the one or more RAS signaling inhibitors directly inhibit RAS mutants.

In some embodiments, this disclosure is directed to the combination of a compound of Formula (I) (e.g., a crystalline form described herein) with one or more inhibitors of anexelekto (i.e., AXL). The AXL signaling pathway is associated with tumor growth and metastasis, and is believed to mediate resistance to a variety of cancer therapies. There are a variety of AXL inhibitors under development that also inhibit other kinases in the TAM family (i.e., TYRO3, MERTK), as well as other receptor tyrosine kinases including MET, FLT3, RON and AURORA, among others. Exemplary multikinase inhibitors include gilteritinib, merestinib, cabozantinib, BMS777607, and foretinib. AXL specific inhibitors have also been developed, e.g., SGI-7079, TP-0903 (i.e., dubermatinib), BGB324 (i.e., bemcentinib) and DP3975.

The present disclosure also contemplates the combination of a compound of Formula (I) (e.g., a crystalline form described herein) with one or more p21-activated kinase 4

(PAK4) inhibitors. PAK4 overexpression has been shown across a variety of cancer types, notably including those resistant to PD-1 therapies. While no PAK4 inhibitors have been approved, some are in development, and exhibit dual PAK4/NAMPT inhibitor activity, e.g., ATG-019 and KPT-9274. In some embodiments, the compounds according to this disclosure are combined with a PAK4 selective inhibitor. In some embodiments, the compounds according to this disclosure are combined with a PAK4/NAMPT dual inhibitor, e.g., ATG-019 or KPT-9274.

Metabolic and Cardiovascular Diseases. The present disclosure provides methods for treating and/or preventing certain cardiovascular- and/or metabolic-related diseases, disorders and conditions, as well as disorders associated therewith, with a compound of Formula (I) (e.g., a crystalline form described herein) and at least one additional therapeutic or diagnostic agent.

Examples of therapeutic agents useful in combination therapy for the treatment of hypercholesterolemia (and atherosclerosis as well) include statins (e.g., CRESTOR®, LESCOL®, LIPITOR®, MEVACOR®, PRAVACOL®, and ZOCOR®), which inhibit the enzymatic synthesis of cholesterol; bile acid resins (e.g., COLESTID, LO-CHOLEST, PREVALITE®, QUESTRAN®, and WELCHOL®), which sequester cholesterol and prevent its absorption; ezetimibe (ZETIA®), which blocks cholesterol absorption; fibric acid (e.g., TRICOR®), which reduces triglycerides and may modestly increase HDL; niacin (e.g., NIACOR®), which modestly lowers LDL cholesterol and triglycerides; and/or a combination of the aforementioned (e.g., VYTORIN® (ezetimibe with simvastatin). Alternative cholesterol treatments that may be candidates for use in combination with the CD73 inhibitors described herein include various supplements and herbs (e.g., garlic, policosanol, and guggul).

The present disclosure encompasses pharmaceutically acceptable salts, acids or derivatives of any of the above.

Immune-related Disorders and Disorders Having an Inflammatory Component. The present disclosure provides methods for treating and/or preventing immune-related diseases, disorders and conditions; and diseases, disorders and conditions having an inflammatory component; with a compound of Formula (I) (e.g., a crystalline form described herein) and at least one additional therapeutic or diagnostic agent.

Examples of therapeutic agents useful in combination therapy for immune- and inflammatory-related diseases, disorders or conditions include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone. Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-10, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE®, HUMIRA®, anti-TNF antibody fragments (e.g., CDP870), and soluble p55 or p75 TNF receptors, derivatives thereof, p75TNFRIgG (ENBREL®) or p55TNFR1gG (LENERCEPT), soluble IL-13 receptor (sIL-13), and also TNFa-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the crystalline forms described herein include interferon-131a (AVONEX®); interferon-131b (BETASERON®); copaxone; hyperbaric oxygen; intravenous immunoglobulin; clabribine; and antibodies to, or antagonists of, other human cytokines or growth factors (e.g., antibodies to CD40 ligand and CD80).

Microbial Diseases. The present disclosure provides methods for treating and/or preventing viral, bacterial, fungal and parasitic diseases, disorders and conditions, as well as disorders associated therewith, with a compound of Formula (I) (e.g., a crystalline form described herein) and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddI, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with a compound of Formula (I) (e.g., a crystalline form described herein) include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present disclosure contemplates the use of the compound of Formula (I) (e.g., a crystalline form described herein) in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present disclosure contemplate the use of a compound of Formula (I) (e.g., a crystalline form described herein) in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of antibacterial agents that are appropriate for use in specific bacterial infections.

Embodiments of the present disclosure contemplate the use of the compound of Formula (I) (e.g., a crystalline form described herein) in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

Other Therapeutic Modalities. In another embodiment, the present disclosure contemplates the use of a compound of Formula (I) (e.g., a crystalline form described herein) in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

In certain embodiments, the present disclosure contemplates the use of the compound of Formula (I) (e.g., a crystalline form described herein) in combination with RNA interference-based therapies to silence gene expression. RNAi begins with the cleavage of longer double-stranded RNAs into small interfering RNAs (siRNAs). One strand of the siRNA is incorporated into a ribonucleoprotein complex known as the RNA-induced silencing complex (RISC), which is then used to identify mRNA molecules that are at least partially complementary to the incorporated siRNA strand. RISC can bind to or cleave the mRNA, both of which inhibits translation.

The present disclosure encompasses pharmaceutically acceptable salts, acids or derivatives of the agents (and members of the classes of agents) set forth above.

Dosing

The compound of Formula (I) (e.g., a crystalline form described herein) may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the compound of Formula (I) (e.g., a crystalline form described herein) may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the compound of Formula (I) (e.g., a crystalline form described herein) may be administered (e.g., orally or parenterally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1 to 1000 milligrams of the active ingredient, particularly 1, 3, 5, 10, 15, 20, 25, 50, 75, 100, 150, 200, 250, 300, 400, 500, 600, 750, 800, 900, and 1000 milligrams of the active ingredient. In some embodiments, the compositions contain from 25 milligrams to 350 milligrams of the active agent. In some embodiments, the compositions contain 50 milligrams. In some embodiments, the compositions contain 100 milligrams of the active agent. In some embodiments, the compositions contain 300 milligrams of the active agent.

For parenteral administration of a compound of formula (I), the compound (e.g., a crystalline form described herein, or a lyophilized form thereof) can be provided prior to its reconstitution in a suitable vehicle. In some embodiments, the compound of formula (I) is provided in an amount of 1 to 1000 milligrams, particularly 1, 3, 5, 10, 15, 20, 25, 50, 75, 100, 150, 200, 250, 300, 400, 500, 600, 750, 800, 900, and 1000 milligrams of the active ingredient. In some embodiments, the compound of Formula (I) is provided in an amount of 25 milligrams to 350 milligrams. In some embodiments, the compound is provided in an amount of 25 milligrams to 120 milligrams. In some embodiments, the compound is provided in an amount of 25 milligrams to 110 milligrams. In some embodiments, the compound is provided in an amount of 25 milligrams to 100 milligrams.

In some embodiments, the compound of Formula (I) (e.g., a crystalline form described herein) may be administered (e.g., orally or parenterally) on a monthly, weekly or daily basis. In some embodiments, the compound of Formula (I) may be administered at least once a month, such as twice a month, three times a month, four times a month, once a week, or daily. In some embodiments, the compound of Formula (I) may be administered once every week, once every two weeks, once every 3 weeks, once every 4 weeks, once every 5 weeks, or once every 6 weeks. In certain embodiments, the compound of Formula (I) may be administered (e.g., orally) one or more times a day. In some embodiments, the compound of formula (I) may be administered (e.g., orally) 1, 2, or 3 times a day. In some embodiments, the compound of Formula (I) may be administered (e.g., orally) once a day. In some embodiments the compound of Formula (I) may be administered (e.g., parenterally) 1, 2, 3, or 4 times a month. In some embodiments, the compound of Formula (I) may be administered (e.g., parenterally) once every other week.

In certain embodiments, the oral formulation comprising a compound of Formula (I) (e.g., a crystalline form described herein) is administered such that a dose of between 50 mg and 350 mg of the crystalline form of a compound of Formula (I), such as 50 mg, 75 mg, 100 mg, 125 mg, 150 mg, 175 mg, 200 mg, 225 mg, 250 mg, 275 mg, 300 mg, 325 mg, or 350 mg is administered daily. In one embodiment, the oral formulation is administered such that a dose of 100 mg of the compound of Formula (I) is administered daily. In another embodiment, the oral formulation is administered such that a dose of 300 mg of the compound of Formula (I) is administered daily.

In certain embodiments, the dosage of the compound of Formula (I) (e.g., a crystalline form described herein) is contained in a "unit dosage form". The phrase "unit dosage form" refers to physically discrete units, each unit containing a predetermined amount of the compound of Formula (I) (e.g., a crystalline form described herein), either alone or in combination with one or more additional agents, sufficient to produce the desired effect. The predetermined amount of the compound of Formula (I) in the unit dosage form can be equal to the desired dosage, or a fraction thereof. For example, the unit dosage form can comprise the desired dose or ½, ⅓, ¼, ⅕, ⅙, 1/7, or ⅛ of the desired dose. In certain such embodiments, the unit dosage form can be administered 1, 2, 3, 4, 5, 6, 7 or 8 times, respectively, to achieve the desired dose of the active ingredient. In one or more embodiments, the predetermined amount of the compound of Formula (I) in the unit dosage form is equal to or is ½ of the desired dose. In certain such embodiments, the unit dosage form is administered 1 or 2 times, respectively, to achieve the desired dose of the active ingredient. It will be appreciated that the parameters of a unit dosage form will depend on the particular agent and the effect to be achieved.

VIII. Kits

The present disclosure also contemplates kits including a compound of Formula (I) (e.g., a crystalline form described herein), and pharmaceutical compositions thereof. The kits are generally in the form of a physical structure housing various components, as described below, and may be utilized, for example, in practicing the methods described above.

A kit can include a compound of Formula (I) disclosed herein (provided in, e.g., a sterile container), which may be in the form of a pharmaceutical composition suitable for administration to a subject. The crystalline form of the compound of Formula (I) can be provided in a form that is ready for use (e.g., a tablet or capsule) or in a form requiring, for example, reconstitution or dilution (e.g., a powder) prior to administration. When the crystalline form of the compound of Formula (I) is in a form that needs to be reconstituted or diluted by a user, the kit may also include diluents (e.g., sterile water), buffers, pharmaceutically acceptable excipients, and the like, packaged with or separately from the crystalline form of the compound of Formula (I). When combination therapy is contemplated, the kit may contain the several agents separately or they may already be combined in the kit. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium. In some embodiments, the actual instructions are not present in the kit, but means for obtaining the instructions from a remote source, e.g., via the internet, are provided.

IX. Examples

The following examples are put forth so as to provide those of ordinary skill in the art with a complete disclosure and description of how to make and use the present disclosure, and are not intended to limit the scope of what the inventors regard as their disclosure, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: min=minute(s); h or hr=hour(s); equiv=equivalents; mg=milligram; g=gram; ml or mL=milliliter; l or L=liter; mM=millimolar; M=molar; HPLC=high performance liquid chromatography; NMR=nuclear magnetic resonance; XRPD=x-ray powder diffraction; DSC=differential scanning calorimetry; DVS=dynamic vapor sorption; RH=relative humidity; HPT=heptane; EtOAc=ethyl acetate; EtOH=ethanol; DCM=dichloromethane; MTBE=methyl tert-butyl ether; MEK=methyl ethyl ketone.

LC: Agilent 1100 series; Mass spectrometer: Agilent G6120BA, single quad

LC-MS method: Agilent Zorbax Eclipse Plus C18, 4.6× 100 mm, 3.5 mM, 35° C., 1.5 mL/min flow rate, a 2.5 min gradient of 0% to 100% B with 0.5 min wash at 100% B; A=0.1% of formic acid/5% acetonitrile/94.9% water; B=0.1% of formic acid/5% water/94.9% acetonitrile Flash column: ISCO Rf+

Reverse phase HPLC: ISCO-EZ; Column: Kinetex 5 mm EVO C18 100 A; 250×21.2 mm (Phenomenex)

X-Ray Powder Diffraction (XRPD)

XRPD analysis was carried out on a PANalytical X'pert pro, scanning the samples between 3 and 35° 2θ. The material was gently ground to release any agglomerates and loaded onto a multi-well plate with Kapton or Mylar polymer film to support the sample. The multi-well plate was then placed into the diffractometer and analyzed using Cu K radiation (α1λ=1.54060 Å; α2=1.54443 Å; β=1.39225 Å; α1:α2 ratio=0.5) running in transmission mode (step size 0.0130° 2θ) using 40 kV/40 mA generator settings.

Differential Scanning Calorimetry (DSC)

Approximately 5 mg of material was weighed into an aluminum DSC pan and sealed non-hermetically with a pierced aluminum lid. The sample pan was then loaded into a Mettler Toledo DSC-3, heated and held at 30° C. until a stable heat-flow response was obtained. Once a stable heat-flow response was obtained, the sample and reference were heated to 450° C. at a scan rate of 5° C./min and the resulting heat flow response monitored. Nitrogen was used as the purge gas, at a flow rate of 50 cm$^3$/min.

Dynamic Vapor Soprtion (DVS)

Approximately 10 mg of sample was placed into a mesh vapor sorption balance pan and loaded into a DVS-1, DVS Intrinsic or DVS Advantage dynamic vapor sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 min, maximum step length 500 min) at 25° C. After completion of the sorption cycle, the sample was dried using the same procedure to 0% RH and then a second sorption cycle back to 90% RH. Two cycles were performed. The weight change during the sorption/desorption cycles were plotted, allowing for the hygroscopic nature of the sample to be determined. XRPD analysis was then carried out on any solid retained.

Example 1: Preparation of crystalline Forms A and B of [({[(2R,3S,4R,5R)-5-(6-chloro-4-{[(1S)-1-(2-fluorophenyl)ethyl]amino}-1H-pyrazolo[3,4-b]pyridin-1-yl)-3,4-dihydroxyoxolan-2-yl]methoxy}(hydroxy)phosphoryl)methyl]phosphonic acid

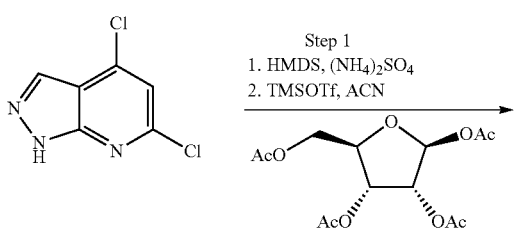

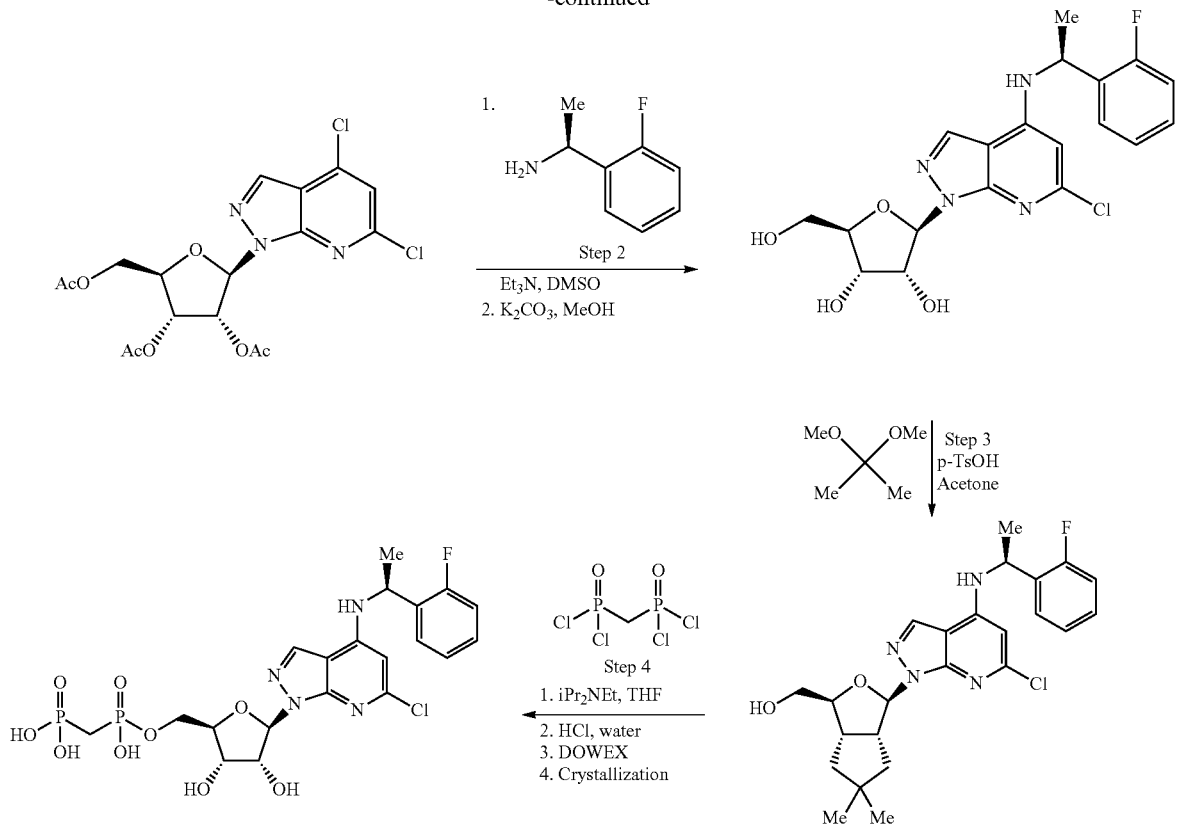

Step 1: The heterocycle (25 g, 133 mmol) and ammonium sulfate (175 mg, 1 mol %) were charged in a 1 L round bottom flask equipped with a magnetic stir bar. HMDS (133 mL, 1M) was added and the mixture was refluxed for 4 hours under an air atmosphere (heating block temperature 155° C.). Excess HMDS was evaporated under vacuum at 60° C. and then the flask was placed under high vacuum at 45° C. for 30 minutes. This operation was repeated to make sure all excess HMDS was removed.

The pale orange oil residue was dissolved in anhydrous MeCN (266 mL) and the sugar (46.55 g, 146.3 mmol) was added. The resulting mixture was stirred until all the sugar was dissolved (typically 5 min., yellow solution). TMSOTf (4.8 mL, 26.6 mmol) was then added dropwise over 20 minutes (slight exotherm). Upon completion of the TMSOTf addition, LCMS analysis showed that all the starting heterocycle was consumed. The reaction was then stirred for 17-20 hours (deeper colored mixture). An LCMS aliquot showed greater than 90% UV purity with a ratio between the desired product and its glycosidic epimer of 97:3. EtOAc (350 mL) and NaHCO$_3$$_{(sat.)}$ (300 mL) were successively added at which point the mixture turned deep blue. The layers were separated and the aqueous layer was extracted once with EtOAc (150 mL). The combined organic layers were dried over Na$_2$S$_2$O$_3$, filtered and evaporated to dryness. The deep blue oil was dissolved in DCM (300 mL). Silica (50 g) and activated charcoal (15 g) were added and the resulting suspension was stirred vigorously for 1.5 hours. It was then filtered over Celite to deliver a clear yellow pale to colorless solution. The filtrated was evaporated to dryness to deliver the crude material. The clear oil was dissolved in EtOAc (1.33 mL/g). The solution was stirred vigorously and hexanes (4.5 mL/g) was added at which point a cloudy mixture is obtained. The mixture was heated to reflux until complete dissolution, cooled to room temperature and seeded with seed crystals. After 1 hour at room temperature the mixture was placed in a fridge (0° C.) for 20 hours. The crystals were then filtered and rinsed with cold MTBE (2×80 mL+1×50 mL) to yield pure product (46.85 g, 79%). The mother liquors were evaporated to dryness and the crystallization procedure was repeated. It delivered additional material (4.45 g, 7%). Global yield is 51.3 g, 86%.

Step 2: A 3-neck 5 L round-bottomed flask fitted was charged with a solution of the product from step 1 (157 g, 353 mmol) in dimethyl sulfoxide (353 mL, 1 M). To the solution was added (1S)-1-(2-fluorophenyl)ethylamine.HCl (93 g, 529 mmol, 1.5 equiv) followed by triethylamine (170 mL, 1.2 mol, 3.5 equiv). The reaction mixture was heated to 80° C. and stirred with an overhead mechanical stirrer for 48 h. The mixture was cooled to room temperature and diluted with methanol (700 mL, 0.5 M). K$_2$CO$_3$ (233 g, 1.2 mol, 3.5 equiv) was added and the reaction stirred at room temperature. After 40 h, the reaction mixture was filtered through celite and the filter cake was washed with methanol (2×200 mL). The solution was concentrated in vacuo to remove volatiles. To the remaining solution was added 3.5 L of water while stirring vigorously. The resulting precipitate was then collected and washed with water (3×1 L) to afford the desired product as a tan solid (139 g, 92%).

Step 3: To a solution of the product from step 2 (45.74 g, 108 mmol) and 2,2-dimethoxypropane (66.3 ml, 541 mmol) in acetone (270 mL) at room temperature was added p-TsOH (2.05 g, 10.8 mmol). The reaction was stirred for two hours then concentrated under reduced pressure. The crude amber oil was reconstituted in EtOAc (1.0 L) and washed with saturated NaHCO$_3$ (500 mL). The organic layer was separated and stirred with activated charcoal then filtered. The filtrate was dried over Na$_2$SO$_4$, filtered and concentrated in vacuo to provide an off-white solid. The solid was suspended with 1:1 EtOAc:hexanes (500 mL) and collected via vacuum filtration. The filter cake was washed with hexane (100 mL) then dried under high vacuum to afford the desired product as a white solid (39.2 g, 78%).

Step 4: To a suspension of methylenebis(phosphonic dichloride) (81.0 g, 324 mmol, 3.0 equiv) in THF (162 mL, 2.0 M) at 0° C. was added N,N-diisopropylethylamine (20.7 mL, 119 mmol, 1.1 equiv). To the resulting mixture was added a solution of the product from step 3 (50.0 g, 108 mmol, 1.0 equiv) in THF (347 mL, 0.31 M) dropwise over the course of 1 h. Following addition, the resulting mixture was stirred at 0° C. for an additional 15 minutes, then the solution was transferred via cannula to a pre-cooled (0° C.) flask containing 0.2 M HCl (1080 mL). The reaction mixture was warmed to 30° C. and stirred at 30° C. for 16 h [acetonide deprotection]. Upon completion, the reaction mixture was washed with 1.5:1 MTBE/THF (5×900 mL). The aqueous phase was diluted with brine (960 mL) and extracted with 2:1 2-MeTHF/THF (1 L). The organic phase was collected and then washed with brine (2×500 mL). To the organic layer was added DOWEX Marathon C H$^+$ Form (20 g/L, 20 g) and stirred for 2 hours at room temperature. The DOWEX beads were removed by filtration and the resulting solution was concentrated under reduced pressure to afford a colorless/off-white foam (crude Formula (I)).

To purify the compound via recrystallization, the solid was dissolved in EtOH (313 mL) with stirring and then CH$_3$CN (1,175 mL) was added over the course of 5 minutes. The resulting clear solution was stirred at 25° C. for 1 h, during which time crystallization occurred. The mixture was allowed to sit at 25° C. for 12 h, and then the white solid was collected by vacuum filtration, rinsed with 6:1 CH$_3$CN/EtOH (150 mL), and dried under reduced pressure at 55° C. for 4 days to afford the product as a white solid (32.6 g, 52% yield, 98.5% UV purity, containing 0.75 wt. % CH$_3$CN). The isolated solid was identified as crystalline Form B by XRPD (see WO 2020/123772).

A sample of crystalline Form B was subsequently dried in a vacuum oven at 60° C. for 16 h, resulting in the isolation of crystalline Form A as determined by XRPD (see WO 2020/123772).

Example 2: Preparation of Crystalline Form I of Formula (I)

A flask was charged with Form A of Example 1 (1.00 g) and denatured EtOH (5 mL, 5 parts). The resulting mixture was heated to ~55-60° C. to form a first clear solution. Toluene (10.0 mL, 10 parts) was added at a temperature of 55-60° C. to form a second clear solution. The second clear solution was allowed to cool to room temperature over ~1.5 hours, and stirred at room temperature overnight (about 18 hours) to form a white suspension. The white solid was collected by vacuum filtration, rinsed with 1:1 EtOH/toluene (2 parts), and dried at 55-60° C. under vacuum for 3 days to afford the Form I as a white solid (0.82 g, 82% yield, containing 0.04 wt % ethanol and about 0 wt % toluene).

The crystalline Form I was characterized by an XRPD pattern as shown in FIG. 1 and was further characterized by a differential scanning calorimetry (DSC) thermogram as shown in FIG. 2.

Similar results are observed using Form B as the starting material.

Example 3: Alternative Preparation of Crystalline Form I of Formula (I)

A flask was charged with 3.5 g of Form A or Form B and suspended in 17.5 mL of anhydrous absolute EtOH. The reaction mixture was heated to 35-40° C., resulting in a clear solution. Next, 35 mL of EtOAc was added to the solution portion wise over a period of 30 minutes while maintaining the temperature at 35-40° C. The mixture was subsequently allowed to cool to 20-25° C., at which time the solution became a slurry. The slurry was allowed to stir for 18 hr. The mixture was further chilled to 0-5° C. and maintained at that temperature for 6 hr. The resulting solids were filtered through a Buchner funnel and suction dried under N$_2$ for 18 hr. The solids were identified as Form I by XRPD.

Similar results are observed using Form B as the starting material.

Example 4: Preparation of Crystalline Form II of Formula (I)

A flask was charged with Form A of Example 1 (1.00 g) and denatured EtOH (5 mL, 5 parts). The resulting mixture was heated to ~55-60° C. for about 15 minutes to form a first clear solution. The first clear solution was allowed to cool to room temperature over ~1.5 to 2 hours, and stirred at room temperature for about 72 hours to form a thick white slurry suspension. Additional ethanol (2 parts) was added to the thick white slurry suspension, and the resulting suspension was reheated to ~55-60° C. to form a second clear solution. The second clear solution was allowed to cool to room temperature over ~1.5 hours, and stirred at room temperature for about 2 hours to form a heavy white slurry suspension. The white solid was collected by vacuum filtration, rinsed with EtOH (2 parts), and dried at 55-60° C. under vacuum for 18 hours to afford the Form II as a white solid (0.37 g, 37% yield, containing 0.68 wt % ethanol).

The crystalline Form II was characterized by an XRPD pattern as shown in FIG. 3; and was further characterized by a differential scanning calorimetry (DSC) thermogram as shown in FIG. 4.

Similar results are observed using Form B as the starting material.

Example 5: Preparation of Crystalline Form III of Formula (I)

A flask was charged with Form A of Example 1 (0.5 g) and denatured EtOH (2.5 mL, 5 parts). The resulting mixture was heated to ~55-60° C. to form a first clear solution. Methyl tert-butyl ether (5 mL, 10 parts) was added at a temperature of 55-60° C. to form a second clear solution. The second clear solution was allowed to cool to room temperature over ~1.5 hours, and stirred at room temperature overnight (about 18 hours) to form a white suspension. The white solid was collected by vacuum filtration, rinsed with 2:1 MTBE/EtOH (2 parts), and dried at 55-60° C. under vacuum for 18 hours to afford the Form III as a white solid (0.34 g, 68% yield, containing about 0 wt % EtOH and 0.04 wt % methyl tert-butyl ether).

The crystalline Form III was characterized by an XRPD pattern as shown in FIG. 5; and was further characterized by a differential scanning calorimetry (DSC) thermogram as shown in FIG. 6.

Similar results are observed using Form B as the starting material.

Example 6: Preparation of Crystalline Form IV of Formula (I)

A flask was charged with Form A of Example 1 (3.0 g) and anhydrous THF (15 mL, 5 parts). The resulting mixture was heated to ~55-60° C. to form a first hazy solution. Ethyl acetate (12 mL, 4 parts) was added at a temperature of 55-60° C. to form a second hazy solution. The second hazy solution was allowed to cool to 50-55° C. and seeded with ~20 mg Form A crystals of the compound of Formula (I) (as disclosed in WO 2020/123772). The resulting mixture was allowed to cool to room temperature over ~1 hour, and seeded again with ~20 mg Form A crystals of the compound of formula (I). The resulting mixture was stirred at room temperature overnight (about 18 hours) to form an off-white suspension. The solid was collected by vacuum filtration, rinsed with 2:1 THF/EtOAc (6 mL, 2 parts), and dried at 55-60° C. under vacuum for 18 hours to afford the Form IV as a white solid (2.8 g, 93% yield, containing 0.05 wt % THF and 0.38 wt % EtOAc).

The crystalline Form IV was characterized by an XRPD pattern as shown in FIG. 7.

Similar results are observed using Form B as the starting material.

Example 7: Preparation of Crystalline Form V of Formula (I)

A flask was charged with Form B of Example 1 (1.00 g) and anhydrous EtOH (5 mL, 5 parts). The resulting slurry was heated to ~35° C. and allowed to stir for 7 hours to form a clear solution. The mixture was cooled to 20-25° C. and stirred for an additional 18 hours, resulting in a white suspension. The white solid was collected by vacuum filtration.

The crystalline Form V was characterized by XRPD as shown in FIG. 8, and was further characterized by a differential scanning calorimetry (DSC) thermogram as shown in FIG. 9. A $^1$H NMR of the solid revealed the presence of 7.6% w/w EtOH, indicating that Form V is an EtOH solvate.

It was subsequently found that Form V slowly converts to Form II when stored at ambient temperature under an $N_2$ blanket (>48 hr for full conversion). Increasing the temperature to 40° C. and drying Form V under vacuum increased the conversion rate to Form II (full conversion observed after 48 hr). Resuspending Form II in a 1:1 EtOH:EtOAc mixture overnight with stirring allowed the recovery of Form V, demonstrating that the relationship between Form II and Form V is reversible.

Example 8: Preparation of Form VI

A 20 mL vial was charged with 0.5 g of Form B and 1.5-2.0 mL EtOH. The suspension was vigorously stirred at 20-25° C. for 3 days. The solid was collected by filtration. Crystalline form VI was characterized by XRPD (FIG. 10) and DSC (FIG. 11).

Example 9: Competitive Slurry Experiments

Crystalline Form a and Form I

A flask was charged with crystalline Form A (1.5 g) and crystalline Form I (1.5 g) with 30 mL of a 1:2 mixture of ethanol (anhydrous) and ethyl acetate. The resulting mixture was allowed to stir at room temperature for 5 hours resulting in a thick white slurry. An additional 6 mL of the 1:2 EtOH (anhydrous):EtOAc mixture was added. The suspension was allowed to stir for 5 days. A small sample of the suspension was pulled from the mixture after 22 hr, 46 hr and 118 hr. The samples were filtered, and dried in an oven at room temperature for 2-3 hr and characterized by XRPD. The results show that Form I is the final form after 46 hr of stirring, indicating that Form I is more stable than Form A under these conditions.

Crystalline Form I and Form V at RT

A 20 mL vial was charged with 0.2 g of Form V and 0.2 g of Form I with 4 mL of a 1:2 EtOH (anhydrous):EtOAc mixture. The resulting suspension was stirred vigorously for 3 days. The suspension was filtered, and the solid was dried under reduced pressure at RT for 3 hr. The isolated solids were identified as Form I by XRPD, indicating that Form I is more stable than Form V under these conditions.

Crystalline Form I and Form V at 35° C.

A 15 mL round bottom flask was equipped with a stir bar, thermometer and $N_2$ inlet, and was charged with 0.25 g Form I and 0.25 g Form V. To the flask was added 6 mL of a 1:2 EtOH (anhydrous):EtOAc mixture was added to the flask resulting in a white suspension. The suspension was heated to 35° C. and stirred vigorously for 2 days. The suspension was filtered, and the resulting solid dried under reduced pressure at RT for 3 hr. The isolated solids were identified as Form I by XRPD, indicating that Form I is more stable than Form V under these conditions.

Crystalline Form I and II at RT

A 20 mL vial was charged with 0.2 g Form I and 0.2 g Form II. To the vial was added 4 mL of a 1:2 EtOH (anhydrous):EtOAc mixture, resulting in a uniform suspension. The suspension was stirred vigorously at RT for 5 days. The suspension was filtered, and the resulting solid dried under reduced pressure at RT for 3 hr. The isolated solids were identified as Form I by XRPD, indicating that Form I is more stable than Form II under these conditions.

Crystalline Form I and II at 35° C.

A 15 mL round bottom flask was equipped with a stir bar, thermometer and $N_2$ inlet, and was charged with 0.2 g Form I and 0.2 g Form II. To the flask was added 5 mL of a 1:2 EtOH (anhydrous):EtOAc mixture was added to the flask resulting in a white suspension. The suspension was heated to 35° C. and stirred vigorously for 2 days. The suspension was filtered, and the resulting solid dried under reduced pressure at RT for 3 hr. The isolated solids were identified as Form I by XRPD, indicating that Form I is more stable than Form II under these conditions.

The results of the competitive slurry experiments are summarized in Table 2 below.

TABLE 2

Results of competitive slurry of crystalline forms in a 1:2 mixture of EtOH(anhydrous):EtOAc

| Starting Material | Temperature | Resulting Form |
|---|---|---|
| Form A vs Form I | RT | Form I |
| Form I vs Form V | RT | Form I |
| Form I vs Form V | 35° C. | Form I |
| Form I vs Form II | RT | Form I |
| Form I vs Form II | 35° C. | Form I |

Example 10. Competitive Slurry of Crystalline Form I, II and V at RT

The relative form stability between Forms I, II and V was investigated by aging mixtures of the mixed forms in EtOH, EtOAc, and mixtures thereof. The Form V starting material contained some Form II as determined by its XRPD pattern.

In two 4 mL vials, enough Form I and Form V (containing some Form II) were mixed with 1 mL of the appropriate solvent to generate a slurry in each vial. The two slurries were combined and shaken at 600 rpm at 20° C. The solids from the slurries were isolated for XRPD characterization at time 0, 1 day and 2 days (FIG. 12A-D). The results are summarized in Table 3 below.

TABLE 3

Observations from competitive slurry conversion testing at 20° C.

| Experiment | V % EtOH in EtOH/EtOAc | End Form by XRPD Started from Forms I + V + II mixture |
|---|---|---|
| a | 100 | Form II |
| b | 80 | Form II |
| c | 67 | Form I + Form II (*) |
| d | 50 | Form I |
| e | 33 | Form I |
| f | 20 | Form I + Form V + Form II (*) |
| g | 0 | Form I + Form V + Form II (*) |

*: after 2 days; slow kinetics.

XRPD patterns of the end solids collected after overnight aging are presented in FIG. 12A-D. It can be seen that both Forms I and V converted to Form II in solvents with ≥80 v % EtOH, while the mixture of Forms I and II remained in 67 v % EtOH system. In 50~33 v % EtOH solvents, Form V converted to Form I, while in ≤20 v % EtOH system Forms I and V remained after 2 aging for two days. The lack of conversion in the ≤20 v % EtOH system was attributed to the low solubility of the crystalline forms.

Example 11. Solubility Profiles of Forms I, II and V in EtOH/EtOAc

Equilibrium solubilities of Form I and Form V were measured in EtOH/EtOAc at different ratios at 20° C. The Form V starting material contains some Form II as determined by XRPD.

Figure 13:
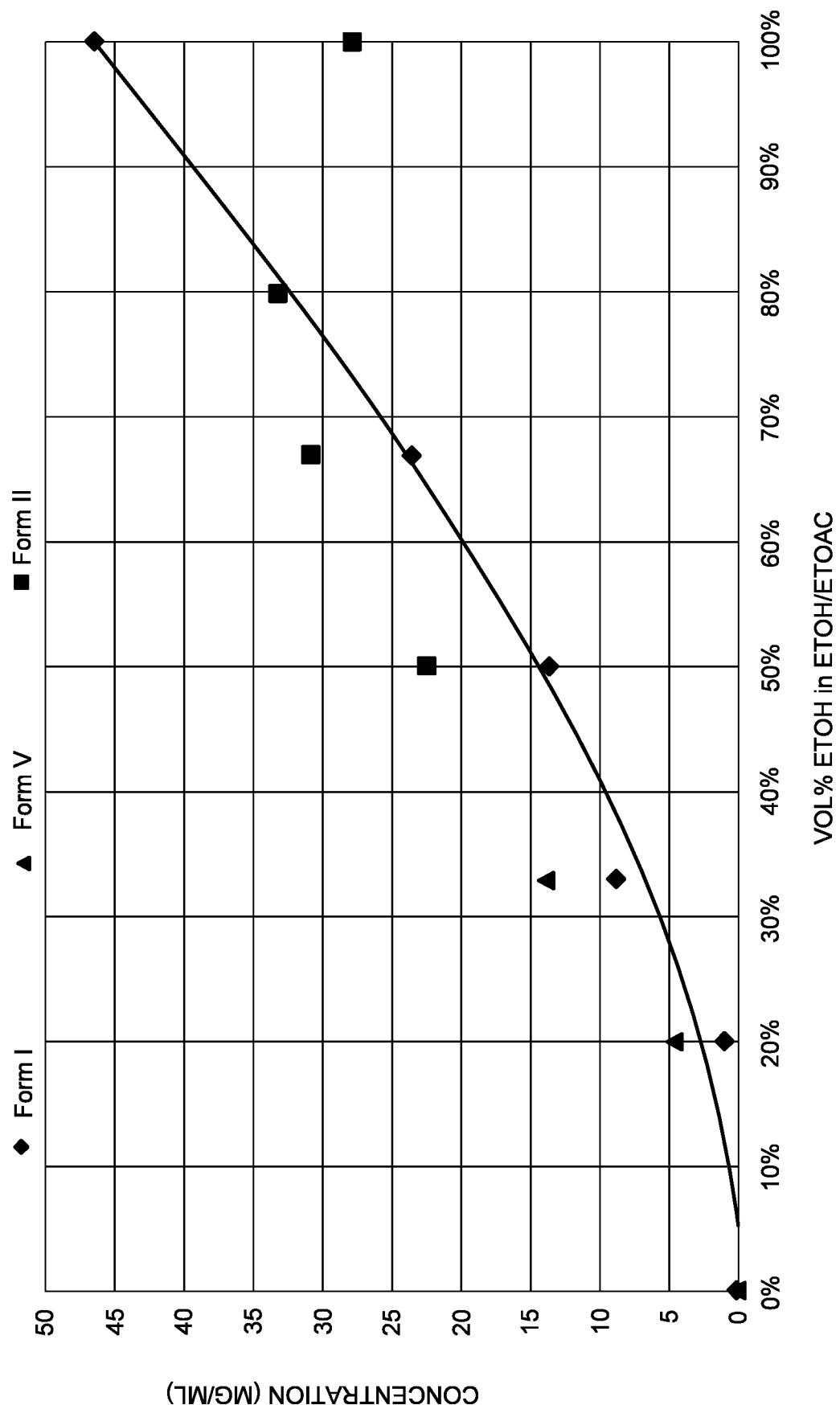
FIG. 13 depicts the solubility profiles of Forms I (diamond), II (square) and V (triangle) in EtOH/EtOAc solvent systems at 20° C.

In a 4 mL vial, 50 mg of the appropriate solid was mixed with 1 mL of each solvent. The resulting slurry was shaken at 600 rpm at 20° C. overnight. The supernatant from each vial was sampled for HPLC for equilibrium solubility, and the solids isolated and characterized by XRPD. The results are plotted in FIG. 13 and summarized in Table 4 below.

TABLE 4

Solubility Assessment of Form I and Form II + V in EtOH/EtOAc

| # | V % EtOH in EtOH/EtOAc | Solubility (mg/mL) | Solubility (wt %) | End Form by XRPD |
|---|---|---|---|---|
| | | Form I Test | | |
| A1 | 100 | 46.54 | 6.4% | Form I |
| B1 | 80 | 32.75 | 4.2% | Form I |
| C1 | 67 | 23.65 | 3.0% | Form I |
| D1 | 50 | 13.71 | 1.7% | Form I |
| E1 | 33 | 8.93 | 1.0% | Form I |
| F1 | 20 | 1.01 | 0.1% | Form I |
| G1 | 0 | 0.00 | 0.0% | Form I |
| | | Form II + V Test | | |
| A2 | 100 | 28.05 | 3.7% | Form II |
| B2 | 80 | 33.37 | 4.2% | Form II |
| C2 | 67 | 30.88 | 3.8% | Form II |
| D2 | 50 | 22.60 | 2.8% | Form II |
| E2 | 33 | 13.99 | 1.7% | Forms II + V |
| F2 | 20 | 4.68 | 0.6% | Forms II + V |
| G2 | 0 | 0.12 | 0.0% | Forms II + V |

The solubility profile shows that ethanol increases solubilities of Forms I and V and EtOAc is an anti-solvent. Maximum solubility of ~46 mg/mL was observed for Form I in pure EtOH. No crystal form change was observed in Form I vials. In vials containing a mixture of Forms II and V, Form II was the final form in high ethanol (≥50 v %) systems. With low ethanol content (<50 v %), no form change was observed in vials containing a mixture of Form II and V.

The data support that a) Form I is more stable than Forms II and V in EtOAc rich solvent system except for too high EtOAc (with too low solubility), and b) Form II is more stable than Forms I and V in EtOH rich or EtOAc lean solvent systems.

Example 12: Polymorphic Relationship Map Based on EtOH:EtOAc Solvent Systems

Figure 14:
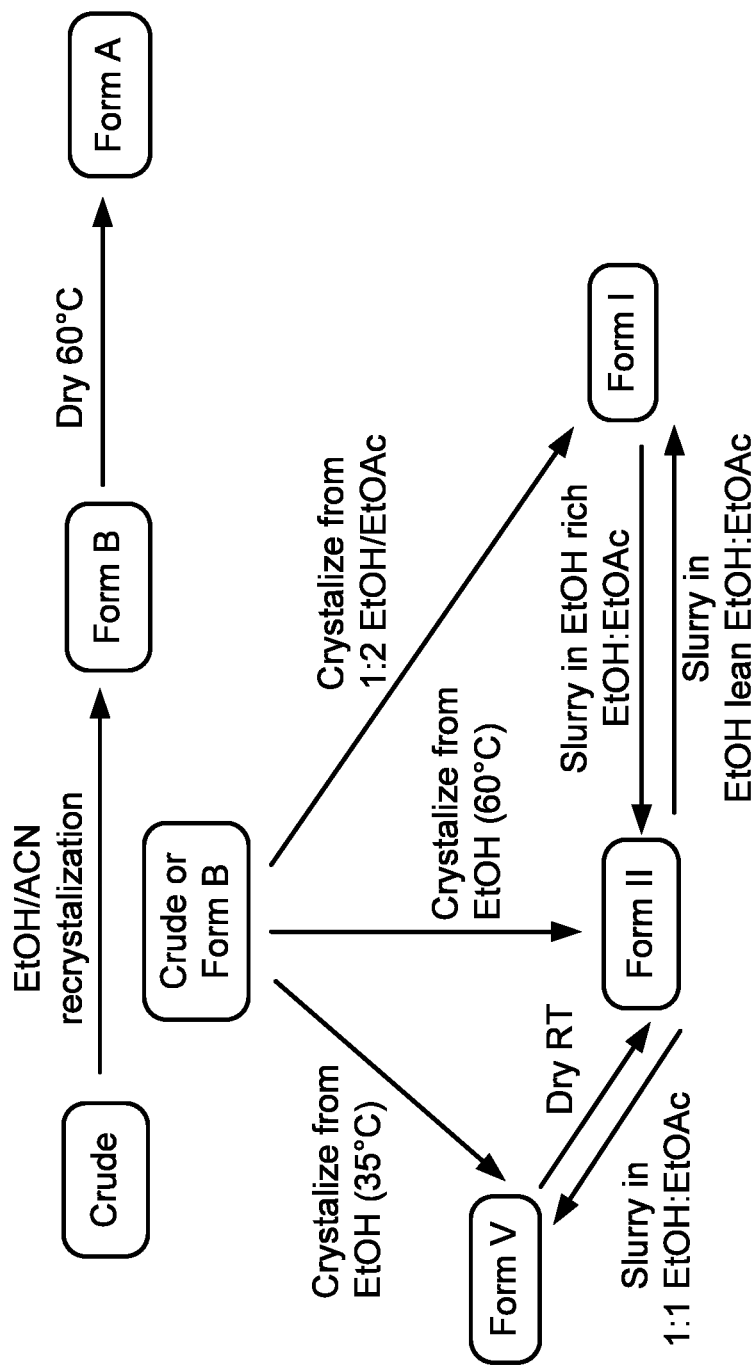
FIG. 14 depicts a polymorphic relationship map based on observations of slurry experiments using EtOH:EtOAc solvent systems. The conditions depicted in the relationship map are merely exemplary, and are not intended to represent all routes that can be used to generate the depicted crystalline forms.

A map of the polymorphic relationships between crystalline Form I, II and V was deduced from observations from EtOH:EtOAc solvent systems (FIG. 14). From the EtOH:EtOAc solvent systems, it has been found that a) EtOAc rich solvent systems favor Form I isolation; and b) EtOAc lean or free solvent systems favor Form II isolation.

Example 13: Solubility Profiles of Forms I, II and V in EtOH:Heptane

Equilibrium solubilities of Forms I, II and V were measured in EtOH/Heptane (HPT) solutions of different ratios at 20 and 35° C.

In 4 mL test vial, the appropriate solids (Form I or Form II containing Form V) were mixed with ~1 mL of each solvent to generate slurry. The resulting slurry was shaken at 600 rpm at 20 and 35° C. overnight. After overnight aging, supernatant from each vial was sampled for HPLC for equilibrium solubility, solids were isolated to check by XRPD.

Figure 15:
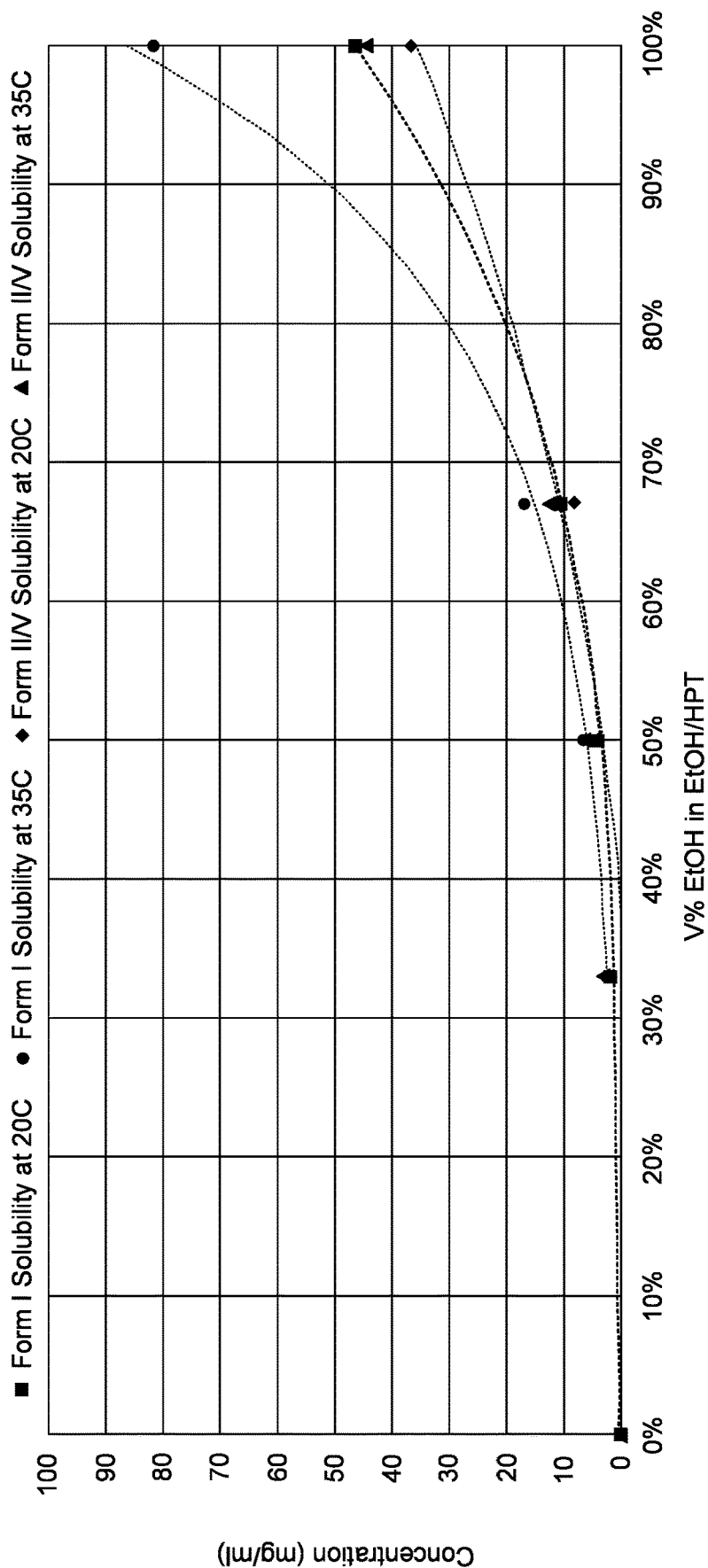
FIG. 15 shows the solubility profile of Form I at 20° C. (square), Form I at 35° C. (circle), a mixture of Form II and V at 20° C. (diamond), and a mixture of Form II and V at 35° C. (triangle) in EtOH/heptane solvent systems.

FIG. 15 plots the solubility profiles of Forms I and the mixture of Forms II and V in EtOH/HPT at 20 and 35° C. HPT is shown as an effective anti-solvent. Form I solubility is higher than the solubility of Form II/V mixtures at all solvent ratios, indicating Form II/V as the most stable form under these conditions. The large solubility difference between Forms I and the mixture of Forms II and V under EtOH rich condition implies that isolating Form II/V from EtOH/HPT is easier than isolating Form I.

Example 14. DVS Characterization of Forms I and II

Figure 16:
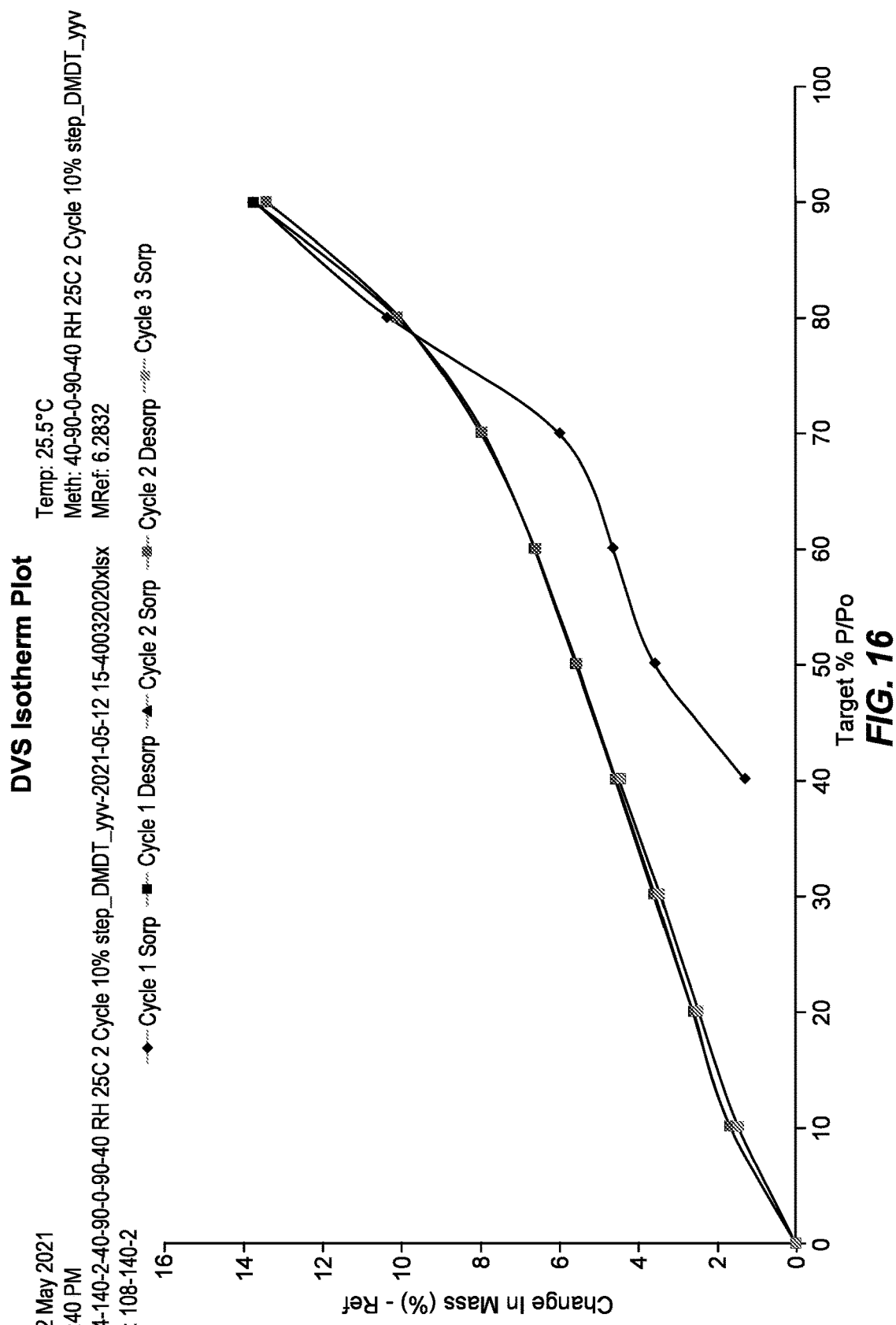
FIG. 16 shows a dynamic vapor sorption (DVS) isotherm of Form I of the compound of Formula (I).
Figure 17:
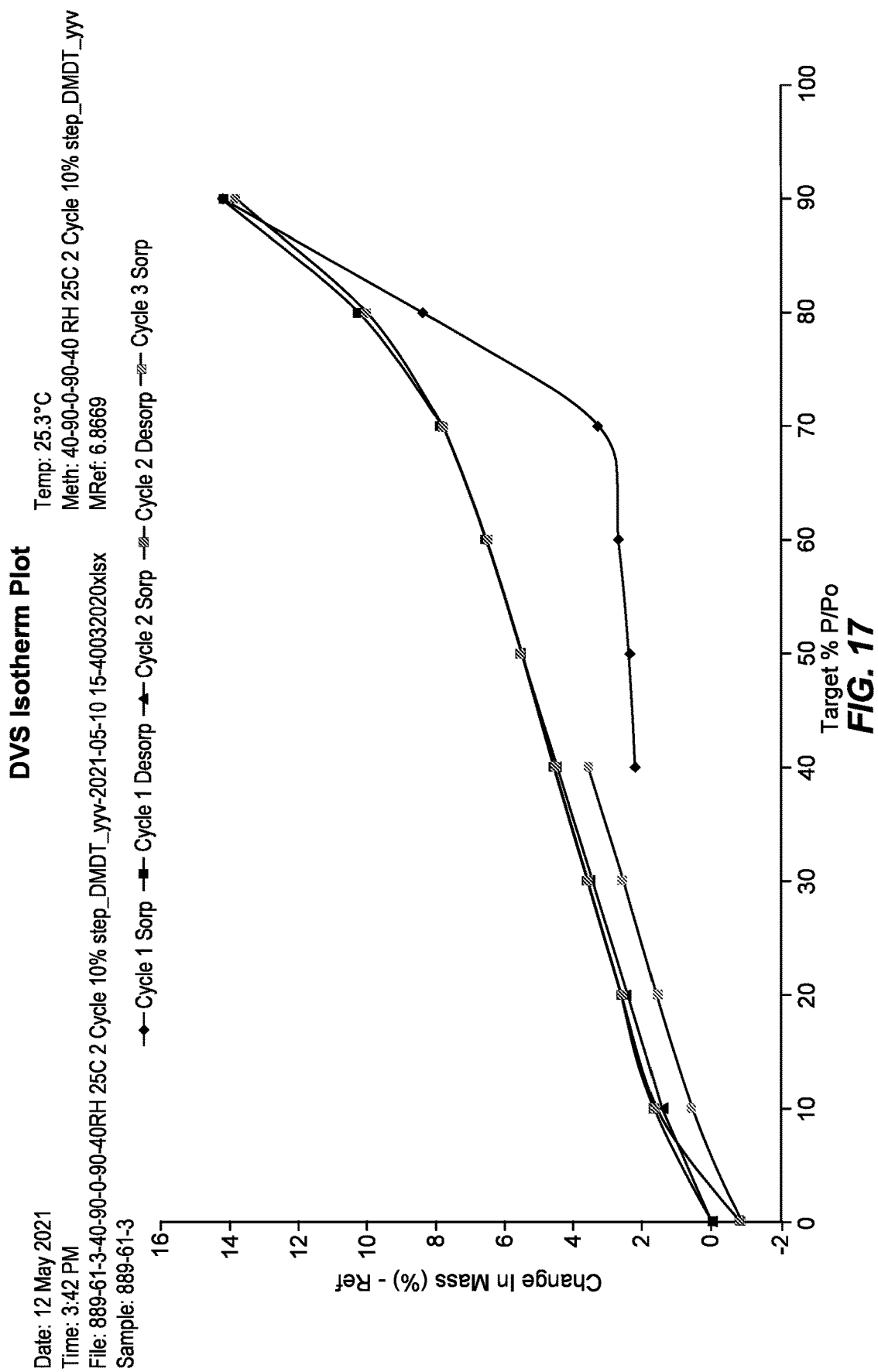
FIG. 17 shows a dynamic vapor sorption (DVS) isotherm of Form II of the compound of Formula (I).

Form I and II were analyzed by dynamic vapor sorption (DVS) at 25° C. (FIG. 16 and FIG. 17). Form II demonstrated much less water uptake from 40% to 70% relative humidity (RH) than Form I. Characterization of the post- DVS samples by XRPD showed that both forms underwent conversion to Form VI during the experiment.

Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. Crystalline Form I of a compound of Formula (I):

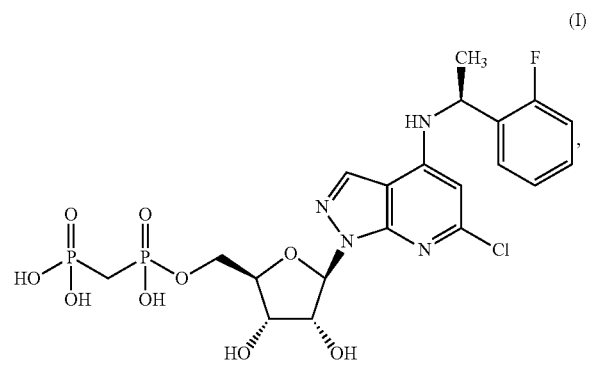 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

characterized by an X-ray powder diffraction (XRPD) pattern comprising peaks at 11.1, 13.8, 18.6, 20.1, 23.0, and 24.8 degrees 2θ (±0.2 degrees 2θ).

2. The crystalline Form I of claim 1, wherein the XRPD pattern further comprises one or more peaks at 11.6, 14.7, 15.4, 16.6, 17.0, 19.3, 21.3, 22.1, 24.8, 26.6, 27.3, and 29.1 degrees 2θ (±0.2 degrees 2θ).

3. The crystalline Form I of claim 1, characterized by an X-ray powder diffraction pattern that is substantially in accordance with FIG. 1.

4. The crystalline Form I of claim 1, further characterized by a differential scanning calorimetry (DSC) thermogram comprising an endothermic peak at about 163.9° C.

5. The crystalline Form I of claim 1, further characterized by a melting point onset of about 155.1° C. as determined by a differential scanning calorimetry thermogram (DSC).

6. The crystalline Form I of claim 4, wherein the DSC thermogram is substantially in accordance with FIG. 2.

7. Crystalline Form II of a compound of Formula (I):

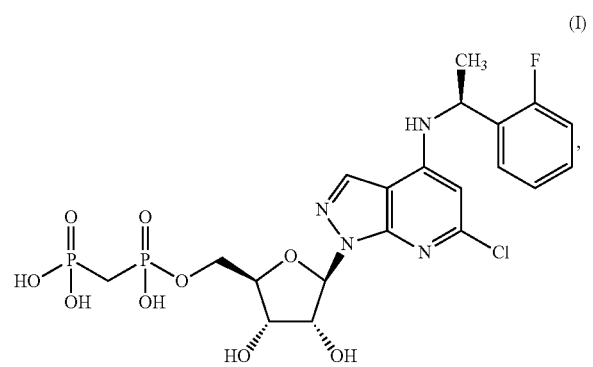 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

characterized by an X-ray powder diffraction (XRPD) pattern comprising peaks at 16.5, 22.8, and 24.6 degrees 2θ (±0.2 degrees 2θ).

8. The crystalline Form II of claim 7, wherein the XRPD pattern further comprises one or more peaks at 10.1, 10.8, 12.8, 13.7, 17.7, and 19.0 degrees 2θ (±0.2 degrees 2θ).

9. The crystalline Form II of claim 7, characterized by an X-ray powder diffraction pattern that is substantially in accordance with FIG. 3.

10. The crystalline Form II of claim 7, further characterized by a differential scanning calorimetry (DSC) thermogram comprising an endothermic peak at about 166.5° C.

11. The crystalline Form II of claim 7, further characterized by a melting point onset of about 157.4° C. as determined by a differential scanning calorimetry thermogram (DSC).

12. The crystalline Form II of claim 10, wherein the DSC thermogram is substantially in accordance with FIG. 4.

13. Crystalline Form V of a compound of Formula (I):

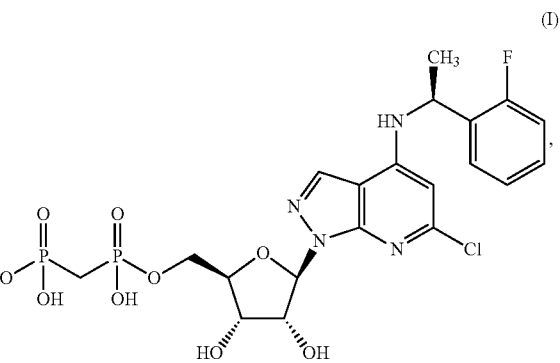

characterized by an X-ray powder diffraction (XRPD) pattern comprising peaks at 15.8, 16.3, 16.8, 18.5, 19.1, 21.7, 22.1, and 23.0 degrees 2θ (±0.2 degrees 2θ).

14. The crystalline Form V of claim 13, wherein the XRPD pattern further comprises one or more peaks at 10.4, 15.1, 19.7, and 23.6 degrees 2θ (±0.2 degrees 2θ).

15. The crystalline Form V of claim 13, characterized by an X-ray powder diffraction pattern that is substantially in accordance with FIG. 8.

16. The crystalline Form V of claim 13, further characterized by a differential scanning calorimetry (DSC) thermogram comprising an endothermic peak at about 150.4° C.

17. The crystalline Form V of claim 13, further characterized by a melting point onset of about 135.8° C. as determined by a differential scanning calorimetry thermogram (DSC).

18. The crystalline Form V of claim 16, wherein the DSC thermogram is substantially in accordance with FIG. 9.

19. A pharmaceutical composition comprising a crystalline form of any one of claim 1, 7, or 13, and a pharmaceutically acceptable excipient.

20. A method of treating a disease, disorder, or condition, mediated at least in part by CD73, said method comprising administering an effective amount of a crystalline form of the compound of any one of claim 1, 7, or 13, to a subject in need thereof.

21. The method of claim 20, wherein the disease, disorder, or condition is cancer.

22. The method of claim 21, wherein the cancer is selected from the group consisting of melanoma, colon cancer, pancreatic cancer, breast cancer, prostate cancer, lung cancer, leukemia, a brain tumor, lymphoma, ovarian cancer, and Kaposi's sarcoma.

23. A method of treating cancer in a subject, said method comprising administering to said subject an effective amount of a crystalline form of the compound of any one of claim 1, 7, or 13, and at least one additional therapeutic agent.

* * * * *